US007713530B2

(12) United States Patent
Williamson et al.

(10) Patent No.: US 7,713,530 B2
(45) Date of Patent: May 11, 2010

(54) HIV-1 SUBTYPE ISOLATE REGULATORY/ACCESSORY GENES, AND MODIFICATION AND DERIVATIVES THEREOF

(75) Inventors: Carolyn Williamson, Cape Town (ZA); Joanne Heidi van Harmelen, Cape Town (ZA); Clive Maurice Gray, Johannesburg (ZA); William Bourn, Cape Town (ZA); Salim Abdool Karim, Durban (ZA)

(73) Assignees: The South African Medical Research Council, Cape Town (ZA); University of Cape Town, Cape Town (ZA)

( * ) Notice: Subject to any disclaimer, the term of this patent is extended or adjusted under 35 U.S.C. 154(b) by 0 days.

(21) Appl. No.: 12/182,479

(22) Filed: Jul. 30, 2008

(65) Prior Publication Data

US 2009/0076245 A1 Mar. 19, 2009

Related U.S. Application Data

(62) Division of application No. 10/494,131, filed as application No. PCT/IB02/04550 on Oct. 31, 2002, now Pat. No. 7,479,547.

(30) Foreign Application Priority Data

Oct. 31, 2001 (ZA) .................................. 2001/8978

(51) Int. Cl.
*A61K 39/38* (2006.01)
*A61K 39/12* (2006.01)
*A61K 39/21* (2006.01)
*C07K 14/00* (2006.01)

(52) U.S. Cl. .............. 424/184.1; 424/185.1; 424/188.1; 424/199.1; 530/350

(58) Field of Classification Search ........................ None
See application file for complete search history.

(56) References Cited

FOREIGN PATENT DOCUMENTS

| WO | WO 00/26416 | 5/2000 |
|---|---|---|
| WO | WO 02/04493 A2 | 1/2002 |
| WO | WO 02/04494 A2 | 1/2002 |
| WO | WO 02/04494 A3 | 1/2002 |
| WO | WO 02/04993 A2 | 1/2002 |
| WO | WO 02/04993 A3 | 1/2002 |
| WO | WO 02/22080 A2 | 3/2002 |
| WO | WO 03/004620 A2 | 1/2003 |
| WO | WO 03/004657 A1 | 1/2003 |
| WO | WO 03/037919 A3 | 5/2003 |

OTHER PUBLICATIONS

Gao, F. et al., "Molecular Cloning and Analysis of Functional Envelope Genes from Human Immunodeficiency Virus Type 1 Sequence Subtypes A through G," Journal of Virology, vol. 70, No. 3, 1651-1667, 1996, GENPEPT ANGIS Sequence, Accession No. AAB61130, and EMBL ANGIS Sequence, Accession No. HIUU52953.

Gao, F. et al., "Codon Usage Optimization of HIV Type 1 Subtype C *gag, pol, env*, and *nef* Genes: in Vitro Expression and Immune Responses in DNA-Vaccinated Mice," AIDS Research and Human Retroviruses, vol. 19, No. 9, 817-823, 2003, GENBANK ANGIS Sequence, Accession No. AY181198, and GENPEPT ANGIS Sequence, Accession No. AA065396.

GENBANK ANGIS Sequence, Accession No. AF075702, (Definition)—HIV-1 Isolate SE8603 from Uganda, complete genome, Submitted (Jul. 1, 1998) by Department of Infectious Disease Epidemiology, National Public Health Institute, Mannerheimintie 166, Helsinki FIN-00300, Finland, Web page available at www.langis.orq.au/bin/WebANGIS/QueryDB/qdb?BrowseCode, as available via the Internet and printed Feb. 18, 2004.

GENPEPT ANGIS Sequence, Accession No. AAD41673, (Definition)—HIV-1 isolate SE8603 from Uganda, complete genome, Submitted (Jul. 1, 1998) Department of Infectious Disease Epidemiology, National Public Health Institute, Mannerheimintie 166, Helsinki FIN-00300, Finland, Web page available at www.1angis.org.au/bin/WebANGIS/QueryDB/qdb?do$_{13}$ call. pl+4615+AAD41673, as available via the Internet and printed Feb. 18, 2004.

GENPEPT ANGIS Sequence, Accession No. AAL05314, (Definition)—HIV-1 Isolate Du151 from South Africa, partial genome, AIDS Research and Human Retroviruses, vol. 17, No. 16, 1527-1531, 2001, Web page available at www1.angis.org.au/bin/WebANGIS/QueryDB/qdb?do_call.pl+4615+AAL05314, as available via the Internet and printed Feb. 18, 2004.

GENBANK ANGIS Sequence, Accession No. AY043173, (Definition)—HIV-1 Isolate Du151 from South Africa, partial genome, AIDS Research and Human Retroviruses, vol. 17, No. 16, 1527-1531, 2001, Web page available at www1.angis.org.au/bin/WebANGIS/QueryDB/qdb?do_call.pl+genback+AY04317, as available via the Internet and printed Feb. 17, 2004.

Index of Lab Research, web page at www.web.archive.org/web/20021121171118/www.aids.har.../consensus_sequence, as available via the Internet and printed Feb. 27, 2004.

Jubier-Maurin, V. et al., "Genetic Characterization of the *nef* Gene from Human Immunodeficiency Virus Type 1 Group M Strains Representing Genetic Subtypes A, B, C, E, F, G, and H," AIDS Research and Human Retroviruses, vol. 15, No. 1, 23-32, 1999, GENBANK ANGIS Sequence, Accession No. HIV232977, and GENPEPT ANGIS Sequence, Accession No. CAA13458.

Kong, W-P. et al., "Immunogenicity of Multiple Gene and Clade Human Immunodeficiency Virus Type 1 DNA Vaccines," Journal of Virology, vol. 77, No. 23, 12764-12772, 2003.

Lole, K. et al., "Full-Length Human Immunodeficiency Virus Type 1 Genomes from Subtype C-Infected Seroconverters in India, with Evidence of Intersubtype Recombination," Journal of Virology, vol. 73, No. 1, 152-160, 1999, GENBANK ANGIS Sequence, Accession No. AF067154, and GENPEPT ANGIS Sequence, Accession No. AAD12078.

(Continued)

*Primary Examiner*—Bo Peng
(74) *Attorney, Agent, or Firm*—Kilpatrick Stockton LLP

(57) ABSTRACT

The invention describes HIV-1 subtype isolate regulatory/accessory genes, and modifications and derivatives thereof. The genes which are described are the tat, nef and rev genes. Consensus amino acid sequences are also disclosed. The invention also relates to a vaccine including two or more of the nucleotide sequences, and nucleotide sequences from the pol and/or gag genes of HIV-1.

8 Claims, 26 Drawing Sheets

OTHER PUBLICATIONS

Mashishi, T. et al., "Conserved Domains of Subtype C Nef from South African HIV Type 1-Infected Individuals Include Cytotoxic T Lymphocyte Epitope-Rich Regions," AIDS Research and Human Retroviruses, vol. 17, No. 17, 1681-1687, 2001, GENBANK ANGIS Sequence, Accession No. AF397535, GENPEPT ANGIS Sequence, Accession No. AAK98474, GENBANK ANGIS Sequence, Accession No. AF397542, and GENPEPT ANGIS Sequence, Accession No. AAK98481.

Mashishi TN, et al., "HIV-1 Isolate ZADU151 from South Africa nef gene", Entrez Accession No. AF397535, Jan. 11, 2002.

Novitsky, V., et al., "Human Immunodeficiency Virus Type 1 Subtype C Molecular Phylogeny: Consensus Sequence for an AIDS Vaccine Design?" Journal of Virology, vol. 76, No. 11, Jun. 2002, pp. 5435-5451, XP002248733.

Okuda, K. et al., "Induction of Potent Humoral and Cell-Mediated Immune Responses Following Direct Injection of DNA Encoding the HIV Type 1 env and rev Gene Products," AIDS Research and Human Retroviruses, vol. 11, No. 8, 933-943, 1995.

Rodenburg, C. et al., "Near Full-Length Clones and Reference Sequences for Subtype C Isolates of HIV Type 1 from Three Different Continents," AIDS Research and Human Retroviruses, vol. 17, No. 2, 161-168, 2001, GENBANK ANGIS Sequence, Accession No. AF286227, GENPEPT ANGIS Sequence, Accession No. AAK30998, GENBANK ANGIS Sequence, Accession No. AF286225, and GENPEPT ANGIS Sequence, Accession No. AAK30980.

Harvard AIDS Institute Online—Jun. 2002, XP002248734, Retrieved from the Internet: www.aids.Harvard.edu/lab_research/consensus_sequence/Tat.pdf>. Retrieved on Jul. 22, 2003.

Van Harmelen, J. et al., "Characterization of Full-Length HIV Type 1 Subtype C Sequences from South Africa." AIDS Research and Human Retroviruses, vol. 17, No. 16, Nov. 1, 2001, pp. 1527-1531, XP002248735.

Van Harmelen, J. et al., Database EBI Online—Nov. 13, 2001; "HIV-1 Isolate Du422 From South Africa, Partial Genome," Database Accession No. AY043175; XP002248737.

Van Harmelen, J. et al., Database EBI Online—Nov. 13, 2001; "HIV-1 Isolate Du151 From South Africa, Partial Genome," Database Accession No. AY043173; XP002248738.

Van Harmelen, J. et al., Database EBI Online—Dec. 1, 2001; "HIV-1 Tat Protein From Strain Du422," Database Accession No. Q901X5; XP002248739.

Van Harmelen, J. et al., Database EBI Online—Dec. 1, 2001; "HIV-1 Tat Protein From Strain Du151," Database Accession No. Q901Z3; XP002248740.

Cheng-Mayer, C. et al., Database EBI Online—Aug. 19, 1998, "HIV-1 Tat and Rev1 Genes, Second Exons," Database Accession No. M66535, XP002248741.

Los Alamos HIV Database Online—Dec. 1996, XP002248803, Retrieved from the Internet: www.hiv-web.lanl.gov/content/hiv-db/COMPENDIUM/1996/PART-I/tat.pdf>. Retrieved on Jul. 23, 2003.

Los Alamos HIV Database Online—Dec. 1996, XP002248804, Retrieved from the Internet: www.hiv-web.lanl.gov/content/hiv-db/COMPENDIUM/1996/PART-I/tat.pdf>. Retrieved on Jul. 23, 2003.

Williamson, C. et al., "Designing HIV-1 Subtype C Vaccines for South Africa," South African Journal of Science, Associated Scientific and Technical Societies of South Africa, SA, vol. 96, No. 6, Jun. 2000, pp. 318-324, XP008009291.

Novitsky, V. et al., "Molecular Cloning and Phylogenetic Analysis of Human Immunodeficiency virus Type 1 Subtype C: A Set of 23 Full-Length Clones From Botswana," Journal of Virology, US, vol. 73, No. 5, May 1999, pp. 4427-4432, XP002144689.

Megede, J. et al., "Increased Expression and Immunogenicity of Sequence-Modified Human Immunodeficiency virus Type 1 *gag* Gene," Journal of Virology, US, vol. 74, No. 6, Mar. 2000, pp. 2628-2635, XP000980650.

ATGGAGCCAATAGATCCTAACCTAGAGCCCTGGAACCATCCAGGAAGTCAGCCTAATACT⁶⁰
CCTTGTAATAACTGCTATTGTAAACACTGTAGCTACCATTGTCTAGTTTGCTTTCAGACA¹²⁰
AAAGGCTTAGGCATTTCCTATGGCAGGAAGAAGCGGAGACAGCGACGAAGCACTCCTCCA¹⁸⁰
AGCAGTGAAGATCATCAAAATCCTATATCAAAGCAACCCTTATCCCAAACCCGAGGGGAC²⁴⁰
CCGACAGGCTCGGAAGAATCGAAGAAGAAGGTGGAGAGCAAGACAAAGACAGATCCATTC³⁰⁰
GATTAG                                                    ³⁰⁶

Figure 1

MEPIDPNLEPWNHPGSQPNTPCNNCYCKHCSYHCLVCFQTKGLGISYGRKKRRQRRSTPP⁶⁰
SSEDHQNPISKQPLSQTRGDPTGSEESKKKVESKTKTDPFD                ¹⁰¹

Figure 2

ATGGAGCCAATAGATCCTAACCTAGAGCCCTGGAACCATCCAGGAAGTCAACCTAACACT⁶⁰
CCTTGTACTAAATGCTATTGTAAATACTGCAGCTATCATTGTCTAGTTTGCTTTCAGACA¹²⁰
AAAGGCTTAGGCATTTCCTATGGCAGGAAGAAGCGGACACAGCGACGAAGCACTCCTCCA¹⁸⁰
AGCAGTGAGGATCATCAAAATCTTATATCAGAGCAGCCCTTACCCCAAGCCCGAGGGGTC²⁴⁰
CCGACAGGCTCGGAAGAATCGAAGAAGAAGGTGGAGAGCAAGACAAAAACAGATCCATTC³⁰⁰
GATTAG                                                    ³⁰⁶

Figure 3

MEPIDPNLEPWNHPGSQPNTPCTKCYCKYCSYHCLVCFQTKGLGISYGRKKRRQRRSTPP⁶⁰
SSEDHQNLISEQPLPQARGVPTGSEESKKKVESKTKTDPFD                ¹⁰¹

Figure 4

ATGGGGGGCAAGTGGTCAAAAAGCAGCATAGTGGGATGGCCTGCTGTAAGAGAAAGAATA⁶⁰
AGAAGAACTGAGCCAGCAGCAGAGGGAGTAGGACCAGCATCTCAAGACTTAGATAAACAT¹²⁰
GGAGCGCTTACAAGCAGCAACACAGCCCACAATAATCCTGACTGTGCCTGGCTACAAGCA¹⁸⁰
CAAGAGGAGGAAGAAGACGTAGGTTTTCCAGTCAGACCTCAGGTGCCTCTAAGACCAATG²⁴⁰
ACTTATAAGGCAGCATTCGATCTCAGCTTCTTTTTAAAAGAAAAGGGGGACTGGAAGGG³⁰⁰
TTAATTCACTCTAAGAGAAGACAAGACATTCTTGATTTGTGGGTCTATCACACACAAGGC³⁶⁰
TACTTCCCTGATTGGCAAAACTACACGCCGGGACCAGGAGTCAGATACCCACTGACCTTT⁴²⁰
GGATGGTGCTTCAAGCTAGTGCCAGTTGATCCAAGGGAAGTAGAAGAGGCCAACAAAGGA⁴⁸⁰
GAAAACAACTGTTTGCTACACCCTATGAGCCAGCATGGAATGGAGGATGCAGACAGAGAA⁵⁴⁰
GTATTAAGATGGGTGTTTGACAGCAGTCTAGCACGCAGACACCTGGCCCGCGAGAACAT⁶⁰⁰
CCGGAGTATTACAAAGAC                                        ⁶¹⁸

Figure 5

MGGKWSKSSIVGWPAVRERIRRTEPAAEGVGAASQDLDKHGALTSSNTAHNNPDCAWLQA⁶⁰
QEEEPEVGFPVRPQVPLRPMTYKAAFDLSFFLKEKGGLEGLIYSKKRQDILDLWVYHTQG¹²⁰
YFPDWQNYTPGPGVRLPLTFGWCFKLVPVDPEEVEEANKGENNCLLHPLSQHGMEDADRE¹⁸⁰
VLKWVFDSSLARRHLAREKHPEYYKDC                                  ²⁰⁷

Figure 6

ATGGCAGGAAGAAGCGGAGACAGCGACGAAGCACTCCTCCAAGCAGTGAAGATCATCAAA⁶⁰
ATCCTATATCAAAGCAACCCTTATCCCAAACCCGAGGGGACCCGACAGGCTCGGAAGAAT¹²⁰
CGAAGAAGAAGGTGGAGAGCAAGACAAGACAGATCCATTCGATTAGTGAGCGGATTCTT¹⁸⁰
AGCACTTGCCTGGGACGATCTGCGGAGCCTGTGCCTCTTCAGCTACCACCAATTGAGAGA²⁴⁰
CTTCATATTGACTGCAGCGAGAGCAGCGGAACTTCTGGGACGCAGCAGTCTCAGGGGACT³⁰⁰
GCAGAGAGGGTGGGAAGTCCTTAA                                     ³²⁴

Figure 7

MAGRSGDSDEALLQAVKIIKILYQSNPYPKPEGTRQARKNRRRRWRARQRQIHSISERIL⁶⁰
STCLGRSAEPVPLQLPPIERLHIDCSESSGTSGTQQSQGTAERVGSP              ¹⁰⁷

Figure 8

```
GGATCCGCGG CCGCAAGCTT GCCACCATGG TAGGCATTTC CTATGGCAGG⁵⁰
AAGAAGCGGA GACAGCGACG AAGCACTCCT CCAAGCAGTG AGGATCATCA¹⁰⁰
AAATCCTATA TCAAAGCAGC CCTTACCCCA AACCCGAGGG GACCCGACAG¹⁵⁰
GCTCGGAAGA ATCGAAGAAG AAGGTGGAGA GCAAGACAAA AACAGATCCA²⁰⁰
TTCGATTGTA AATACTGCAG CTATCATTGT CTAGTTTGCT TTCAGACAAA²⁵⁰
AGGCTTAGGT ATTAGCTATG GAAGGAAGAA ACGGATGGAG CCAATAGATC³⁰⁰
CTAACCTAGA GCCCTGGAAC CATCCAGGAA GTCAACCTAA CACTCCTTGT³⁵⁰
AATAAATGCT ATTGTAAGTA CTGTTCATAT CATTGCCTAG TT            ³⁹²
```
Bold= Restriction sites and Kozac sequence engineered

Figure 9

```
GGATCCGCGG CCGCAAGCTT GCCACCATGG TGGGCATCAG CTACGGCCGC⁵⁰
AAGAAGCGCC GCCAGCGCCG CAGCACCCCG CCCAGCAGCG AGGACCACCA¹⁰⁰
GAACCCCATC AGCAAGCAGC CCCTGCCCCA GACCCGCGGC GACCCCACCG¹⁵⁰
GCAGCGAGGA GAGCAAGAAG AAGGTGGAGA GCAAGACCAA GACCGACCCC²⁰⁰
TTCGACTGCA AGTACTGCAG CTACCACTGT CTGGTGTGCT TCCAGACCAA²⁵⁰
GGGCCTGGGC ATCTCCTACG GCGCAAGAA ACGGATGGAG CCCATCGACC³⁰⁰
CCAACCTGGA GCCCTGGAAC CACCCCGGCA GCCAGCCCAA CACCCCCTGC³⁵⁰
AACAAGTGCT ACTGCAAATA CTGCTCCTAC CACTGCCTCG TG            ³⁹²
```
Bold= Restriction sites and Kozac sequence engineered

Figure 10

```
MLGISYGRKK RRQRRSTPPS SEDHQNPISK QPLPQTRGDP TGSEESKKKV⁵⁰
ESKTKTDPFD CKYCSYHCLV CFQCKGLGIS YGRKKRMEPI DPNLEPWNHP¹⁵⁰
GSQPNTPCNK CYCKYCSYHC LV                              172
```

Figure 11

```
GTGGGATGGC CTGCTGTAAG AGAAAGAATA AGAAGAACTG AGCCAGCAGC⁵⁰
AGAGGGAGTA GGACCAGCAT CTCAAGACTT AGATAAACAT GGAGCGCTTA¹⁰⁰
CAAGCAGCAA CACAGCCCAC AATAATCCTG ACTGTGCCTG GCTACAAGCA¹⁵⁰
CAAGAGGAGG AAGAAGACGT AGGTTTTCCA GTCAGACCTC AGGTGCCTCT²⁰⁰
AAGACCAATG ACTTATAAGC CAGCATTCGA TCTCAGCTTC TTTTTAAAAG²⁵⁰
AAAAGGGGGG ACTGGAAGGC TTAATTCACT CTAAGAGAAG ACAAGACATT³⁰⁰
CTTGATTTGT GGGTCATCA CACACAAGGC TACTTCCCTG ATTGGCAAAA³⁵⁰
CTACACGCCG GGACCAGGAG TCAGATACCC ACTGACCTTT GGATGGTGCT⁴⁰⁰
TCAAGCTAGT GCCAGTTGAT CCAAGGGAAG TAGAAGAGGC CAACAAAGGA⁴⁵⁰
GAAAACAACT GTTTGCTACA CCCTATGAGC CAGCATGGAA TGGAGGATGC⁵⁰⁰
AGACAGAGAA GTATTAAGAT GGGTGTTTGA CAGCAGTCTA GCACGCAGAC⁵⁵⁰
ACCTGGCCCG CGAGAAACAT CCGGAGTATT ACAAAGACTA GGAATTCTCT⁶⁰⁰
AGAGCGGCCG CGTCGAC                                   617
```

Bold= Restriction sites engineered

Figure 12

```
GTGGGCTGGC CCGCCGTGCG CGAGCGCATC CGCCGCACCG AGCCCGCCGC⁵⁰
CGAGGGCGTG GGCCCCGCCA GCCAGGACCT GGACAAGCAC GGCGCCCTGA¹⁰⁰
CCAGCAGCAA CACCGCCCAC AACAACCCCG ACTGCGCCTG GCTGCAGGCC¹⁵⁰
CAGGAGGAGG AGGAGGACGT GGGCTTCCCC GTGCGCCCCC AGGTGCCCCT²⁰⁰
GCGCCCCATG ACCTACAAGG CCGCCTTCGA CCTGAGCTTC TTCCTGAAGG²⁵⁰
AGAAGGGCGG CCTGGAGGGC CTGATCCACA GCAAGCGCCG CCAGGACATC³⁰⁰
CTGGACCTGT GGGTGTACCA CACCCAGGGC TACTTCCCCG ACTGGCAGAA³⁵⁰
CTACACCCCC GGCCCCGGCG TGCGCTACCC CCTGACCTTC GGCTGGTGCT⁴⁰⁰
TCAAGCTGGT GCCCGTGGAC CCCCGCGAGG TGGAGGAGGC CAACAAGGGC⁴⁵⁰
GAGAACAACT GCCTGCTGCA CCCCATGAGC CAGCACGGCA TGGAGGACGC⁵⁰⁰
CGACCGCGAG GTGCTGCGCT GGGTGTTCGA CAGCAGCCTG GCCCGCCGCC⁵⁵⁰
ACCTGGCCCG CGAGAAGCAC CCCGAGTACT ACAAGGACTG AGAATTCTCT⁶⁰⁰
AGAGCGGCCG CGTCGAC                                   617
```

Bold= Restriction sites engineered

Figure 13

```
VGWPAVRERI RRTEPAAEGV GPASQDLDKH GALTSSNTAH NNPDCAWLQA⁵⁰
QEEEEDVGFP VRPQVPLRPM TYKAAFDLSF FLKEKGGLEG LIHSKRRQDI¹⁰⁰
LDLWVYHTQG YFPDWQNYTP GPGVRYPLTF GWCFKLVPVD PREVEEANKG¹⁵⁰
ENNCLLHPMS QHGMEDADRE VLRWVFDSSL ARRHLAREKH PEYYKD    196
```

Figure 14

```
GGATCCGCGG CCGCAAGCTT GCCACCATGG TAGGCATTTC CTATGGCAGG⁵⁰
AAGAAGCGGA GACAGCGACG AAGCACTCCT CCAAGCAGTG AGGATCATCA¹⁰⁰
AAATCCTATA TCAAAGCAGC CCTTACCCCA AACCCGAGGG GACCCGACAG¹⁵⁰
GCTCGGAAGA ATCGAAGAAG AAGGTGGAGA GCAAGACAAA AACAGATCCA²⁰⁰
TTCGATTGTA AATACTGCAG CTATCATTGT CTAGTTTGCT TTCAGACAAA²⁵⁰
AGGCTTAGGC ATTTCCTATG GCAGGAAGAA GCGGATGGAG CCAATAGATC³⁰⁰
CTAACCTAGA GCCCTGGAAC CATCCAGGAA GTCAACCTAA CACTCCTTGT³⁵⁰
AATAAATGCT ATTGTAAATA CTGCAGCTAT CATTGTCTAG TTGTGGGATG⁴⁰⁰
GCCTGCTGTA AGAGAAAGAA TAAGAAGAAC TGAGCCAGCA GCAGAGGGAG⁴⁵⁰
TAGGACCAGC ATCTCAAGAC TTAGATAAAC ATGGAGCGCT TACAAGCAGC⁵⁰⁰
AACACAGCCC ACAATAATCC TGACTGTGCC TGGCTACAAG CACAAGAGGA⁵⁵⁰
GGAAGAAGAC GTAGGTTTTC CAGTCAGACC TCAGGTGCCT CTAAGACCAA⁶⁰⁰
TGACTTATAA GGCAGCATTC GATCTCAGCT TCTTTTTAAA AGAAAAGGGG⁶⁵⁰
GGACTGGAAG GGTTAATTCA CTCTAAGAGA AGACAAGACA TTCTTGATTT⁷⁰⁰
GTGGGTCTAT CACACACAAG CTACTTCCC TGATTGGCAA AACTACACGC⁷⁵⁰
CGGGACCAGG AGTCAGATAC CCACTGACCT TTGGATGGTG CTTCAAGCTA⁸⁰⁰
GTGCCAGTTG ATCCAAGGGA AGTAGAAGAG GCCAACAAAG GAGAAAACAA⁸⁵⁰
CTGTTTGCTA CACCCTATGA GCCAGCATGG AATGGAGGAT GCAGACAGAG⁹⁰⁰
AAGTATTAAG ATGGGTGTTT GACAGCAGTC TAGCACGCAG ACACCTGGCC⁹⁵⁰
CGCGAGAAAC ATCCGGAGTATTACAAAGACTAGGAATTCTCTAGAGCGGCCGC¹⁰⁰⁰
GTCGAC                                                 ¹⁰⁰⁶
```

Bold= Restriction sites engineered

Underlined= Kozac sequence and start ATG

TG= junction between shuffled *tat* and *nef*

Figure 15

```
MVGISYGRKK RRQRRSTPPS SEDHQNPISK QPLPQTRGDP TGSEESKKKV⁵⁰
ESKTKTDPFD CKYCSYHCLV CFQTKGLGIS YGRKKRMEPI DPNLEPWNHP¹⁰⁰
GSQPNTPCNK CYCKYCSYHC LVVGWPAVRE RIRRTEPAAE GVGPASQDLD¹⁵⁰
KHGALTSSNT AHNNPDCAWL QAQEEEDVG FPVRPQVPLR PMTYKAAFDL²⁰⁰
SFFLKEKGGL EGLIHSKRRQ DILDLWVYHT QGYFPDWQNY TPGPGVRYPL²⁵⁰
TFGWCFKLVP VDPREVEEAN KGENNCLLHP MSQHGMEDAD REVLRWVFDS³⁰⁰
SLARRHLARE KHPEYYKD                                    ³¹⁸
```

Figure 16

```
GGATCCGCGG CCGCAAGCTT GCCACCATGG TGGGCATCAG CTACGGCCGC⁵⁰
AAGAAGCGCC GCCAGCGCCG CAGCACCCCG CCCAGCAGCG AGGACCACCA¹⁰⁰
GAACCCCATC AGCAAGCAGC CCCTGCCCCA GACCCGCGGC GACCCCACCG¹⁵⁰
GCAGCGAGGA GAGCAAGAAG AAGGTGGAGA GCAAGACCAA GACCGACCCC²⁰⁰
TTCGACTGCA AGTACTGCAG CTACCACTGT CTGGTGTGCT TCCAGACCAA²⁵⁰
GGGCCTGGGC ATCTCCTACG GCGCAAGAA ACGGATGGAG CCCATCGACC³⁰⁰
CCAACCTGGA GCCCTGGAAC CACCCCGGCA GCCAGCCCAA CACCCCCTGC³⁵⁰
AACAAGTGCT ACTGCAAATA CTGCTCCTAC CACTGCCTCG TGGTGGGCTG⁴⁰⁰
GCCCGCCGTG CGCGAGCGCA TCCGCCGCAC CGAGCCCGCC GCCGAGGGCG⁴⁵⁰
TGGGCCCCGC CAGCCAGGAC CTGGACAAGC ACGGCGCCCT GACCAGCAGC⁵⁰⁰
AACACCGCCC ACAACAACCC CGACTGCGCC TGGCTGCAGG CCCAGGAGGA⁵⁵⁰
GGAGGAGGAC GTGGGCTTCC CCGTGCGCCC CCAGGTGCCC CTGCGCCCCA⁶⁰⁰
TGACCTACAA GGCCGCCTTC GACCTGAGCT TCTTCCTGAA GGAGAAGGGC⁶⁵⁰
GGCCTGGAGG GCCTGATCCA CAGCAAGCGC CGCCAGGACA TCCTGGACCT⁷⁰⁰
GTGGGTGTAC CACACCCAGG GCTACTTCCC CGACTGGCAG AACTACACCC⁷⁵⁰
CCGGCCCCGG CGTGCGCTAC CCCCTGACCT TCGGCTGGTG CTTCAAGCTG⁸⁰⁰
GTGCCCGTGG ACCCCGCGA GGTGGAGGAG GCCAACAAGG GCGAGAACAA⁸⁵⁰
CTGCCTGCTG CACCCCATGA GCCAGCACGG CATGGAGGAC GCCGACCGCG⁹⁰⁰
AGGTGCTGCG CTGGGTGTTC GACAGCAGCC TGGCCCGCCG CCACCTGGCC⁹⁵⁰
CGCGAGAAGC ACCCCGAGTA CTACAAGGAC TGAGAATTCT CTAGAGCGGC¹⁰⁰⁰
CGCGTCGAC                                            ¹⁰⁰⁶
```

Bold= Restriction sites engineered

Underlined= Kozac sequence and start ATG

GG= junction between shuffled, codon optimised tat and nef

Figure 17

```
                                                          40
ZATatcon    MEPVDPNLEPWNHPGSQPKTACNKCYCKHCSYHCLVCFQT      SEQ ID NO: 39
RB13        MEPVDPKLEPWNHPGSQPKTACTQCYCKKCSYHCLVCFQT      SEQ ID NO: 40
Du151       MEPIDPNLEPWNHPGSQPNTPCTKCYCKYCSYHCLVCFQT      SEQ ID NO: 41
Du368       MEPIDPNLEPWNHPGSQPKTPCTNCYCKHSSYHCLVCFQT      SEQ ID NO: 42
Du123       MEPVDPNLDPWNHPGSQPKTPCTKCYCKHCSYHCLVCFQT      SEQ ID NO: 43
Du204       MEPVDLDLEPWNNPGSQPKTACNKCYCKHCSYHCLVCFQT      SEQ ID NO: 44
CTSc2       MEPVDPNLEPWNHPGSQPKTACNPCYCKKCSYHCLVCFQK      SEQ ID NO: 45
RB28        MEPVDPNLEPWNHPGSQPKTACNKCYCKVCSYHCLVCFQT      SEQ ID NO: 46
GG2         ------NLEPWNHPGSQPKTACNPCYCKHCSYHCLVCFQT      SEQ ID NO: 47
GG10        ------NLEPWNHPGSQPKTPCNKCYCKHCSYHCLVCFQT      SEQ ID NO: 48
Du422       MEPIDPNLEPWNHPGSQPNTPCNNCYCKHCSYHCLVCFQT      SEQ ID NO: 49
Du281       MEPVDPNLEPWNHPGSQPLTPCNKCYCKHCSYHCLVCFQT      SEQ ID NO: 50
Du179       MEPIDPNLEPWNHPGSQPKTACNKCFCKRCSYHCQFCFLT      SEQ ID NO: 51
RB12        MEPIDPNLEPWNHPGSQPKTPCNKCYCKRCSYHCLACFQT      SEQ ID NO: 52
GG4         MEPTDPNLEPWNHPGSQPKTPCNKCYCKRCSYHCLVCFQK      SEQ ID NO: 53
Du156       MEPVDPNLEPWNHPGSQPKTPCNTCYCKHCSYHCLVCFQT      SEQ ID NO: 54
Du285       MEPVDPKLEPWNHPGSQPKTPCNSCYCKKCSYHCLVCFQK      SEQ ID NO: 55
CTSc1       MDPIDPNLEPWNHPGSQPKTACNKCYCKRCCYHCLVCFQK      SEQ ID NO: 56

80
ZATatcon    KGLGISYGRKKRRQ-RRSAPPSSEDHQNLISKQPLPQTRG
RB13        KGLGISYGRKKRRQ-RRAPPSSEDHQNPISKQPLPRTRG
Du151       KGLGISYGRKKRRQ-RRSTPPSSEDHQNLISEQPLPQARG
Du368       KGLGISYGRKKRRQ-RRSTPPSSEDHQNLISKQPLSQPEG
Du123       KGLGISYGRKKRRQ-RRSTPPSSEDHQNLISKQPLPQRG
Du204       KGLGISYGRKKRRQQRRSTPSSSKDHQNPISKQPLPQPRG
CTSc2       KGLGISYGRKKRRQ-RRTAPPSSEDHQNPISKQPFPRTQG
RB28        KGLGISYGRKKRRQ-RRSAPPSSEDHQNPISKQPLPTRR
GG2         KGLGISYGRKKRRQ-RQTAPPSSEDHQNPISKQPLPQTRG
GG10        KGLGISYGRKKRRQ-RQTTPPSSEDHQNLVSKQPLSQTRG
Du422       KGLGISYGRKKRRQ-RRSTPPSSEDHQNPISKQPLSQTRG
Du281       KGLGISYGRKKRRQ-RRSTPPSSEDHQNLVSKQPLPQTRG
Du179       KGLGISYGRKKRRQ-RRSAPPSSEDHQNPISKQPLPQTRG
RB12        KGLGISYGRKKRRQ-RRSTPPSSKNHQNPVSKQPLPQTRG
GG4         KGLGISYGRKKRRQ-RRNAPPSSEDHQNLISKQPLPQTRG
Du156       KGLGISYGRKKRRQ-RRSTPPSNKDHQNPVPKQPLPQPRG
Du285       KGLGIYYGRKKQRQ-RRRAPPSNKDHQNPVPKQ-------
CTSc1       KGLGISYGRKKRRQ-RRSAPPSNKDHQNPVSKQ-------

101
ZATatcon    DPTGSEESKKKVESKTETDPFD
RB13        DSTGSEESKKKVESKTETDQFD
Du151       VPTGSEESKKKVESKTKTDPFD
Du368       NSTGSEKSKKKVESKTRTDPFD
Du123       DSTGSEESKKKVESKTKTDQFD
Du204       DSTGSEESKKKVESKTQTDPFA
CTSc2       DPTGSEESKKKVESKTKTDQFD
RB28        DPTGSEESKKKVESKAEADPFD
GG2         DPTGSEESKKKVESKTKTDPFD
GG10        DPTGSEESKKKVESKTETDPFDW
Du422       DPTGSEESKKKVESKTKTDPFD
Du281       DPTGSEESKKKVESKTKTDPFD
Du179       DPTGSEKSKKKVESKTETDPFD
RB12        DPTGSEESKKKVESKTETDPFD
GG4         DPTGSEESKKKVESKTETDPFD
Du156       DSTGSEESKKKVESKTKTDPFD
Du285       ----------------------
CTSc1       ----------------------
```

|          |                                                                              | SEQ ID NO: |
|----------|------------------------------------------------------------------------------|------------|
| ZANefcon | MGGKWSKSSIVGWPAVRERIRR----------TEPAAEG--------VGAASQDLDKHG                  | 57 |
| rb28     | MGGKWSKSSIGGWPAIRERIRR----------AKPAAEG--------VGAASQDLEKHG                  | 58 |
| gg5      | MGGKWSKSSIVGWPAVRERMRK----------TEPAAEG--------VGAASQDLDKHG                  | 59 |
| Du151    | MGGKWSKSSIVGWPAVRERIRRT---------EPAAEG--------VGAASQDLDKHG                   | 60 |
| rb12     | MGGKWSKSSIVGWPAVRERIRQTR--------IEPAAEG--------VGAASQDLDKYG                  | 61 |
| Du422    | MGGKWSKSSLAGWPAVRERIRRT---------EPAAEG--------VGAASRDLEKHG                   | 62 |
| Du123    | MGGKWSKSSIIGWPEVRERIRRT---------EPAAEG--------VGAASRDLEKYG                   | 63 |
| Du368    | MGGKWSKSSIIGWPTEGERRRRAKPT----IRRTEPAAEG--------VGAASQDLEKYG                 | 64 |
| Du467    | MGGKWSKSSIVGWPTERERRRRAKPT----KRRPEPAAEG--------VGAASQDLDKYG                 | 65 |
| Du457    | MGGKWSKSSIIGWPEERER----------IRRTEPAAEG--------VGAASRDLDKYG                  | 66 |
| Du258    | MGGKWSKSSIIGWPEVREGIRRT---------EPAAEG--------VGAASRDLDKYG                   | 67 |
| Du179    | MGGKWSKSSIVGWPTVRERMRRT---------DPAAEG--------VGAASQDLDKHG                   | 68 |
| SW-10    | MGGKCSKSSIVGWPEIRERIRQTR--------TGPAAEG--------VGAASQDLDKYG                  | 69 |
| gg3      | MGGKWSKSSIVGWPAVRERIRRA---------EPAAEG--------VGAASRDLDKHG                   | 70 |
| rb18     | MGNKWSKSSIVGWPAVRERIRRT---------EPAAEG--------VGAASQDLDKHG                   | 71 |
| SW-7     | MGGKWSKSSIVGWPAVRERIRRTRPNGRERIRQTEPAAEG--------VGAASQDLDKYG                 | 72 |
| CTSc2    | MGGKLSKSSIVGWPEVRERLRRAGS---------AAEG--------VGAASQDLDRHG                   | 73 |
| gg2      | MGGKWSKSSIVGWPEVRERLRRTEP---------AAEG--------VGTASQDLDKYG                   | 74 |
| COT2     | MGGKWSKGSIVGWPAVRERIRRTVPT----AKRTEPAAEG--------VGPASRDLDKYG                 | 75 |
| COT6     | MGGKWSKGSIVGWPAVRERIRRTVPT----AKRTEPAAEG--------VGPASRDLDKYG                 | 76 |
| SW-15    | MGGKWSKSSIVGWPAVRERIRRAGP-----GRRAEPAAEG--------VGAASRDLDKYG                 | 77 |
| SW-5     | MGGKWSKSSIVGWPAVRERIRRAGP-----GRRAEPAAEG--------VGAASRDLDKYG                 | 78 |
| gg6      | MGSKWSKSSIVGWPAVRERIRQTS---------AAEG--------VGAASQDLDKHG                    | 79 |
| SW-20    | MGGQWSKSSIIGWPAVRERIRKTTPT----AERVEAAAVG-------VGAASQDLEKHG                  | 80 |
| rb15     | MGGKWSKSSIVGWPAVRERMRR---------ARTEPAAEG--------VGAASRDLEKHG                 | 81 |
| gg10     | MGGKWSKRSVVGWTEIRDRMRRTRP--------TAPAAEG--------VGAASQDLDRHG                 | 82 |
| gg4      | MGNKWSKS----WPSVRERIRRARPA---AEERTRPAAEG--------VGTASQDLDKHG                 | 83 |
| rb13     | MGNKWSKSSIVGWPAVRDRIRRTEP-------RTEPAAVG--------VGAASQDLDKHG                 | 84 |
| rb21     | MGNKWSKS----WPAVRDRMRRTRP----------AAEG--------VGAASQDLDKHG                  | 85 |
| SW9      | MGGKWSKRSLGGWPAVRERMRRTEPAAE-RIRQTEPAAEG--------VGAASQDLDRHG                 | 86 |
| SW2      | MGGKWSKRSLGGWPAVRERMRRTEPAAE-RIRQTEPAAEG--------VGAASQDLDRHG                 | 87 |
| SW8      | MGGKWSKRSLGGWPAVRERMRRTEP---------EPAAEG--------VGAASQDLDRHG                 | 88 |
| SW-23    | MGGKWSKCSMGGWPSVRERMRRTEP----------AAEG--------VGAASQDLDRHG                  | 89 |

120

|          |                                                                              |
|----------|------------------------------------------------------------------------------|
| ZANefcon | ALTSSNTAHNNADCAWLQAQEEEEVGFPVRPQVPLRPMTYKGAFDLSFFLKEKGGLEGL |
| rb28     | ALTTSNTARNNPDCAWLQAQEEEEVGFPVRPQVPLRPMTYKGAFDLSFFLKEKGGLEGL |
| gg5      | ALTSSNTATTNAACAWLEAQEEEGEVGFPVRPQVPLRPMTYKGAFDLGFFLKEKGGLEGL |
| Du151    | ALTSSNTAHNNPDCAWLQAQEEEPEVGFPVRPQVPLRPMTYKAAFDLSFFLKEKGGLEGL |
| rb12     | ALTSSNTAHNNADCAWLQAQEEEGEVGFPVRPQVPLRPMTYKGAFDLSFFLKEKGGLEGL |
| Du422    | ALTSSNTAHNNPDCAWLQAQEEEEVGFPVRPQVPLRPMTYKAAVDLSFFLKEKGGLEGL |
| Du123    | ALTSSNTAHTNADCAWLQAQEEEDEVGFPVRPQVPLRPMTYKAAFDLSFFLKEKGGLEGL |
| Du368    | ALTSSNTAHTNADCAWLQAQEEEDEVGFPVRPQVPLRPMTYKAAFDLSFFLKEKGGLEGL |
| Du467    | ALTTSNTAHNNPDCAWLQAQEEEEVGFPVTPQVPVRPMTYKAAFDLSFFLKEKGGLDGL |
| Du457    | ALTTSNTAHNNPDCAWLQAQEEEEVGFPVRPQVPLRPMTYKAAFDLSFFLKEKGGLEGL |
| Du258    | ALTTSNTAHTNADCAWLQAQEEEEVGFPVRPQVPLRPMTYKAAFDLSFFLKEKGGLDGL |
| Du179    | ALTSSNTAHNNPACAWLQAQEEDEVGFPVRPQVPLRPMTFKGAFDLSFFLKEKGGLDGL |
| SW-10    | ALTTSNTPHNNAACAWLQAQEEEEVGFPVRPQVPLRPMTYKGAFDLGFFLKEKGGLDGL |
| gg3      | ALTTSNTAQNNADCAWLQAQEEADEVGFPVRPQVPLRPMTYKAAFDLGFFLKEKGGLDGL |
| rb18     | ALTTSNTPTNNADCAWLQAQEDED-VGFPVRPQVPLRPMTYKAAVDLSFFLKEKGGLEGL |
| SW-7     | ALTSSNTPGNNADCAWLQAQEEEDVGFPVRPQVPLRPMTYKAAVDLSFFLKEKGGLEGL |
| CTSc2    | ALTSSNTPATNAACAQLEAQEEEEVGFPVRPQVPLRPMTFKGAFDLSFFLKEKGGLDGL |
| gg2      | ALTINNSGPTNAACAWLEAQEEDGEVGFPVRPQVPLRPMTFKGAFDLSFFLKEKGGLDGL |
| COT2     | ALTSSNTTSNNAACAWLEAQEEEGEVGFPVKPQVPVRPMTYKAALDLGFFLKEKGGLDGL |

```
COT6        ALTSSNTTSNNAACAWLEAQEEEGEVGFPVKPQVPVRPMTYKAALDLGFFLKEKGGLDGL
SW-15       ALTTSNTASNNADCAWLEAQEDE-EVGFPVKPQVPLRPMTYKGAFDLGFFLKEKGGLDGL
SW-5        ALTTSNTASNNADCAWLEAQEDE-EVGFPVKPQVPLRPMTYKGAFDLGFFLKEKG-TGWV
gg6         ALTTSNTASNNAACAWLEAQEEEGEVGFPVRPQVPLRPMTYKGAFDLSFFLKEKGGLDGL
SW-20       ALTSSNTAASNADCAWLEAQEEEEVGFPVRPQVPLRPMTYKAAFDLGFFLKEKGGLDGI
rb15        ALTSSNTAATNAACAWLEAQEEEEVGFPVRPQVPLRPMTYKGAVDLGFFLKEKGGLDGL
gg4         ALTTSNTATNNAACAWVEAQEEGEEVGFPVRPQVPLRPMTYKAAFDLSFFLKEKGGLEGL
rb13        ALTSSNTDANNATCAWLRAQEEEEVGFPVRPQVPLRPMTYKAAFDLSFFLKEKGGLEGL
rb21        ALTTSNTVSNNAAGAWLQAQEEEEVGFPVRPQVPLRPMTYKAAFDLSFFLKEKGGLDGL
SW9         ALTSSNTETTNATCAWLRAQEEDEEVGFPVKPQVPLRPMTYKAAFDLGFFLKEKGGLEGL
SW2         ALTSSNTETTNATCAWLRAQEEDEEVGFPVKPQVPLRPMTYKAAFDLGFFLKEKGGLDGL
SW8         ALTSSNTATNNATCAWLRAQEEEEEVGFQVKPQVPLRPMTYKAAFDLGFFLKEKGGLDGL
SW-23       ALTTSNTPTNNADCAWLQAQEEGEEVGFPVRPQVPLRPMTYKAAFDLSFFLKEKGGLEGL

180
ZANefcon    IYSK-----------KRQEILDLWVYHTQGFFPDWQNYTPGPGVRYPLTFGWCFKLVPV
rb28        IHSK-----------KRQDILDLWVYHTQGYFPDWQNYTPGPGVRYPLTFGWCFKLVPV
gg5         IYSK-----------KRQEILDLWVYHTQGFFPDWQNYTLGPGVRYPLTFGWPFKLVPV
Du151       IYSK-----------KRQDILDLWVYHTQGYFPDWQNYTPGPGVRLPLTFGWCFKLVPV
rb12        IWSK-----------KRQEILDLWVYHTQGYFPDWQNYTPGPGVRFPLTFGWCFKLVPV
Du422       IHSK-----------RRQDILDLWVYHTQGYFPDWQNYTPGPGVRFPLTFGWCFKLVPV
Du123       IWSK-----------RRQDILDLWVYNTQGYFPDWQNYTPGPGVRFPLTFGWCFKLVPV
Du368       IYSK-----------KRQEILDLWVYHTQGFFPDWQNYTPGPGVRYPLTFGWCFKLVPV
Du467       IHSK-----------KRQDILDLWVYHTQGYFPDWQNYTPGPGVRYPLTFGWCFKLVPV
Du457       IYSK-----------KRQEILDLWVYNTQGYFPDWQNYTPGPGVRYPLTFGWCFKLVPV
Du258       IYSK-----------KRQEILDLWVYHTQGFFPDWQNYTPGPGTRFPLTFGWCFKLVPV
Du179       IYSK-----------KRHDILDLWVYNTQGYFPDWQNYTPGPGIRYPLTFGWCFKLVPV
SW-10       IWSKEKGGLDGLIWSKKRQEILDLWVYNTQGYFPDWQNYTPGPGVRYPLTFGWCFKLVPV
gg3         IWSK-----------KRQEILDLWVYHTQGFFPDWQNYTPGPGVRFPLTFGWCFKLVPV
rb18        IYSK-----------KRQEILDLWVYHTQGYFPDWQNYTPGPGVRFPLTFGWCFKLVPV
SW-7        IHSK-----------QRQDILDLWVYNTQGYFPDWQNYTPGPGIRYPLTFGWCFKLVPV
CTSc2       IYSK-----------KRHEILDLWVYNTQGYFPDWQNYTPGPGVRYPLTFGWCYKLVPV
gg2         IYSK-----------KRQEILDLWVYHTQGFFPDWQNYTPGPGVRYPLTFGWCYKLVPV
COT2        IYSK-----------KRQEILDLWVYHTQGFFPDWQNYTPGPGVRYPLTFGWCFKLVPV
COT6        IYST-----------KRQEILDLWVYHTQGFFPDWQNYTSGPGVRYPLTFGWCYKLVPV
SW-15       IYSK-----------KRQEILDLWVYHTQGYFPDWQNYTSGPGIRYPLTFGWCYKLVPV
SW-5        NLLK-----------KRQEILDLWVYNTQGFFPDWQNYTPGPGVRYPLTFGWCYKLVPV
gg6         IYSK-----------KRQEILDLWVYNTQGYFPDWQNYTPGPGVRYPLTFGWCYKLVPV
SW-20       IYSK-----------KRQEILDLWVYHTQGFFPDWQNYTPGPGVRYPLTFGWPFKLVPV
rb15        IYSK-----------QRQDILDLWVYNTQGYFPDWQNYTPGPGVRYPLTFGWCYKLVPV
gg10        IYSK-----------KRQEILDLWVYHTQGYFPDWQNYTPGPGVRYPLTFGWCFKLVPV
gg4         IYSK-----------KRQEILDLWVYHTQGFFPDWQNYTPGPGIRYPLTFGWCFKLVPV
rb13        IYSK-----------RRQDILDLWVYNTQGFFPDWHNYTPGPGTRYPLTFGWCFKLVPV
rb21        IYSK-----------QRQDILDLWVYNTQGYFPDWQNYTPGPGVRYPLTFGWCYKLVPV
SW9         IYSK-----------KRQEILDLWVYNTQGFFPDWHNYTPGPGVRYPLTFGWCFKLVPV
SW2         IYSK-----------KRQEILDLWVYHTQGFFPDWQNYTPGPGVRYPLTFGWCFKLVPV
SW8         ISSK-----------KRQEILDLWVYNTQGYFPDWQNYTPGPGVRYPLTFGWCIQLVAV
SW-23       IHSK-----------KRQDILDLWVYQTQGFFPDWQNYTPGPGVRYPLTFGWCFKLVPV
                                                                         239
ZANefcon    DPREVEEANEGENNCLLHPMSQHGMEDEDREVLKWKFDSSLARRHMARELHPEYY-KDC
rb28        DPREVEEANEGEDNCLLHPMSQHGMEDAEREVLMWKFDSSLARRHMARELHPEYY-KDC
gg5         DPGEVEEANKGENNCLLHPISLHGMEDDHREVLKWKFDSQLARRHIARELHPEYY-KDC
Du151       DPEEVEEANKGENNCLLHPLSQHGMEDADREVLKWVFDSSLARRHLAREKHPEYY-KDC
rb12        DPSEVEEANKGENNCLLHPMSQHGMEDEDREVLKWVFDSSLARRHTAREKHPEFY-KDC
Du422       DPREVEEANKGENNCLLHPMSQHGIEDEEREVLQWMFDSSLARRHMAREKHPEFY-KDC
Du123       DPREVEEANKGENNCLLHPMSQHGIEDEDREVLKWEFDSSLARRHLAREIHPEYY-KDC
Du368       DPREVEEATKGEENCLLHPLNQHGMEDEEKEVLQWKFDSSLARRHLARELHPEYY-KDC
```

```
SW-7     DPREVEEANEGEDNCLLHPMSQHGADDADKEVLMWKFGSDLAYKHIAREIHSEYY-KDC
CTSc2    DPRKVEEANEGENNCLLHPMHQHGMDDEDREVLIWKFDSSLARRHMAREMHPEYY-KDC
gg2      DPGEVEEANKGENNCLLHPLSQHGMEDEDREVLKWQFDSSLARRHLARELHPEYY-KDC
COT2     DPEKVEEANEGENNNLLHPGSLHGMDDPQREVLQWRFDSRLAFHHVARELHPGSG-DDC
COT6     DPQEVEEANEGDNNCLLHPMSLHGMEDPHGEVLKWQFDSSLARRHLARELHPEYY-KDC
SW-15    DPSEVEEANKGEDNCLLHPMSQHGMEDEDREVLKWQFDSSLARRHVARELHPGVL-KDC
SW-5     DPKEVEEANKGENNCLLHPMSQHGMEDEEREILKWVFDSSLARRHIAREKHPEYY-KDC
gg6      DPKEVEEANEGENNCLLHPMSLHGMEDEDREVLKWQFDSLLARRHVARELHPEFY-KDC
SW-20    DPREVEEANNGENNCLLHPMSQHGMDDADREVLMWKFDSGLARRHMARE-YSEFY-KDC
rb15     DPREVEEANK-EDTRLLHPISQHGMEDADREVLKWQFDSSLARRHVARELYPEFY-KDC
gg10     DPKEVEEANEGEDNCLLHPMSLHGMEDSDGEVLMWKFDTQLARRHIARELHPEFY-KDC
gg4      DPDEVEEANKGENNCLLHPMSQHGMEDEDREVLQWKFDSALARRHMARELHPEFF-NN-
rb13     DPREVEEATEGDNNCLLHPMSQHGMEDEHKEVLQWKFDSLLARRHMARELHPEFY-KDC
rb21     DPREVEEANEGEDNCLLHPISQHGMEDPQRETLKWVFDSHLARRHMARELHPEYY-KDC
SW9      DPEEVEEATEGENNCLLHPINQHGMDDEDREVLKWKFDSMLARRHMARELHPEYY-KDC
SW2      DPAEVEENNKGEDSCLLHPISQHGMDDDDKEVLQWQFDSSLARIHLARELHPEYY-KDC
SW8      FQAYVEEVNEGENNCLLHPISQHGMEDEEREVLKWQFDSSLARRHVARELHPEYY-KDC
SW-23    DPGEVEEANKGEDNCLLHPMSQHGMEDGDREVLKWVFDSSLARRHLGPELHPEYY-KDC
```

Figure 23

```
                                                                     40
ZARevcon   MAGRSGDS-DEALLQAVRIIKILYQSNPYPKPEGTRQARK
RB18       MAGRSGDS-DKPLLQAVRIIKILYQSNPYPKPEGTRQARR
GG5        MAGRSGDS-DEALLQAVRIIKILYQSNPYPKPEGTRQARR
GG10       MAGRSGDS-DKPLLQAVRTIKILYQSNPYPKPEGTRQARR
Du179      MAGRSGDS-DEALLQAVRIIKILYQSNPYPKPEGTRQARR
Du156      MAGRSGDS-DEALLQVIRIIKILYQSSPYPNPEGTRQARK
Du151      MAGRSGDS-DEALLQAVRIIKILYQSNPYPKPEGSRQARK
Du422      MAGRSGDS-DEALLQAVKIIKILYQSNPYPKPEGTRQARK
DU281      MAGRSGDS-DEALLQAVRTIKILYQSSPYPKPEGTRQARK
RB28       MAGRSGDS-DEALLQAVRTIKILYQSNPYPKPGGTRQARK
CTSc2      MAGRSGDN-DEQLLQAVRIIKILYQSNPFPEPKGTRQARK
RB13       MAGRSGDS-DAELLQAVRIIKILYQSNPYPEPEGTRQARK
DU204      MAGRSGDSSDAALLQAVRIIKILYQSSPEPR--GTRQARK
Du368      MAGRSGDS-DEALLQAVRTIKILYQSSPYPKPEGTRQARK
Du123      MAGRSGDS-DEALLQAVRIIKILYQSSPYPKPEGTRQARK
RB27       MAGRSGDS-DEALLQAVRIVKILYQSNPYPKPEGTRQARK
RB21       MAGRSGDS-DEALLQAVRIIKILYQSNPYPKPEGTRQARK
RB12       MAGRSGDS-DEALLQAVRIIKILYQSNPYPKPEGTRQAQK 80
ZARevcon   NRRRRWRARQRQIHSISERILSTCLGRPAEPVPLQLPPIE
RB18       NRRRRWRARQRQINSISERILSTCLGRPTEPVPFQLPPIE
GG5        NRRRRWRARQRQIHSISERILSTCLGRPAEPVPLQLPPIE
GG10       NRRRRWRARQRQIHSIGERILSHCLGRPAEPVPLQLPPIE
Du179      NRRRRWRARQRQIRSISERILTTCLGRSAEPVPLQLPPIE
Du156      NQRRRWRARQRQIHSISERILSTCLGRSAEPVPLQLPPIE
Du151      NRRRRWRARQKQIHSISERILSTCLGRSAEPVPLRLPPIE
Du422      NRRRRWRARQRQIHSISERILSTCLGRSAEPVPLQLPPIE
DU281      NRRRRWRARQRQIHSISERILNACLGRPAEPVELQLPPLE
RB28       NRRRRWRARQRQIHSISQRILSDCLGRPAEPVPLQLPPIE
CTSc2      NRRRRWRARQRQINSISERILSDCLGRSAEPVPLQLPPIE
RB13       NRRRRWRARQRQINSISERILSTCLGRSAEPVPLQLPPIE
DU204      NRRRRWRARQKQIHSLRERILSNCLGRPAEPVPLQLPPIE
Du368      NRRRRWRARQRQIHSISERILSTCLGRPAEPVPLQLPPIE
Du123      NRRRRWRARQRQINSISERILSTCLGRPTEPVPLQLPPIE
RB27       NRRRRWRARQRQIHSISERILVTCLGRPTEPVPLQLPPIE
RB21       NRRRRWRARQRQIHSISERILSTVLGRPTEPVPLQLPPIE
RB12       NRRRRWRARQRQIHSISERILSTCLGRPAEPVPLQLPPIE 107
ZARevcon   RLHIDCSESSSTSGTQQSQDTTEGVGSP
RB18       RLCIDCSESGGTS-------TAEGVGST
GG5        RLNLGCDESSGTSGTQQPQGTTEGVGSP
GG10       RLHIDCSESSGTSGTQQSQGTTEGVGSP
Du179      RLHIDCSEDSGTSGTQQSQGTPEGVGSP
Du156      RLHIDCSESSGTSGTQQSQGTTEGVGSS
Du151      RLHIDCSESSGTSGTQQSQGTAERVGSP
Du422      RLHIDCSESSGTSGTQQSQGTAERVGSP
DU281      RLHIDCSENSGTSGTQQPQGTTERVGSP
RB28       RLHIDCSEDSGTSGTQQSQGTTERVGSP
CTSc2      RLHIGCSESGGTSGAQQSHGTTEGVGRP
RB13       RLHIGDSESGGTSGTQQPQGTTERVGNH
DU204      RLHIDCSENGGTSGTQQPQGTTEGVGSP
Du368      RLHIGDSESSGTSGTQQPQGTAEGLGSP
Du123      RLHIGCSESSGTSGTQQSQGTTERVGSP
RB27       RLHINCSESSGTSGTQQSQGTTEGVGNP
RB21       RLHINCSESSGTSGTQQSQGTTEGVGNP
RB12       RLCIDCSESSGTSGTQQSQGTTEGVGSC
```

Figure 24

| | | | | | | | | | | | | | | | | | | | |
|---|---|---|---|---|---|---|---|---|---|---|---|---|---|---|---|---|---|---|---|
| ZAtatcon | 100 | 90.492 | 89.356 | 87.031 | 91.612 | 88.202 | 89.356 | 94.871 | 94.535 | 93.391 | 91.612 | 94.871 | 91.612 | 90.492 | 94.871 | 88.202 | 79.288 | 86.289 |
| RB13 | 90.492 | 100 | 82.155 | 82.155 | 88.202 | 83.403 | 90.492 | 88.202 | 88.629 | 83.547 | 84.632 | 87.031 | 84.632 | 83.403 | 87.031 | 83.403 | 84.598 | 81.099 |
| Du151 | 89.356 | 82.155 | 100 | 85.841 | 90.492 | 80.886 | 80.886 | 84.632 | 86.13 | 87.39 | 91.612 | 91.612 | 83.403 | 87.031 | 88.202 | 84.632 | 71.596 | 79.288 |
| Du368 | 87.031 | 82.155 | 85.841 | 100 | 90.492 | 82.155 | 78.284 | 80.886 | 82.221 | 86.13 | 83.202 | 87.031 | 79.596 | 80.886 | 83.403 | 85.841 | 75.536 | 77.435 |
| Du123 | 91.612 | 88.202 | 90.492 | 90.492 | 100 | 87.031 | 84.632 | 85.841 | 87.39 | 88.629 | 89.356 | 92.714 | 82.155 | 85.841 | 88.202 | 90.492 | 75.536 | 79.288 |
| Du204 | 88.202 | 83.403 | 80.886 | 82.155 | 87.031 | 100 | 79.596 | 84.632 | 80.13 | 83.547 | 84.632 | 85.841 | 80.886 | 84.632 | 82.155 | 88.202 | 75.536 | 81.099 |
| CTSc2 | 89.356 | 90.492 | 80.886 | 78.284 | 84.632 | 79.596 | 100 | 87.031 | 92.229 | 83.547 | 85.841 | 85.841 | 83.403 | 82.155 | 88.202 | 82.155 | 84.598 | 86.289 |
| RB28 | 94.871 | 88.202 | 84.632 | 80.886 | 85.841 | 84.632 | 87.031 | 100 | 91.048 | 87.39 | 88.202 | 89.356 | 89.356 | 88.202 | 84.632 | 88.202 | 81.099 | 87.944 |
| GG2 | 94.535 | 88.629 | 86.13 | 82.221 | 87.39 | 86.13 | 92.229 | 91.048 | 100 | 92.229 | 92.229 | 91.048 | 88.629 | 87.39 | 87.39 | 84.632 | 77.093 | 84.908 |
| GG10 | 93.391 | 83.547 | 87.39 | 86.13 | 88.629 | 83.547 | 83.547 | 87.39 | 92.229 | 100 | 92.229 | 94.535 | 84.849 | 91.048 | 91.048 | 87.39 | 77.093 | 83.027 |
| Du422 | 91.612 | 84.632 | 91.612 | 88.202 | 89.356 | 84.632 | 85.841 | 88.202 | 92.229 | 92.229 | 100 | 93.801 | 87.031 | 90.492 | 89.356 | 87.39 | 77.435 | 82.868 |
| Du281 | 94.871 | 84.832 | 91.612 | 87.031 | 92.714 | 85.841 | 85.841 | 89.356 | 91.048 | 94.535 | 92.229 | 100 | 85.841 | 91.612 | 91.612 | 79.288 | 79.288 | 82.868 |
| Du179 | 91.612 | 84.632 | 83.403 | 79.596 | 82.155 | 85.841 | 83.403 | 89.356 | 88.629 | 84.849 | 91.048 | 85.841 | 100 | 80.356 | 80.356 | 91.612 | 71.596 | 84.598 |
| RB12 | 90.492 | 83.403 | 87.031 | 80.886 | 85.841 | 80.886 | 82.155 | 88.202 | 87.39 | 91.048 | 90.492 | 91.612 | 89.356 | 100 | 90.492 | 80.886 | 79.288 | 87.944 |
| GG4 | 94.871 | 87.031 | 88.202 | 83.403 | 88.202 | 84.632 | 86.202 | 90.492 | 91.048 | 92.229 | 89.356 | 91.612 | 89.356 | 90.492 | 100 | 84.632 | 81.099 | 86.289 |
| Du156 | 88.202 | 83.403 | 84.632 | 85.841 | 90.492 | 84.632 | 82.155 | 84.632 | 87.39 | 87.39 | 89.356 | 91.612 | 80.886 | 89.356 | 84.632 | 100 | 87.944 | 86.289 |
| Du285 | 79.288 | 84.598 | 71.596 | 75.536 | 75.536 | 84.598 | 82.155 | 81.099 | 77.093 | 77.093 | 77.435 | 79.288 | 71.596 | 79.288 | 81.099 | 87.944 | 100 | 82.868 |
| CTSc1 | 86.289 | 81.099 | 79.288 | 77.435 | 79.288 | 81.099 | 86.289 | 87.944 | 84.908 | 83.027 | 82.868 | 82.868 | 84.598 | 87.944 | 86.289 | 86.289 | 82.868 | 100 |

| | ZArevcon | RB18 | GG5 | GG10 | Du179 | Du156 | Du151 | Du422 | Du281 | RH2R | CTSc2 | RB13 | Du204 | Du368 | Du123 | RB27 | RB21 | RB12 |
|---|---|---|---|---|---|---|---|---|---|---|---|---|---|---|---|---|---|---|
| ZArevcon | 100 | 85.685 | 93.143 | 93.143 | 93.143 | 92.108 | 93.143 | 95.169 | 91.059 | 93.143 | 85.582 | 86.71 | 87.569 | 92.108 | 94.163 | 94.163 | 95.169 | 96.161 |
| RB18 | 85.685 | 100 | 83.217 | 85.685 | 83.217 | 78.033 | 80.668 | 83.217 | 78.033 | 79.362 | 79.362 | 81.953 | 76.122 | 79.362 | 85.685 | 81.953 | 83.217 | 85.685 |
| GG5 | 93.143 | 83.217 | 100 | 89.995 | 89.995 | 86.71 | 87.821 | 89.995 | 87.821 | 87.821 | 82.096 | 85.582 | 84.108 | 91.059 | 91.059 | 89.995 | 91.059 | 92.108 |
| GG10 | 93.143 | 85.685 | 89.995 | 100 | 89.995 | 88.916 | 87.821 | 89.995 | 88.916 | 88.916 | 82.096 | 83.276 | 85.279 | 88.916 | 88.916 | 88.916 | 89.995 | 91.059 |
| Du179 | 93.143 | 83.217 | 89.995 | 89.995 | 100 | 88.916 | 91.059 | 93.143 | 87.821 | 89.995 | 83.276 | 84.438 | 82.918 | 87.821 | 89.995 | 89.995 | 89.995 | 91.059 |
| Du156 | 92.108 | 78.033 | 86.71 | 88.916 | 88.916 | 100 | 88.916 | 91.059 | 86.71 | 86.71 | 84.438 | 84.108 | 84.108 | 88.916 | 91.059 | 87.821 | 88.916 | 91.059 |
| Du151 | 93.143 | 80.668 | 87.821 | 87.821 | 91.059 | 88.916 | 100 | 96.161 | 87.821 | 87.821 | 85.582 | 84.438 | 84.108 | 87.821 | 91.059 | 88.916 | 89.995 | 91.059 |
| Du422 | 95.169 | 83.217 | 89.995 | 89.995 | 93.143 | 91.059 | 96.161 | 100 | 89.995 | 92.108 | 84.438 | 85.582 | 84.108 | 88.916 | 93.143 | 91.059 | 92.108 | 93.143 |
| Du281 | 91.059 | 78.033 | 87.821 | 88.916 | 87.821 | 86.71 | 87.821 | 89.995 | 100 | 89.995 | 78.445 | 87.821 | 87.569 | 91.059 | 91.059 | 87.821 | 87.821 | 88.916 |
| RH2R | 93.143 | 79.362 | 87.821 | 87.821 | 89.995 | 86.71 | 87.821 | 92.108 | 89.995 | 100 | 83.276 | 83.276 | 85.279 | 86.71 | 91.059 | 88.916 | 89.995 | 91.059 |
| CTSc2 | 85.582 | 79.362 | 82.096 | 82.096 | 83.276 | 82.096 | 85.582 | 84.438 | 78.445 | 83.276 | 100 | 86.71 | 81.71 | 80.898 | 85.582 | 83.276 | 84.438 | 83.276 |
| RB13 | 86.71 | 81.953 | 85.582 | 83.276 | 83.276 | 84.438 | 84.438 | 85.582 | 87.821 | 83.276 | 86.71 | 100 | 84.108 | 86.71 | 88.916 | 85.582 | 86.71 | 85.582 |
| Du204 | 87.569 | 76.122 | 84.108 | 85.279 | 82.918 | 84.108 | 84.108 | 84.108 | 87.569 | 85.279 | 81.71 | 84.108 | 100 | 85.279 | 85.279 | 82.918 | 84.108 | 85.279 |
| Du368 | 92.108 | 79.362 | 91.059 | 88.916 | 87.821 | 88.916 | 87.821 | 88.916 | 91.059 | 86.71 | 80.898 | 86.71 | 85.279 | 100 | 92.108 | 88.916 | 92.108 | 89.995 |
| Du123 | 94.163 | 85.685 | 91.059 | 88.916 | 89.995 | 91.059 | 91.059 | 93.143 | 91.059 | 91.059 | 85.582 | 88.916 | 85.279 | 92.108 | 100 | 93.143 | 94.163 | 92.108 |
| RB27 | 94.163 | 81.953 | 89.995 | 88.916 | 89.995 | 87.821 | 88.916 | 91.059 | 87.821 | 88.916 | 83.276 | 85.582 | 82.918 | 88.916 | 93.143 | 100 | 97.14 | 92.108 |
| RB21 | 95.169 | 83.217 | 91.059 | 89.995 | 89.995 | 88.916 | 89.995 | 92.108 | 87.821 | 89.995 | 84.438 | 86.71 | 84.108 | 92.108 | 94.163 | 97.14 | 100 | 93.143 |
| RB12 | 96.161 | 85.685 | 92.108 | 91.059 | 91.059 | 91.059 | 91.059 | 93.143 | 88.916 | 91.059 | 83.276 | 85.582 | 85.279 | 92.108 | 92.108 | 92.108 | 93.143 | 100 |

```
FRAGMENT A                         FRAGMENT B                          FRAGMENT C

*          *          *
MEPIDPNLEPWNHPGSQPNTPCNKCYCKYCSYHCLV
                           **********    *          *
                           CKYCSYHCLVCFQTKGLGISYGRKKR                  Intron site
                                            **********      *          *          *          *          *
                                            LGISYGRKKRRQRRSTPPSSEDHQNPISKQPLPQTRGDPTGSEESKKKVESKTKTDPFD
```

Underline...mutations
Double underline...mutations used by others
Underline/bold...TAR binding site

Final version

```
X---------------------FRAGMENT C--------------------X-----FRAGMENT B--------X-------FRAGMENT A---------------x

*         *         *         *         *         *         *         *         *         *         *         *
LGISYGRKKRRQRRSTPPSSEDHQNPISKQPLPQTRGDPTGSEESKKKVESKTKTDPFDCKYCSYHCLVCFQTKGLGISYGRKKRMEPIDPNLEPWNHPGSQPNTPCNKCYCKYCSYHCLV
**********                                                 ***********    **********                                **********

Repeat2                                                    Repeat1        Repeat2                                   Repeat1
```

121 CODONS, 363 BASES

Figure 31

```
   1    AAGCTTGCCA CCATGGCTGC TCGCGCATCT ATCCTCAGAG GCGAAAAGTT GGATAAGTGG
  61    GAAAAAATCA GACTCAGGCC AGGAGGTAAA AAACACTACA TGCTGAAGCA TATCGTGTGG
 121    GCATCTAGGG AGTTGGAGAG ATTTGCACTG AACCCCGGAC TGCTGGAAAC CTCAGAGGGC
 181    TGTAAGCAAA TCATGAAACA GCTCCAACCA GCCTTGCAGA CCGGAACAGA AGAGCTGAAG
 241    TCCCTTTACA ATACCGTGGC AACCCTCTAT TGCGTCCACG AGAAGATCGA GGTGAGAGAC
 301    ACAAAGGAGG CCCTGGACAA AATCGAGGAG GAGCAGAATA AGTGCCAGCA GAAGACCCAG
 361    CAGGCAAAGG CTGCTGACGG AAAGGTCTCT CAGAACTATC CTATCGTTCA GAACCTTCAG
 421    GGGCAGATGG TGCACCAAGC AATCAGCCCT AGAACCCTGA ACGCATGGGT GAAGGTGATC
 481    GAGGAGAAAG CCTTTTCTCC CGAGGTTATC CCCATGTTTA CCGCCCTGAG CGAAGGCGCC
 541    ACTCCTCAAG ACCTGAACAC TATGCTGAAC ACAGTGGGAG GACACCAGGC CGCTATGCAG
 601    ATGTTGAAGG ATACCATCAA CGAGGAGGCA GCCGAATGGG ACCGCCTCCA CCCCGTGCAC
 661    GCCGGACCTA TCGCCCCCGG ACAAATGAGA GAACCTCGCG GAAGTGATAT TGCCGGTACT
 721    ACCAGCACCC TTCAAGAGCA GATTGCTTGG ATGACCAGCA ACCCACCCAT CCCAGTGGGC
 781    GATATTTACA AAAGGTGGAT TATTCTGGGG CTGAACAAAA TTGTGAGAAT GTACTCCCCC
 841    GTCTCCATCC TCGACATCCG CCAAGGACCC AAGGAGCCTT TTAGGGATTA CGTGGACAGA
 901    TTCTTCAAAA CCCTTAGAGC TGAGCAAGCC ACTCAGGAGG TTAAGAACTG GATGACAGAT
 961    ACTCTGCTCG TGCAAAACGC TAACCCCGAT TGCAAAACCA TCTTGAGAGC TCTCGGTCCA
1021    GGTGCCACCC TTGAGGAAAT GATGACAGCA TGTCAAGGCG TGGGAGGACC TGGGCACAAG
1031    GCCAGAGTTC TCGCTGAGGC CATGAGCCAG ACAAACTCAG GCAATATCAT GATGCAGAGG
1141    AGTAACTTTA AGGGTCCCAG GAGAATCGTC AAGTGCTTCA ATTGTGGCAA GGAGGGTCAC
1201    ATTGCCAGGA ACTGCCGCGC CCCCAGGAAG AAAGGCTGCT GCAAGTGTGG CAAAGAGGGC
1261    CACCAGATGA AGGATTGCAC CGAGCGCCAA GCAAACTTCC TGGGAAAGAT TTGGCCCAGT
1321    CATAAGGGCC GCCCTGGCGA ATTCTGCGGC AAGAAGGCCA TCGGCACCGT GCTGGTGGGC
1381    CCCACCCCCG TGAACATCAT CGGCCGGAAC ATGCTGACCC AGCTGGGCTG CACCCTGAAC
1441    TTCCCCATCA GCCCCATCGA GACCGTGCCC GTGAAGCTGA AGCCCGGCAT GGACGGCCCC
1501    AAGGTGAAGC AGTGGCCCCT GACCGAGGTG AAGATCAAGG CCCTGACCGC CATCTGCGAG
1561    GAGATGGAGA AGGAGGGCAA GATCACCAAG ATCGGCCCCG AGAACCCCTA CAACACCCCC
1621    ATCTTCGCCA TCAAGAAGGA GGACAGCACC AAGTGGCGGA AGCTGGTGGA CTTCCGGGAG
1681    CTGAACAAGC GGACCCAGGA CTTCTGGGAG GTGCAGCTGG GCATCCCCCA CCCCGCCGGC
1741    CTGAAGAAGA AGAAGAGCGT GACCGTGCTG GACGTGGGCG ACGCCTACTT CAGCGTGCCC
1801    CTGGACGAGG GCTTCCGGAA GTACACCGCC TTCACCATCC CCAGCATCAA CAACGAGACC
1861    CCCGGCATCC GGTACCAGTA CAACGTGCTG CCCCAGGGCT GGAAGGGCAG CCCCGCCATC
1921    TTCCAGGCCA GCATGACCAA GATCCTGGAG CCCTTCCGGG CCAAGAACCC CGAGATCGTG
1981    ATCTACCAGT ACATGGCCGC CCTGTACGTG GGCAGCGACC TGGAGATCGG CCAGCACCGG
2041    GCCAAGATCG AGGAGCTGCG GGAGCACCTG CTGAAGTGGG CTTCACCAC CCCCGACAAG
2101    AAGCACCAGA AGGAGCCCCC CTTCCTGTGG ATGGGCTACG AGCTGCACCC CGACAAGTGG
2161    ACCGTGCAGC CCATCCAGCT GCCCGAGAAG GACAGCTGGA CCGTGAACGA CATCCAGAAG
2221    CTGGTGGGCA AGCTGAACTG GACCAGCCAG ATCTACCCCG GCATCAAGGT GCGGCAGCTG
2281    TGCAAGCTGC TGCGGGGCAC CAAGGCCCTG ACCGACATCG TGCCCCTGAC CGAGGAGGCC
2341    GAGCTGGAGC TGGCCGAGAA CCGGCACATC CTGAAGGAGC CCGTGCACGG CGTGTACTAC
2401    GACCCCAGCA AGGACCTGAT CGCCGAGATC CAGAAGCAGG GCGACGACCA GTGGACCTAC
2461    CAGATCTACC AGGAGCCCTT CAAGAACCTG AAAACCGGCA AGTACGCCAA GCGGCGGACC
2521    ACCCACACCA ACGACGTGAA GCAGCTGACC GAGGCCGTGC AGAAGATCAG CCTGGAGAGC
2581    ATCGTGACCT GGGGCAAGAC CCCCAAGTTC CGGCTGCCCA TCCAGAAGGA GACCTGGGAG
2641    ATCTGGTGGA CCGACTACTG GCAGGCCACC TGGATCCCCG AGTGGGAGTT CGTGAACACC
2701    GGCCGCAAGC TTGCCACCAT GGTGGGCATC AGCTACGGCC GCAAGAAGCG CCGCCAGCGC
2761    CGCAGCACCC CGCCCAGCAG CGAGGACCAC CAGAACCCCA TCAGCAAGCA GCCCCTGCCC
2821    CAGACCCGCG CGACCCCAC CGGCAGCGAG GAGAGCAAGA AGAAGGTGGA GAGCAAGACC
2881    AAGACCGACC CCTTCGACTG CAAGTACTGC AGCTACCACT GTCTGGTGTG CTTCCAGACC
2941    AAGGGCCTGG GCATCTCCTA CGGGCGCAAG AAACGGATGG AGCCCATCGA CCCCAACCTG
3001    GAGCCCTGGA ACCACCCCGG CAGCCAGCCC AACACCCCCT GCAACAAGTG CTACTGCAAA
3061    TACTGCTCCT ACCACTGCCT CGTGGTGGGC TGGCCCGCCG TGCGCGAGCG CATCCGCCGC
3121    ACCGAGCCCG CCGCCGAGGG CGTGGGCCCC GCCAGCCAGG ACCTGGACAA CACGGCGCC
3181    CTGACCAGCA GCAACACCGC CCACAACAAC CCCGACTGCG CCTGGCTGCA GGCCCAGGAG
3241    GAGGAGGAGG ACGTGGGCTT CCCCGTGCGC CCCCAGGTGC CCTGCGCCC CATGACCTAC
3301    AAGGCCGCCT TCGACCTGAG CTTCTTCCTG AAGGAGAAGG GCGGCCTGGA GGGCCTGATC
3361    CACAGCAAGC GCCGCCAGGA CATCCTGGAC CTGTGGGTGT ACCACACCCA GGGCTACTTC
3421    CCCGACTGGC AGAACTACAC CCCCGGCCCC GGCGTGCGCT ACCCCCTGAC CTTCGGCTGG
3481    TGCTTCAAGC TGGTGCCCGT GGACCCCGCC GAGGTGGAGG AGGCCAACAA GGGCGAGAAC
3541    AACTGCCTGC TGCACCCCAT GAGCCAGCAC GGCATGGAGG ACGCCGACCG CGAGGTGCTG
3601    CGCTGGGTGT TCGACAGCAG CCTGGCCCGC CGCCACCTGG CCCGCGAGAA GCACCCCGAG
3661    TACTACAAGG ACTGAGAATT CTCTAGA
```

Figure 32a

| | | | | | |
|---|---|---|---|---|---|
| 1 | MLATMAARAS | ILRGEKLDKW | EKIRLRPGGK | KHYMLEHIVW | ASRELERFAL | NPGLLETSEG |
| 61 | CKQIMKQLQP | ALQTGTEELK | SLYNTVATLY | CVHEKIEVRD | TKEAADKIEE | EQNKCQQKTQ |
| 121 | QAKAADGKVS | QNYPIVQNLQ | GQMVHQAISP | RTLNAWVKVI | EEKAFSPEVI | PMFTALSEGA |
| 181 | TPQDLNTMLN | TVGGHQAAMQ | MLKDTINEEA | AEHDRLHPVH | AGPIAPGQMR | EPRGSDIAGT |
| 241 | TSTLQEQIAW | MTSNPPIPVG | DIYKRWIILG | LNKIVRMYSP | VSILDIRQGP | KEPFRDYVDR |
| 301 | FFKTLRAEQA | TQEVKNWMTD | TLLVQNANPD | CKTILRALGP | GATLEEMMTA | CQGVGGPGHK |
| 361 | ARVLAEAMSQ | TNSGNIMMQR | SNFKGPRRIV | KCFNCGKEGH | IARNCRAPRK | KGCWKCGKEG |
| 421 | HQMKDCTERQ | ANFLGKIWPS | HKGRPGEFCG | KKAIGTVLVG | PTPVNIIGRN | MLTQLGCTLN |
| 481 | FPISPIETVP | VKLKPGMDGP | KVKQWPLTEV | KIKALTAICE | EMEKEGKITK | IGPENPYNTP |
| 541 | IFAIKKEDST | KWRKLVDFRE | LNKRTQDFWE | VQLGIPHPAG | LKKKKSVTVL | DVGDAYFSVP |
| 601 | LDEGFRKYTA | FTIPSINNET | PGIRYQYNVL | PQGWKGSPAI | FQASMTKILE | PFRAKNPEIV |
| 661 | IYQYMAALYV | GSDLEIGQHR | AKIEELRSHL | LKWGFTTPDK | KHQKEPPFLW | MGYELHPDKW |
| 721 | TVQPIQLPEK | DSWTVNDIQK | LVGKLNWTSQ | IYPGIHVRQL | CKLLRGTKAL | TDIVPLTEEA |
| 781 | ELELAENREI | LKEPVHGVYY | DPSKDLIAEI | QKQGDDQWTY | QIYQEPFKNL | KTGKYARRRT |
| 841 | THTNDVKQLT | EAVQKISLES | IVTWGKTPKF | RLPIQKETWE | IWWTDYWQAT | WIPEWEFVNS |
| 901 | GRKLATMVGI | SYGRKKRRQR | RSTPPSSEDH | QNPISKQPLP | QTRGDPTGSE | ESKKVESKT |
| 961 | KTDPFDCKYC | SYHCLVCFQT | KGLGISYGRK | KRMEPIDPNL | EPWNHPGSQP | NTPCNKCYCK |
| 1021 | YCSYHCLVVQ | WPAVRERIRR | TIPAAEGVGP | ASQDLDKHGA | LTSSNTAHNN | PDCAWLQAQE |
| 1081 | EEEDVGFPVR | PQVPLRPMTY | KAAFDLSFFL | KEKGGLEGLI | HSKRRQDILD | LWVYHTQGYF |
| 1141 | PDWQNYTPGP | GVRYPLTFGW | CFKLVPVDPR | EVEEANKGEN | NCLLHPMSQH | GMEDADREVL |
| 1201 | RWVFDSSLAR | RHLAREKHPE | YYKU*EFBR | | | |

Bold= Restriction sites engineered

Bold Underlined= Kozac sequence and start ATG

Mutation to remove myristylation site of Gag (G6A) (Lee et al., 1994; Spearman et al., 1997)

Mutation to inactivate RT underlined (D666A, D687A) mutation (Chao S-F et al., 1995)

Start of shuffled Tat

Start of Truncated Nef

Figure 32b

```
ATGGCTGCTC GCGCATCTAT CCTCAGAGGC GAAAAGTTGG ATAAGTGGGA AAAAATCAGA¹
CTCAGGCCAG GAGGTAAAAA ACACTACATG CTGAAGCATA TCGTGTGGGC ATCTAGGGAG⁶¹
TTGGAGAGAT TTGCACTGAA CCCCGGACTG CTGGAAACCT CAGAGGGCTG TAAGCAAATC¹²¹
ATGAAACAGC TCCAACCAGC CTTGCAGACC GGAACAGAAG AGCTGAAGTC CCTTTACAAT¹⁸¹
ACCGTGGCAA CCCTCTATTG CGTCCACGAG AAGATCGAGG TGAGAGACAC AAAGGAGGCC²⁴¹
CTGGACAAAA TCGAGGAGGA GCAGAATAAG TGCCAGCAGA AGACCCAGCA GGCAAAGGCT³⁰¹
GCTGACGGAA AGGTCTCTCA GAACTATCCT ATCGTTCAGA ACCTTCAGGG GCAGATGGTG³⁶¹
CACCAAGCAA TCAGCCCTAG AACCCTGAAC GCATGGGTGA AGGTGATCGA GGAGAAAGCC⁴²¹
TTTTCTCCCG AGGTTATCCC CATGTTTACC GCCCTGAGCG AAGGCGCCAC TCCTCAAGAC⁴⁸¹
CTGAACACTA TGCTGAACAC AGTGGGAGGA CACCAGGCCG CTATGCAGAT GTTGAAGGAT⁵⁴¹
ACCATCAACG AGGAGGCAGC CGAATGGGAC CGCCTCCACC CCGTGCACGC CGGACCTATC⁶⁰¹
GCCCCCGGAC AAATGAGAGA ACCTCGCGGA AGTGATATTG CCGGTACTAC CAGCACCCTT⁶⁶¹
CAAGAGCAGA TTGCTTGGAT GACCAGCAAC CCACCCATCC CAGTGGGCGA TATTTACAAA⁷²¹
AGGTGGATTA TTCTGGGGCT GAACAAAATT GTGAGAATGT ACTCCCCCGT CTCCATCCTC⁷⁸¹
GACATCCGCC AAGGACCCAA GGAGCCTTTT AGGGATTACG TGGACAGATT CTTCAAAACC⁸⁴¹
CTTAGAGCTG AGCAAGCCAC TCAGGAGGTT AAGAACTGGA TGACAGATAC TCTGCTCGTG⁹⁰¹
CAAAACGCTA ACCCCGATTG CAAAACCATC TTGAGAGCTC TCGGTCCAGG TGCCACCCTT⁹⁶¹
GAGGAAATGA TGACAGCATG TCAAGGCGTG GGAGGACCTG GCACAAGGC CAGAGTTCTC¹⁰²¹
GCTGAGGCCA TGAGCCAGAC AAACTCAGGC AATATCATGA TGCAGAGGAG TAACTTTAAG¹⁰⁸¹
GGTCCCAGGA GAATCGTCAA GTGCTTCAAT TGTGGCAAGG AGGGTCACAT TGCCAGGAAC¹¹⁴¹
TGCCGCGCCC CCAGGAAGAA AGGCTGCTGG AAGTGTGGCA AGAGGGCCA CCAGATGAAG¹²⁰¹
GATTGCACCG AGCGCCAAGC AAACTTCCTG GGAAAGATTT GGCCCAGTCA TAAGGGCCGC¹²⁶¹
CCTGGC                                                           ¹³²¹
```

Figure 34

```
MAARASILRG EKLDKWEKIR LRPGGKKHYM LKHIVWASRE LERFALNPGL LETSEGCKQI¹
MKQLQPALQT GTEELKSLYN TVATLYCVHE KIEVRDTKEA LDKIEEEQNK CQQKTQQAKA⁶¹
ADGKVSQNYP IVQNLQGQMV HQAISPRTLN AWVKVIEEKA FSPEVIPMFT ALSEGATPQD¹²¹
LNTMLNTVGG HQAAMQMLKD TINEEAAEWD RLHPVHAGPI APGQMREPRG SDIAGTTSTL¹⁸¹
QEQIAWMTSN PPIPVGDIYK RWIILGLNKI VRMYSPVSIL DIRQGPKEPF RDYVDRFFKT²⁴¹
LRAEQATQEV KNWMTDTLLV QNANPDCKTI LRALGPGATL EEMMTACQGV GGPGHKARVL³⁰¹
AEAMSQTNSG NIMMQRSNFK GPRRIVKCFN CGKEGHIARN CRAPRKKGCW KCGKEGHQMK³⁶¹
DCTERQANFL GKIWPSHKGR PG                                         ⁴²¹
```

Figure 35

```
GGGAAAGATT TGGCCCAGTC ATAAGGGCCG CCCTGGCGAA TTCTGCGGCA AGAAGGCCAT¹
CGGCACCGTG CTGGTGGGCC CCACCCCCGT GAACATCATC GGCCGGAACA TGCTGACCCA⁶¹
GCTGGGCTGC ACCCTGAACT TCCCCATCAG CCCCATCGAG ACCGTGCCCG TGAAGCTGAA¹²¹
GCCCGGCATG GACGGCCCCA AGGTGAAGCA GTGGCCCCTG ACCGAGGTGA AGATCAAGGC¹⁸¹
CCTGACCGCC ATCTGCGAGG AGATGGAGAA GGAGGGCAAG ATCACCAAGA TCGGCCCCGA²⁴¹
GAACCCCTAC AACACCCCCA TCTTCGCCAT CAAGAAGGAG GACAGCACCA AGTGGCGGAA³⁰¹
GCTGGTGGAC TTCCGGGAGC TGAACAAGCG GACCCAGGAC TTCTGGGAGG TGCAGCTGGG³⁶¹
CATCCCCCAC CCCGCCGGCC TGAAGAAGAA GAAGAGCGTG ACCGTGCTGG ACGTGGGCGA⁴²¹
CGCCTACTTC AGCGTGCCCC TGGACGAGGG CTTCCGGAAG TACACCGCCT TCACCATCCC⁴⁸¹
CAGCATCAAC AACGAGACCC CCGGCATCCG GTACCAGTAC AACGTGCTGC CCCAGGGCTG⁵⁴¹
GAAGGGCAGC CCCGCCATCT TCCAGGCCAG CATGACCAAG ATCCTGGAGC CCTTCCGGGC⁶⁰¹
CAAGAACCCC GAGATCGTGA TCTACCAGTA CATGGCCGCC CTGTACGTGG GCAGCGACCT⁶⁶¹
GGAGATCGGC CAGCACCGGG CCAAGATCGA GGAGCTGCGG GAGCACCTGC TGAAGTGGGG⁷²¹
CTTCACCACC CCCGACAAGA AGCACCAGAA GGAGCCCCCC TTCCTGTGGA TGGGCTACGA⁷⁸¹
GCTGCACCCC GACAAGTGGA CCGTGCAGCC CATCCAGCTG CCCGAGAAGG ACAGCTGGAC⁸⁴¹
CGTGAACGAC ATCCAGAAGC TGGTGGGCAA GCTGAACTGG ACCAGCCAGA TCTACCCCGG⁹⁰¹
CATCAAGGTG CGGCAGCTGT GCAAGCTGCT GCGGGGCACC AAGGCCCTGA CCGACATCGT⁹⁶¹
GCCCCTGACC GAGGAGGCCG AGCTGGAGCT GGCCGAGAAC CGGGAGATCC TGAAGGAGCC¹⁰²¹
CGTGCACGGC GTGTACTACG ACCCCAGCAA GGACCTGATC GCCGAGATCC AGAAGCAGGG¹⁰⁸¹
CGACGACCAG TGGACCTACC AGATCTACCA GGAGCCCTTC AAGAACCTGA AAACCGGCAA¹¹⁴¹
GTACGCCAAG CGGCGGACCA CCCACACCAA CGACGTGAAG CAGCTGACCG AGGCCGTGCA¹²⁰¹
GAAGATCAGC CTGGAGAGCA TCGTGACCTG GGGCAAGACC CCCAAGTTCC GGCTGCCCAT¹²⁶¹
CCAGAAGGAG ACCTGGGAGA TCTGGTGGAC CGACTACTGG CAGGCCACCT GGATCCCCGA¹³²¹
GTGGGAGTTC GTGAACA
                                                            1381
```

Figure 36

```
CGKKAIGTVL VGPTPVNIIG RNMLTQLGCT LNFPISPIET VPVKLKPGMD GPKVKQWPLT¹
EVKIKALTAI CEEMEKEGKI TKIGPENPYN TPIFAIKKED STKWRKLVDF RELNKRTQDF⁶¹
WEVQLGIPHP AGLKKKKSVT VLDVGDAYFS VPLDEGFRKY TAFTIPSINN ETPGIRYQYN¹²¹
VLPQGWKGSP AIFQASMTKI LEPFRAKNPE IVIYQYMAAL YVGSDLEIGQ HRAKIEELRE¹⁸¹
HLLKWGFTTP DKHQKEPPF LWMGYELHPD KWTVQPIQLP EKDSWTVNDI QKLVGKLNWT²⁴¹
SQIYPGIKVR QLCKLLRGTK ALTDIVPLTE EAELELAENR EILKEPVHGV YYDPSKDLIA³⁰¹
EIQKQGDDQW TYQIYQEPFK NLKTGKYAKR RTTHTNDVKQ LTEAVQKISL ESIVTWGKTP³⁶¹
KFRLPIQKET WEIWWTDYWQ ATWIPEWEFV N
                                                            421
```

Figure 37

SEQUENCE LISTING

```
<160> NUMBER OF SEQ ID NOS: 111

<210> SEQ ID NO 1
<211> LENGTH: 306
<212> TYPE: DNA
<213> ORGANISM: Human immunodeficiency virus type 1

<400> SEQUENCE: 1
atggagccaa tagatcctaa cctagagccc tggaaccatc caggaagtca gcctaatact     60
ccttgtaata actgctattg taaacactgt agctaccatt gtctagtttg ctttcagaca    120
aaaggcttag gcatttccta tggcaggaag aagcggagac agcgacgaag cactcctcca    180
agcagtgaag atcatcaaaa tcctatatca aagcaaccct tatcccaaac ccgaggggac    240
```

```
ccgacaggct cggaagaatc gaagaagaag gtggagagca agacaaagac agatccattc    300
gattag                                                                306

<210> SEQ ID NO 2
<211> LENGTH: 101
<212> TYPE: PRT
<213> ORGANISM: Human immunodeficiency virus type 1

<400> SEQUENCE: 2

Met Glu Pro Ile Asp Pro Asn Leu Glu Pro Trp Asn His Pro Gly Ser
1               5                   10                  15

Gln Pro Asn Thr Pro Cys Asn Asn Cys Tyr Cys Lys His Cys Ser Tyr
                20                  25                  30

His Cys Leu Val Cys Phe Gln Thr Lys Gly Leu Gly Ile Ser Tyr Gly
            35                  40                  45

Arg Lys Lys Arg Arg Gln Arg Arg Ser Thr Pro Pro Ser Ser Glu Asp
        50                  55                  60

His Gln Asn Pro Ile Ser Lys Gln Pro Leu Ser Gln Thr Arg Gly Asp
65                  70                  75                  80

Pro Thr Gly Ser Glu Glu Ser Lys Lys Lys Val Glu Ser Lys Thr Lys
                85                  90                  95

Thr Asp Pro Phe Asp
            100

<210> SEQ ID NO 3
<211> LENGTH: 306
<212> TYPE: DNA
<213> ORGANISM: Human immunodeficiency virus type 1

<400> SEQUENCE: 3
atggagccaa tagatcctaa cctagagccc tggaaccatc caggaagtca acctaacact    60
ccttgtacta aatgctattg taaatactgc agctatcatt gtctagtttg ctttcagaca   120
aaaggcttag gcatttccta tggcaggaag aagcggagac agcgacgaag cactcctcca   180
agcagtgagg atcatcaaaa tcttatatca gagcagccct accccaagcc cgagggtc    240 ccgacaggct cggaagaatc gaagaagaag gtggagagca agacaaaaac agatccattc   300
gattag                                                                306

<210> SEQ ID NO 4
<211> LENGTH: 101
<212> TYPE: PRT
<213> ORGANISM: Human immunodeficiency virus type 1

<400> SEQUENCE: 4

Met Glu Pro Ile Asp Pro Asn Leu Glu Pro Trp Asn His Pro Gly Ser
1               5                   10                  15

Gln Pro Asn Thr Pro Cys Thr Lys Cys Tyr Cys Lys Tyr Cys Ser Tyr
                20                  25                  30

His Cys Leu Val Cys Phe Gln Thr Lys Gly Leu Gly Ile Ser Tyr Gly
            35                  40                  45

Arg Lys Lys Arg Arg Gln Arg Arg Ser Thr Pro Pro Ser Ser Glu Asp
        50                  55                  60

His Gln Asn Leu Ile Ser Glu Gln Pro Leu Pro Gln Ala Arg Gly Val
65                  70                  75                  80

Pro Thr Gly Ser Glu Glu Ser Lys Lys Lys Val Glu Ser Lys Thr Lys
                85                  90                  95
```

Thr Asp Pro Phe Asp
        100

<210> SEQ ID NO 5
<211> LENGTH: 618
<212> TYPE: DNA
<213> ORGANISM: Human immunodeficiency virus type 1

<400> SEQUENCE: 5

```
atgggggca   agtggtcaaa   aagcagcata   gtgggatggc   ctgctgtaag   agaaagaata    60
agaagaactg  agccagcagc   agagggagta   ggaccagcat   ctcaagactt   agataaacat   120
ggagcgctta  caagcagcaa   cacagcccac   aataatcctg   actgtgcctg   gctacaagca   180
caagaggagg  aagaagacgt   aggttttcca   gtcagacctc   aggtgcctct   aagaccaatg   240
acttataagg  cagcattcga   tctcagcttc   tttttaaaag   aaaaggggggg  actggaaggg   300
ttaattcact  ctaagagaag   acaagacatt   cttgatttgt   gggtctatca   cacacaaggc   360
tacttccctg  attggcaaaa   ctacacgccg   ggaccaggag   tcagataccc   actgaccttt   420
ggatggtgct  tcaagctagt   gccagttgat   ccaaggaag   tagaagaggc   caacaaagga   480
gaaaacaact  gtttgctaca   ccctatgagc   cagcatggaa   tggaggatgc   agacagagaa   540
gtattaagat  gggtgtttga   cagcagtcta   gcacgcagac   acctggcccg   cgagaaacat   600
ccggagtatt  acaaagac                                                          618
```

<210> SEQ ID NO 6
<211> LENGTH: 207
<212> TYPE: PRT
<213> ORGANISM: Human immunodeficiency virus type 1

<400> SEQUENCE: 6

Met Gly Gly Lys Trp Ser Lys Ser Ser Ile Val Gly Trp Pro Ala Val
1               5                   10                  15

Arg Glu Arg Ile Arg Arg Thr Glu Pro Ala Ala Glu Gly Val Gly Ala
            20                  25                  30

Ala Ser Gln Asp Leu Asp Lys His Gly Ala Leu Thr Ser Ser Asn Thr
        35                  40                  45

Ala His Asn Asn Pro Asp Cys Ala Trp Leu Gln Ala Gln Glu Glu Glu
    50                  55                  60

Pro Glu Val Gly Phe Pro Val Arg Pro Gln Val Pro Leu Arg Pro Met
65                  70                  75                  80

Thr Tyr Lys Ala Ala Phe Asp Leu Ser Phe Phe Leu Lys Glu Lys Gly
            85                  90                  95

Gly Leu Glu Gly Leu Ile Tyr Ser Lys Lys Arg Gln Asp Ile Leu Asp
            100                 105                 110

Leu Trp Val Tyr His Thr Gln Gly Tyr Phe Pro Asp Trp Gln Asn Tyr
        115                 120                 125

Thr Pro Gly Pro Gly Val Arg Leu Pro Leu Thr Phe Gly Trp Cys Phe
    130                 135                 140

Lys Leu Val Pro Val Asp Pro Glu Glu Val Glu Ala Asn Lys Gly
145                 150                 155                 160

Glu Asn Asn Cys Leu Leu His Pro Leu Ser Gln His Gly Met Glu Asp
            165                 170                 175

Ala Asp Arg Glu Val Leu Lys Trp Val Phe Asp Ser Ser Leu Ala Arg
        180                 185                 190

Arg His Leu Ala Arg Glu Lys His Pro Glu Tyr Tyr Lys Asp Cys

<210> SEQ ID NO 7
<211> LENGTH: 324
<212> TYPE: DNA
<213> ORGANISM: Human immunodeficiency virus type 1

<400> SEQUENCE: 7

```
atggcaggaa gaagcggaga cagcgacgaa gcactcctcc aagcagtgaa gatcatcaaa      60
atcctatatc aaagcaaccc ttatcccaaa cccgagggga cccgacaggc tcggaagaat     120
cgaagaagaa ggtggagagc aagacaaaga cagatccatt cgattagtga gcggattctt     180
agcacttgcc tgggacgatc tgcggagcct gtgcctcttc agctaccacc aattgagaga     240
cttcatattg actgcagcga gagcagcgga acttctggga cgcagcagtc tcaggggact     300
gcagagaggg tgggaagtcc ttaa                                            324
```

<210> SEQ ID NO 8
<211> LENGTH: 107
<212> TYPE: PRT
<213> ORGANISM: Human immunodeficiency virus type 1

<400> SEQUENCE: 8

```
Met Ala Gly Arg Ser Gly Asp Ser Asp Glu Ala Leu Leu Gln Ala Val
1               5                   10                  15
Lys Ile Ile Lys Ile Leu Tyr Gln Ser Asn Pro Tyr Pro Lys Pro Glu
            20                  25                  30
Gly Thr Arg Gln Ala Arg Lys Asn Arg Arg Arg Arg Trp Arg Ala Arg
        35                  40                  45
Gln Arg Gln Ile His Ser Ile Ser Glu Arg Ile Leu Ser Thr Cys Leu
    50                  55                  60
Gly Arg Ser Ala Glu Pro Val Pro Leu Gln Leu Pro Pro Ile Glu Arg
65                  70                  75                  80
Leu His Ile Asp Cys Ser Glu Ser Ser Gly Thr Ser Gly Thr Gln Gln
                85                  90                  95
Ser Gln Gly Thr Ala Glu Arg Val Gly Ser Pro
            100                 105
```

<210> SEQ ID NO 9
<211> LENGTH: 392
<212> TYPE: DNA
<213> ORGANISM: Human immunodeficiency virus type 1

<400> SEQUENCE: 9

```
ggatccgcgg ccgcaagctt gccaccatgg taggcatttc ctatggcagg aagaagcgga      60
gacagcgacg aagcactcct ccaagcagtg aggatcatca aaatcctata tcaaagcagc     120
ccttacccca acccgagggg gacccgacag gctcggaaga atcgaagaag aaggtggaga     180
gcaagacaaa aacagatcca ttcgattgta aatactgcag ctatcattgt ctagtttgct     240
ttcagacaaa aggcttaggt attagctatg gaaggaagaa acggatggag ccaatagatc     300
ctaacctaga gccctggaac catccaggaa gtcaacctaa cactccttgt aataaatgct     360
attgtaagta ctgttcatat cattgcctag tt                                   392
```

<210> SEQ ID NO 10
<211> LENGTH: 392
<212> TYPE: DNA
<213> ORGANISM: Human immunodeficiency virus type 1

-continued

<400> SEQUENCE: 10

```
ggatccgcgg ccgcaagctt gccaccatgg tgggcatcag ctacggccgc aagaagcgcc      60
gccagcgccg cagcaccccg cccagcagcg aggaccacca gaaccccatc agcaagcagc     120
ccctgcccca gacccgcggc gaccccaccg gcagcgagga gagcaagaag aaggtggaga     180
gcaagaccaa gaccgacccc ttcgactgca agtactgcag ctaccactgt ctggtgtgct     240
tccagaccaa gggcctgggc atctcctacg gcgcaagaa acggatggag cccatcgacc     300 caacctgga gccctggaac caccccggca gccagcccaa cacccccctgc aacaagtgct     360 actgcaaata ctgctcctac cactgcctcg tg                                   392
```

<210> SEQ ID NO 11
<211> LENGTH: 122
<212> TYPE: PRT
<213> ORGANISM: Human immunodeficiency virus type 1

<400> SEQUENCE: 11

```
Met Leu Gly Ile Ser Tyr Gly Arg Lys Lys Arg Arg Gln Arg Arg Ser
  1               5                  10                  15

Thr Pro Pro Ser Ser Glu Asp His Gln Asn Pro Ile Ser Lys Gln Pro
             20                  25                  30

Leu Pro Gln Thr Arg Gly Asp Pro Thr Gly Ser Glu Glu Ser Lys Lys
         35                  40                  45

Lys Val Glu Ser Lys Thr Lys Thr Asp Pro Phe Asp Cys Lys Tyr Cys
     50                  55                  60

Ser Tyr His Cys Leu Val Cys Phe Gln Thr Lys Gly Leu Gly Ile Ser
 65                  70                  75                  80

Tyr Gly Arg Lys Lys Arg Met Glu Pro Ile Asp Pro Asn Leu Glu Pro
                 85                  90                  95

Trp Asn His Pro Gly Ser Gln Pro Asn Thr Pro Cys Asn Lys Cys Tyr
            100                 105                 110

Cys Lys Tyr Cys Ser Tyr His Cys Leu Val
        115                 120
```

<210> SEQ ID NO 12
<211> LENGTH: 617
<212> TYPE: DNA
<213> ORGANISM: Human immunodeficiency virus type 1

<400> SEQUENCE: 12

```
gtgggatggc ctgctgtaag agaaagaata agaagaactg agccagcagc agagggagta      60
ggaccagcat ctcaagactt agataaacat ggagcgctta caagcagcaa cacagcccac     120
aataatcctg actgtgcctg gctacaagca caagaggagg aagaagacgt aggttttcca     180
gtcagacctc aggtgcctct aagaccaatg acttataagg cagcattcga tctcagcttc     240
tttttaaaag aaaaggggggg actggaaggg ttaattcact ctaagagaag acaagacatt     300
cttgatttgt gggtctatca cacacaaggc tacttccctg attggcaaaa ctacacgccg     360
ggaccaggag tcagataccc actgaccttt ggatggtgct tcaagctagt gccagttgat     420
ccaagggaag tagaagaggc caacaaagga gaaaacaact gtttgctaca ccctatgagc     480
cagcatggaa tggaggatgc agacagagaa gtattaagat gggtgtttga cagcagtcta     540
gcacgcagac acctggcccg cgagaaacat ccggagtatt acaaagacta ggaattctct     600
agagcggccg cgtcgac                                                    617
```

-continued

<210> SEQ ID NO 13
<211> LENGTH: 617
<212> TYPE: DNA
<213> ORGANISM: Human immunodeficiency virus type 1

<400> SEQUENCE: 13

```
gtgggctggc ccgccgtgcg cgagcgcatc cgccgcaccg agcccgccgc cgagggcgtg      60
ggccccgcca gccaggacct ggacaagcac ggcgccctga ccagcagcaa caccgcccac     120
aacaacccg actgcgcctg gctgcaggcc caggaggagg aggaggacgt gggcttcccc     180
gtgcgcccc aggtgcccct cgcccccatg acctacaagg ccgccttcga cctgagcttc     240
ttcctgaagg agaagggcgg cctggagggc ctgatccaca gcaagcgccg ccaggacatc     300
ctggacctgt gggtgtacca cacccagggc tacttccccg actggcagaa ctacaccccc     360
ggccccggcg tgcgctaccc cctgaccttc ggctggtgct tcaagctggt gcccgtggac     420
ccccgcgagg tggaggaggc caacaagggc gagaacaact gcctgctgca ccccatgagc     480
cagcacggca tggaggacgc cgaccgcgag gtgctgcgct gggtgttcga cagcagcctg     540
gcccgccgcc acctggcccg cgagaagcac cccgagtact acaaggactg agaattctct     600
agagcggccg cgtcgac                                                   617
```

<210> SEQ ID NO 14
<211> LENGTH: 196
<212> TYPE: PRT
<213> ORGANISM: Human immunodeficiency virus type 1

<400> SEQUENCE: 14

```
Val Gly Trp Pro Ala Val Arg Glu Arg Ile Arg Arg Thr Glu Pro Ala
1               5                  10                  15

Ala Glu Gly Val Gly Pro Ala Ser Gln Asp Leu Asp Lys His Gly Ala
            20                  25                  30

Leu Thr Ser Ser Asn Thr Ala His Asn Asn Pro Asp Cys Ala Trp Leu
        35                  40                  45

Gln Ala Gln Glu Glu Glu Asp Val Gly Phe Pro Val Arg Pro Gln
    50                  55                  60

Val Pro Leu Arg Pro Met Thr Tyr Lys Ala Ala Phe Asp Leu Ser Phe
65                  70                  75                  80

Phe Leu Lys Glu Lys Gly Gly Leu Glu Gly Leu Ile His Ser Lys Arg
                85                  90                  95

Arg Gln Asp Ile Leu Asp Leu Trp Val Tyr His Thr Gln Gly Tyr Phe
            100                 105                 110

Pro Asp Trp Gln Asn Tyr Thr Pro Gly Pro Gly Val Arg Tyr Pro Leu
        115                 120                 125

Thr Phe Gly Trp Cys Phe Lys Leu Val Pro Val Asp Pro Arg Glu Val
    130                 135                 140

Glu Glu Ala Asn Lys Gly Glu Asn Asn Cys Leu Leu His Pro Met Ser
145                 150                 155                 160

Gln His Gly Met Glu Asp Ala Asp Arg Glu Val Leu Arg Trp Val Phe
                165                 170                 175

Asp Ser Ser Leu Ala Arg Arg His Leu Ala Arg Glu Lys His Pro Glu
            180                 185                 190

Tyr Tyr Lys Asp
        195
```

<210> SEQ ID NO 15
<211> LENGTH: 1009

<212> TYPE: DNA
<213> ORGANISM: Human immunodeficiency virus type 1

<400> SEQUENCE: 15

```
ggatccgcgg ccgcaagctt gccaccatgg taggcatttc ctatggcagg aagaagcgga      60
gacagcgacg aagcactcct ccaagcagtg aggatcatca aaatcctata tcaaagcagc     120
ccttacccca aacccgaggg gacccgacag gctcggaaga tcgaagaag aaggtggaga      180
gcaagacaaa aacagatcca ttcgattgta aatactgcag ctatcattgt ctagtttgct     240
ttcagacaaa aggcttaggc atttcctatg caggaagaa gcggatggag ccaatagatc      300
ctaacctaga gccctggaac catccaggaa gtcaacctaa cactccttgt aataaatgct     360
attgtaaata ctgcagctat cattgtctag ttgtgggatg gcctgctgta agagaaagaa     420
taagaagaac tgagccagca gcagagggag taggaccagc atctcaagac ttagataaac     480
atggagcgct acaagcagc aacacagccc acaataatcc tgactgtgcc tggctacaag      540
cacaagagga ggaagaagac gtaggttttc cagtcagacc tcaggtgcct ctaagaccaa     600
tgacttataa ggcagcattc gatctcagct tctttttaaa agaaaagggg ggactggaag     660
ggttaattca ctctaagaga agacaagaca ttcttgattt gtgggtctat cacacacaag     720
gctacttccc tgattggcaa aactacacgc cgggaccagg agtcagatac ccactgacct     780
ttggatggtg cttcaagcta gtgccagttg atccaaggga agtagaagag gccaacaaag     840
gagaaaacaa ctgtttgcta caccctatga gccagcatgg aatggaggat gcagacagag     900
aagtattaag atgggtgttt gacagcagtc tagcacgcag acacctggcc cgcgagaaac     960
atccggagta ttacaaagac taggaattct ctagagcggc cgcgtcgac              1009
```

<210> SEQ ID NO 16
<211> LENGTH: 318
<212> TYPE: PRT
<213> ORGANISM: Human immunodeficiency virus type 1

<400> SEQUENCE: 16

```
Met Val Gly Ile Ser Tyr Gly Arg Lys Lys Arg Arg Gln Arg Arg Ser
1               5                   10                  15

Thr Pro Pro Ser Ser Glu Asp His Gln Asn Pro Ile Ser Lys Gln Pro
            20                  25                  30

Leu Pro Gln Thr Arg Gly Asp Pro Thr Gly Ser Glu Glu Ser Lys Lys
        35                  40                  45

Lys Val Glu Ser Lys Thr Lys Thr Asp Pro Phe Asp Cys Lys Tyr Cys
50                  55                  60

Ser Tyr His Cys Leu Val Cys Phe Gln Thr Lys Gly Leu Gly Ile Ser
65                  70                  75                  80

Tyr Gly Arg Lys Lys Arg Met Glu Pro Ile Asp Pro Asn Leu Glu Pro
                85                  90                  95

Trp Asn His Pro Gly Ser Gln Pro Asn Thr Pro Cys Asn Lys Cys Tyr
            100                 105                 110

Cys Lys Tyr Cys Ser Tyr His Cys Leu Val Val Gly Trp Pro Ala Val
        115                 120                 125

Arg Glu Arg Ile Arg Arg Thr Glu Pro Ala Ala Glu Gly Val Gly Pro
    130                 135                 140

Ala Ser Gln Asp Leu Asp Lys His Gly Ala Leu Thr Ser Ser Asn Thr
145                 150                 155                 160

Ala His Asn Asn Pro Asp Cys Ala Trp Leu Gln Ala Gln Glu Glu Glu
                165                 170                 175
```

```
Glu Asp Val Gly Phe Pro Val Arg Pro Gln Val Pro Leu Arg Pro Met
            180                 185                 190
Thr Tyr Lys Ala Ala Phe Asp Leu Ser Phe Phe Leu Lys Glu Lys Gly
        195                 200                 205
Gly Leu Glu Gly Leu Ile His Ser Lys Arg Arg Gln Asp Ile Leu Asp
        210                 215                 220
Leu Trp Val Tyr His Thr Gln Gly Tyr Phe Pro Asp Trp Gln Asn Tyr
225                 230                 235                 240
Thr Pro Gly Pro Gly Val Arg Tyr Pro Leu Thr Phe Gly Trp Cys Phe
                245                 250                 255
Lys Leu Val Pro Val Asp Pro Arg Glu Val Glu Glu Ala Asn Lys Gly
                260                 265                 270
Glu Asn Asn Cys Leu Leu His Pro Met Ser Gln His Gly Met Glu Asp
            275                 280                 285
Ala Asp Arg Glu Val Leu Arg Trp Val Phe Asp Ser Ser Leu Ala Arg
        290                 295                 300
Arg His Leu Ala Arg Glu Lys His Pro Glu Tyr Tyr Lys Asp
305                 310                 315
```

<210> SEQ ID NO 17
<211> LENGTH: 1009
<212> TYPE: DNA
<213> ORGANISM: Human immunodeficiency virus type 1

<400> SEQUENCE: 17

```
ggatccgcgg ccgcaagctt gccaccatgg tgggcatcag ctacggccgc aagaagcgcc      60
gccagcgccg cagcaccccg cccagcagcg aggaccacca gaaccccatc agcaagcagc     120
ccctgcccca gaccgcggc gaccccaccg gcagcgagga gagcaagaag aaggtggaga     180
gcaagaccaa gaccgacccc ttcgactgca agtactgcag ctaccactgt ctggtgtgct     240
tccagaccaa gggcctgggc atctcctacg gcgcaagaa acggatggag cccatcgacc     300
ccaacctgga gccctggaac acccccggca gccagcccaa cacccctgc aacaagtgct     360
actgcaaata ctgctcctac cactgcctcg tggtgggctg gccgccgtg cgcgagcgca     420
tccgccgcac cgagcccgcc gccgagggcg tgggccccgc cagccaggac ctggacaagc     480
acggcgccct gaccagcagc aacaccgccc acaacaaccc cgactgcgcc tggctgcagg     540
cccaggagga ggaggaggac gtgggcttcc ccgtgcgccc ccaggtgccc ctgcgcccca     600
tgacctacaa ggccgccttc gacctgagct tcttcctgaa ggagaagggc ggcctggagg     660
gcctgatcca cagcaagcgc cgccaggaca tcctggacct gtgggtgtac cacacccagg     720
gctacttccc cgactggcag aactacaccc ccggccccgg cgtgcgctac cccctgacct     780
tcggctggtg cttcaagctg gtgcccgtgg accccgcga ggtggaggag gccaacaagg     840
gcgagaacaa ctgcctgctg cacccccatga gccagcacgg catggaggac gccgaccgcg     900
aggtgctgcg ctgggtgttc gacagcagcc tggcccgccg ccacctggcc cgcgagaagc     960
acccgagta ctacaaggac tgagaattct ctagagcggc cgcgtcgac                 1009
```

<210> SEQ ID NO 18
<211> LENGTH: 101
<212> TYPE: PRT
<213> ORGANISM: Human immunodeficiency virus type 1

<400> SEQUENCE: 18

Met Glu Pro Val Asp Pro Asn Leu Glu Pro Trp Asn His Pro Gly Ser

-continued

```
              1               5                  10                 15
Gln Pro Lys Thr Ala Cys Asn Lys Cys Tyr Cys Lys His Cys Ser Tyr
                    20                 25                 30

His Cys Leu Val Cys Phe Gln Thr Lys Gly Leu Gly Ile Ser Tyr Gly
                    35                 40                 45

Arg Lys Lys Arg Arg Gln Arg Arg Ser Ala Pro Pro Ser Ser Glu Asp
                    50                 55                 60

His Gln Asn Leu Ile Ser Lys Gln Pro Leu Pro Gln Thr Arg Gly Asp
65                             70                 75                 80

Pro Thr Gly Ser Glu Glu Ser Lys Lys Lys Val Glu Ser Lys Thr Glu
                    85                 90                 95

Thr Asp Pro Phe Asp
              100
```

<210> SEQ ID NO 19
<211> LENGTH: 207
<212> TYPE: PRT
<213> ORGANISM: Human immunodeficiency virus type 1

<400> SEQUENCE: 19

```
Met Gly Gly Lys Trp Ser Lys Ser Ser Ile Val Gly Trp Pro Ala Val
1               5                  10                 15

Arg Glu Arg Ile Arg Arg Thr Glu Pro Ala Ala Glu Gly Val Gly Ala
                    20                 25                 30

Ala Ser Gln Asp Leu Asp Lys His Gly Ala Leu Thr Ser Ser Asn Thr
                    35                 40                 45

Ala His Asn Asn Ala Asp Cys Ala Trp Leu Gln Ala Gln Glu Glu Glu
                    50                 55                 60

Glu Glu Val Gly Phe Pro Val Arg Pro Gln Val Pro Leu Arg Pro Met
65                             70                 75                 80

Thr Tyr Lys Gly Ala Phe Asp Leu Ser Phe Phe Leu Lys Glu Lys Gly
                    85                 90                 95

Gly Leu Glu Gly Leu Ile Tyr Ser Lys Lys Arg Gln Glu Ile Leu Asp
                    100                105                110

Leu Trp Val Tyr His Thr Gln Gly Phe Phe Pro Asp Trp Gln Asn Tyr
                    115                120                125

Thr Pro Gly Pro Gly Val Arg Tyr Pro Leu Thr Phe Gly Trp Cys Phe
                    130                135                140

Lys Leu Val Pro Val Asp Pro Arg Glu Val Glu Glu Ala Asn Glu Gly
145                            150                155                160

Glu Asn Asn Cys Leu Leu His Pro Met Ser Gln His Gly Met Glu Asp
                    165                170                175

Glu Asp Arg Glu Val Leu Lys Trp Lys Phe Asp Ser Ser Leu Ala Arg
                    180                185                190

Arg His Met Ala Arg Glu Leu His Pro Glu Tyr Tyr Lys Asp Cys
                    195                200                205
```

<210> SEQ ID NO 20
<211> LENGTH: 107
<212> TYPE: PRT
<213> ORGANISM: Human immunodeficiency virus type 1

<400> SEQUENCE: 20

```
Met Ala Gly Arg Ser Gly Asp Ser Asp Glu Ala Leu Leu Gln Ala Val
1               5                  10                 15

Arg Ile Ile Lys Ile Leu Tyr Gln Ser Asn Pro Tyr Pro Lys Pro Glu
```

```
            20                  25                  30
Gly Thr Arg Gln Ala Arg Lys Asn Arg Arg Arg Trp Arg Ala Arg
        35                  40                  45

Arg Gln Arg Gln Ile His Ser Ile Ser Glu Arg Ile Leu Ser Thr Cys Leu
50                  55                  60

Gly Arg Pro Ala Glu Pro Val Pro Leu Gln Leu Pro Pro Ile Glu Arg
65                  70                  75                  80

Leu His Ile Asp Cys Ser Glu Ser Ser Gly Thr Ser Gly Thr Gln Gln
                    85                  90                  95

Ser Gln Gln Thr Thr Glu Gly Val Gly Ser Pro
            100                 105
```

<210> SEQ ID NO 21
<211> LENGTH: 20
<212> TYPE: DNA
<213> ORGANISM: Human immunodeficiency virus type 1

<400> SEQUENCE: 21
ggccgcagag ggaaccatac                                           20

<210> SEQ ID NO 22
<211> LENGTH: 21
<212> TYPE: DNA
<213> ORGANISM: Human immunodeficiency virus type 1

<400> SEQUENCE: 22
gccctgtctt attcttctag g                                         21

<210> SEQ ID NO 23
<211> LENGTH: 21
<212> TYPE: DNA
<213> ORGANISM: Human immunodeficiency virus type 1

<400> SEQUENCE: 23
cctcaatatc cccatcactc t                                         21

<210> SEQ ID NO 24
<211> LENGTH: 20
<212> TYPE: DNA
<213> ORGANISM: Human immunodeficiency virus type 1

<400> SEQUENCE: 24
tgccagcata gcagaatagg                                           20

<210> SEQ ID NO 25
<211> LENGTH: 24
<212> TYPE: DNA
<213> ORGANISM: Human immunodeficiency virus type 1

<400> SEQUENCE: 25
ctatcaatgc tcctactcct aatc                                      24

<210> SEQ ID NO 26
<211> LENGTH: 21
<212> TYPE: DNA
<213> ORGANISM: Human immunodeficiency virus type 1

<400> SEQUENCE: 26
gatagtagga ggcttgatag g                                         21

<210> SEQ ID NO 27

```
<211> LENGTH: 18
<212> TYPE: DNA
<213> ORGANISM: Human immunodeficiency virus type 1

<400> SEQUENCE: 27
ggtgtactcg ctatagtg                                                      18

<210> SEQ ID NO 28
<211> LENGTH: 20
<212> TYPE: DNA
<213> ORGANISM: Human immunodeficiency virus type 1

<400> SEQUENCE: 28
ccttcagcta ctgctattgc                                                    20

<210> SEQ ID NO 29
<211> LENGTH: 3687
<212> TYPE: DNA
<213> ORGANISM: Human immunodeficiency virus type 1

<400> SEQUENCE: 29
aagcttgcca ccatggctgc tcgcgcatct atcctcagag gcgaaaagtt ggataagtgg        60
gaaaaaatca gactcaggcc aggaggtaaa aaacactaca tgctgaagca tatcgtgtgg       120
gcatctaggg agttggagag atttgcactg aaccccggac tgctgaaaac ctcagagggc       180
tgtaagcaaa tcatgaaaca gctccaacca gccttgcaga ccggaacaga agagctgaag       240 tcccttaca ataccgtggc aaccctctat gcgtccacg agaagatcga ggtgagagac         300
acaaaggagg ccctggacaa atcgaggag gagcagaata agtgccagca aagacccag         360 caggcaaagg ctgctgacgg aaaggtctct cagaactatc ctatcgttca gaaccttcag       420
gggcagatgg tgcaccaagc aatcagccct agaaccctga cgcatgggt gaaggtgatc        480 gaggagaaag cctttttctcc cgaggttatc cccatgttta ccgccctgag cgaaggcgcc      540
actcctcaag acctgaacac tatgctgaac acagtgggag acaccaggc cgctatgcag        600 atgttgaagg ataccatcaa cgaggaggca gccgaatggg accgcctcca ccccgtgcac       660
gccggaccta tcgcccccgg acaaatgaga gaacctcgcg gaagtgatat tgccggtact       720
accagcaccc ttcaagagca gattgcttgg atgaccagca cccaccccat cccagtgggc      780
gatatttaca aaggtggat tattctgggg ctgaacaaaa ttgtgagaat gtactccccc        840
gtctccatcc tcgacatccg ccaaggaccc aaggagcctt taggggatta cgtggacaga       900
ttcttcaaaa cccttagagc tgagcaagcc actcaggagg ttaagaactg gatgacagat       960
actctgctcg tgcaaaacgc taaccccgat tgcaaaacca tcttgagagc tctcggtcca      1020
ggtgccaccc ttgaggaaat gatgacagca tgtcaaggcg tgggaggacc tgggcacaag      1080
gccagagttc tcgctgaggc catgagccag acaaactcag gcaatatcat gatgcagagg      1140
agtaacttta gggtccccag agaatcgtc aagtgcttca attgtggcaa ggagggtcac       1200
attgccagga actgccgcgc ccccaggaag aaaggctgct ggaagtgtgg caaagagggc      1260
caccagatga aggattgcac cgagcgccaa gcaaacttcc tgggaaagat ttggcccagt      1320
cataagggcc gcctggcga attctgcggc aagaaggcca tcggcaccgt gctggtgggc       1380
cccacccccg tgaacatcat cggccggaac atgctgaccc agctgggctg caccctgaac      1440
ttccccatca gccccatcga ccgtgccc gtgaagctga gcccggcat ggacggcccc         1500 aaggtgaagc agtggcccct gaccgaggtg aagatcaagg ccctgaccgc catctgcgag      1560
gagatggaga aggagggcaa gatcaccaag atcggccccg agaaccccta caacacccc       1620
```

-continued

```
atcttcgcca tcaagaagga ggacagcacc aagtggcgga agctggtgga cttccgggag    1680
ctgaacaagc ggacccagga cttctgggag gtgcagctgg gcatccccca ccccgccggc    1740
ctgaagaaga agaagagcgt gaccgtgctg gacgtgggcg acgcctactt cagcgtgccc    1800
ctggacgagg gcttccggaa gtacaccgcc ttcaccatcc ccagcatcaa caacgagacc    1860
cccggcatcc ggtaccagta caacgtgctg ccccagggct ggaagggcag ccccgccatc    1920
ttccaggcca gcatgaccaa gatcctggag cccttccggg ccaagaaccc cgagatcgtg    1980
atctaccagt acatggccgc cctgtacgtg ggcagcgacc tggagatcgg ccagcaccgg    2040
gccaagatcg aggagctgcg ggagcacctg ctgaagtggg gcttccaccac ccccgacaag    2100
aagcaccaga aggagccccc cttcctgtgg atgggctacg agctgcaccc cgacaagtgg    2160
accgtgcagc ccatccagct gcccgagaag gacagctgga ccgtgaacga catccagaag    2220
ctggtgggca gctgaactg gaccagccag atctaccccg gcatcaaggt gcggcagctg    2280
tgcaagctgc tgcggggcac caaggccctg accgacatcg tgccctgac cgaggaggcc    2340
gagctggagc tggccgagaa ccgggagatc ctgaaggagc ccgtgcacgg cgtgtactac    2400
gaccccagca aggacctgat cgccgagatc cagaagcagg gcgacgacca gtggacctac    2460
cagatctacc aggagccctt caagaacctg aaaaccggca agtacgccaa gcggcggacc    2520
acccacacca cgacgtgaa gcagctgacc gaggccgtgc agaagatcag cctggagagc    2580
atcgtgacct ggggcaagac ccccaagttc cggctgccca tccagaagga gacctgggag    2640
atctggtgga ccgactactg gcaggccacc tggatccccg agtgggagtt cgtgaacagc    2700
ggccgcaagc ttgccaccat ggtgggcatc agctacggcc gcaagaagcg ccgccagcgc    2760
cgcagcaccc cgcccagcag cgaggaccac cagaacccca tcagcaagca gccctgccc    2820
cagacccgcg gcgaccccac cggcagcgag gagagcaaga gaaggtgga gagcaagacc    2880
aagaccgacc ccttcgactg caagtactgc agctaccact gtctggtgtg cttccagacc    2940
aagggcctgg gcatctccta cgggcgcaag aaacggatgg agcccatcga ccccaacctg    3000
gagccctgga accaccccgg cagccagccc aacaccccct gcaacaagtg ctactgcaaa    3060
tactgctcct accactgcct cgtggtgggc tggcccgccg tgcgcgagcg catccgccgc    3120
accgagcccg ccgccgaggg cgtgggcccc gccagccagg acctggacaa gcacggcgcc    3180
ctgaccagca gcaacaccgc ccacaacaac cccgactgcg cctggctgca ggcccaggag    3240
gaggaggagg acgtgggctt ccccgtgcgc ccccaggtgc cctgcgccc catgacctac    3300
aaggccgcct tcgacctgag cttcttcctg aaggagaagg gcggcctgga gggcctgatc    3360
cacagcaagc gccgccagga catcctggac ctgtgggtgt accacaccca gggctacttc    3420
cccgactggc agaactacac ccccggcccc ggcgtgcgct accccctgac cttcggctgg    3480
tgcttcaagc tggtgcccgt ggaccccgc gaggtggagg aggccaacaa gggcgagaac    3540
aactgcctgc tgcaccccat gagccagcac ggcatggagg acgccgaccg cgaggtgctg    3600
cgctgggtgt tcgacagcag cctggcccgc cgccacctgg cccgcgagaa gcaccccgag    3660
tactacaagg actgagaatt ctctaga                                        3687
```

<210> SEQ ID NO 30
<211> LENGTH: 1228
<212> TYPE: PRT
<213> ORGANISM: Human immunodeficiency virus type 1

<400> SEQUENCE: 30

-continued

```
Lys Leu Ala Thr Met Ala Ala Arg Ala Ser Ile Leu Arg Gly Glu Lys
1               5                   10                  15
Leu Asp Lys Trp Glu Lys Ile Arg Leu Arg Pro Gly Gly Lys Lys His
            20                  25                  30
Tyr Met Leu Lys His Ile Val Trp Ala Ser Arg Glu Leu Glu Arg Phe
                35                  40                  45
Ala Leu Asn Pro Gly Leu Leu Glu Thr Ser Glu Gly Cys Lys Gln Ile
    50                  55                  60
Met Lys Gln Leu Gln Pro Ala Leu Gln Thr Gly Thr Glu Glu Leu Lys
65                  70                  75                  80
Ser Leu Tyr Asn Thr Val Ala Thr Leu Tyr Cys Val His Glu Lys Ile
                85                  90                  95
Glu Val Arg Asp Thr Lys Glu Ala Leu Asp Lys Ile Glu Glu Glu Gln
            100                 105                 110
Asn Lys Cys Gln Gln Lys Thr Gln Gln Ala Lys Ala Ala Asp Gly Lys
    115                 120                 125
Val Ser Gln Asn Tyr Pro Ile Val Gln Asn Leu Gln Gly Gln Met Val
    130                 135                 140
His Gln Ala Ile Ser Pro Arg Thr Leu Asn Ala Trp Val Lys Val Ile
145                 150                 155                 160
Glu Glu Lys Ala Phe Ser Pro Glu Val Ile Pro Met Phe Thr Ala Leu
                165                 170                 175
Ser Glu Gly Ala Thr Pro Gln Asp Leu Asn Thr Met Leu Asn Thr Val
            180                 185                 190
Gly Gly His Gln Ala Ala Met Gln Met Leu Lys Asp Thr Ile Asn Glu
        195                 200                 205
Glu Ala Ala Glu Trp Asp Arg Leu His Pro Val His Ala Gly Pro Ile
210                 215                 220
Ala Pro Gly Gln Met Arg Glu Pro Arg Gly Ser Asp Ile Ala Gly Thr
225                 230                 235                 240
Thr Ser Thr Leu Gln Glu Gln Ile Ala Trp Met Thr Ser Asn Pro Pro
                245                 250                 255
Ile Pro Val Gly Asp Ile Tyr Lys Arg Trp Ile Ile Leu Gly Leu Asn
            260                 265                 270
Lys Ile Val Arg Met Tyr Ser Pro Val Ser Ile Leu Asp Ile Arg Gln
        275                 280                 285
Gly Pro Lys Glu Pro Phe Arg Asp Tyr Val Asp Arg Phe Phe Lys Thr
    290                 295                 300
Leu Arg Ala Glu Gln Ala Thr Gln Glu Val Lys Asn Trp Met Thr Asp
305                 310                 315                 320
Thr Leu Leu Val Gln Asn Ala Asn Pro Asp Cys Lys Thr Ile Leu Arg
                325                 330                 335
Ala Leu Gly Pro Gly Ala Thr Leu Glu Glu Met Met Thr Ala Cys Gln
            340                 345                 350
Gly Val Gly Gly Pro Gly His Lys Ala Arg Val Leu Ala Glu Ala Met
        355                 360                 365
Ser Gln Thr Asn Ser Gly Asn Ile Met Met Gln Arg Ser Asn Phe Lys
    370                 375                 380
Gly Pro Arg Arg Ile Val Lys Cys Phe Asn Cys Gly Lys Glu Gly His
385                 390                 395                 400
Ile Ala Arg Asn Cys Arg Ala Pro Arg Lys Lys Gly Cys Trp Lys Cys
                405                 410                 415
Gly Lys Glu Gly His Gln Met Lys Asp Cys Thr Glu Arg Gln Ala Asn
```

-continued

```
            420             425             430
Phe Leu Gly Lys Ile Trp Pro Ser His Lys Gly Arg Pro Gly Glu Phe
            435             440             445
Cys Gly Lys Lys Ala Ile Gly Thr Val Leu Val Gly Pro Thr Pro Val
450             455             460
Asn Ile Ile Gly Arg Asn Met Leu Thr Gln Leu Gly Cys Thr Leu Asn
465             470             475             480
Phe Pro Ile Ser Pro Ile Glu Thr Val Pro Val Lys Leu Lys Pro Gly
                485             490             495
Met Asp Gly Pro Lys Val Lys Gln Trp Pro Leu Thr Glu Val Lys Ile
            500             505             510
Lys Ala Leu Thr Ala Ile Cys Glu Glu Met Glu Lys Glu Gly Lys Ile
            515             520             525
Thr Lys Ile Gly Pro Glu Asn Pro Tyr Asn Thr Pro Ile Phe Ala Ile
            530             535             540
Lys Lys Glu Asp Ser Thr Lys Trp Arg Lys Leu Val Asp Phe Arg Glu
545             550             555             560
Leu Asn Lys Arg Thr Gln Asp Phe Trp Glu Val Gln Leu Gly Ile Pro
                565             570             575
His Pro Ala Gly Leu Lys Lys Lys Ser Val Thr Val Leu Asp Val
            580             585             590
Gly Asp Ala Tyr Phe Ser Val Pro Leu Asp Glu Gly Phe Arg Lys Tyr
            595             600             605
Thr Ala Phe Thr Ile Pro Ser Ile Asn Asn Glu Thr Pro Gly Ile Arg
            610             615             620
Tyr Gln Tyr Asn Val Leu Pro Gln Gly Trp Lys Gly Ser Pro Ala Ile
625             630             635             640
Phe Gln Ala Ser Met Thr Lys Ile Leu Glu Pro Phe Arg Ala Lys Asn
                645             650             655
Pro Glu Ile Val Ile Tyr Gln Tyr Met Ala Ala Leu Tyr Val Gly Ser
            660             665             670
Asp Leu Glu Ile Gly Gln His Arg Ala Lys Ile Glu Glu Leu Arg Glu
            675             680             685
His Leu Leu Lys Trp Gly Phe Thr Thr Pro Asp Lys Lys His Gln Lys
            690             695             700
Glu Pro Pro Phe Leu Trp Met Gly Tyr Glu Leu His Pro Asp Lys Trp
705             710             715             720
Thr Val Gln Pro Ile Gln Leu Pro Glu Lys Asp Ser Trp Thr Val Asn
                725             730             735
Asp Ile Gln Lys Leu Val Gly Lys Leu Asn Trp Thr Ser Gln Ile Tyr
            740             745             750
Pro Gly Ile Lys Val Arg Gln Leu Cys Lys Leu Leu Arg Gly Thr Lys
            755             760             765
Ala Leu Thr Asp Ile Val Pro Leu Thr Glu Glu Ala Glu Leu Glu Leu
            770             775             780
Ala Glu Asn Arg Glu Ile Leu Lys Glu Pro Val His Gly Val Tyr Tyr
785             790             795             800
Asp Pro Ser Lys Asp Leu Ile Ala Glu Ile Gln Lys Gln Gly Asp Asp
                805             810             815
Gln Trp Thr Tyr Gln Ile Tyr Gln Glu Pro Phe Lys Asn Leu Lys Thr
            820             825             830
Gly Lys Tyr Ala Lys Arg Arg Thr Thr His Thr Asn Asp Val Lys Gln
            835             840             845
```

-continued

```
Leu Thr Glu Ala Val Gln Lys Ile Ser Leu Glu Ser Ile Val Thr Trp
    850                 855                 860
Gly Lys Thr Pro Lys Phe Arg Leu Pro Ile Gln Lys Glu Thr Trp Glu
865                 870                 875                 880
Ile Trp Trp Thr Asp Tyr Trp Gln Ala Thr Trp Ile Pro Glu Trp Glu
                885                 890                 895
Phe Val Asn Ser Gly Arg Lys Leu Ala Thr Met Val Gly Ile Ser Tyr
                900                 905                 910
Gly Arg Lys Lys Arg Gln Arg Arg Ser Thr Pro Pro Ser Ser Glu
            915                 920                 925
Asp His Gln Asn Pro Ile Ser Lys Gln Pro Leu Pro Gln Thr Arg Gly
    930                 935                 940
Asp Pro Thr Gly Ser Glu Ser Lys Lys Val Glu Ser Lys Thr
945                 950                 955                 960
Lys Thr Asp Pro Phe Asp Cys Lys Tyr Cys Ser Tyr His Cys Leu Val
                965                 970                 975
Cys Phe Gln Thr Lys Gly Leu Gly Ile Ser Tyr Gly Arg Lys Lys Arg
                980                 985                 990
Met Glu Pro Ile Asp Pro Asn Leu Glu Pro Trp Asn His Pro Gly Ser
        995                 1000                1005
Gln Pro Asn Thr Pro Cys Asn Lys Cys Tyr Cys Lys Tyr Cys Ser
    1010                1015                1020
Tyr His Cys Leu Val Val Gly Trp Pro Ala Val Arg Glu Arg Ile
    1025                1030                1035
Arg Arg Thr Glu Pro Ala Ala Glu Gly Val Gly Pro Ala Ser Gln
    1040                1045                1050
Asp Leu Asp Lys His Gly Ala Leu Thr Ser Ser Asn Thr Ala His
    1055                1060                1065
Asn Asn Pro Asp Cys Ala Trp Leu Gln Ala Gln Glu Glu Glu
    1070                1075                1080
Asp Val Gly Phe Pro Val Arg Pro Gln Val Pro Leu Arg Pro Met
    1085                1090                1095
Thr Tyr Lys Ala Ala Phe Asp Leu Ser Phe Phe Leu Lys Glu Lys
    1100                1105                1110
Gly Gly Leu Glu Gly Leu Ile His Ser Lys Arg Arg Gln Asp Ile
    1115                1120                1125
Leu Asp Leu Trp Val Tyr His Thr Gln Gly Tyr Phe Pro Asp Trp
    1130                1135                1140
Gln Asn Tyr Thr Pro Gly Pro Gly Val Arg Tyr Pro Leu Thr Phe
    1145                1150                1155
Gly Trp Cys Phe Lys Leu Val Pro Val Asp Pro Arg Glu Val Glu
    1160                1165                1170
Glu Ala Asn Lys Gly Glu Asn Asn Cys Leu Leu His Pro Met Ser
    1175                1180                1185
Gln His Gly Met Glu Asp Ala Asp Arg Glu Val Leu Arg Trp Val
    1190                1195                1200
Phe Asp Ser Ser Leu Ala Arg Arg His Leu Ala Arg Glu Lys His
    1205                1210                1215
Pro Glu Tyr Tyr Lys Asp Glu Phe Ser Arg
    1220                1225

<210> SEQ ID NO 31
<211> LENGTH: 1326
```

<212> TYPE: DNA
<213> ORGANISM: Human immunodeficiency virus type 1

<400> SEQUENCE: 31

```
atggctgctc gcgcatctat cctcagaggc gaaaagttgg ataagtggga aaaaatcaga      60
ctcaggccag gaggtaaaaa acactacatg ctgaagcata tcgtgtgggc atctagggag     120
ttggagagat ttgcactgaa ccccggactg ctggaaacct cagagggctg taagcaaatc     180
atgaaacagc tccaaccagc cttgcagacc ggaacagaag agctgaagtc cctttacaat     240
accgtggcaa ccctctattg cgtccacgag aagatcgagg tgagagacac aaaggaggcc     300
ctggacaaaa tcgaggagga gcagaataag tgccagcaga agacccagca ggcaaaggct     360
gctgacggaa aggtctctca gaactatcct atcgttcaga accttcaggg gcagatggtg     420
caccaagcaa tcagccctag aaccctgaac gcatgggtga aggtgatcga ggagaaagcc     480
ttttctcccg aggttatccc catgtttacc gccctgagcg aaggcgccac tcctcaagac     540
ctgaacacta tgctgaacac agtgggagga caccaggccg ctatgcagat gttgaaggat     600
accatcaacg aggaggcagc cgaatgggac cgcctccacc ccgtgcacgc cggacctatc     660
gcccccggac aaatgagaga acctcgcgga agtgatattg ccggtactac cagcacccctt    720
caagagcaga ttgcttggat gaccagcaac ccacccatcc cagtgggcga tatttacaaa     780
aggtggatta ttctggggct gaacaaaatt gtgagaatgt actcccccgt ctccatcctc     840
gacatccgcc aaggacccaa ggagcctttt agggattacg tggacagatt cttcaaaacc     900
cttagagctg agcaagccac tcaggaggtt aagaactgga tgacagatac tctgctcgtg     960
caaaacgcta accccgattg caaaaccatc ttgagagctc tcggtccagg tgccacccctt   1020
gaggaaatga tgacagcatg tcaaggcgtg ggaggacctg gcacaaggc cagagttctc    1080
gctgaggcca tgagccagac aaactcaggc aatatcatga tgcagaggag taactttaag   1140
ggtcccagga gaatcgtcaa gtgcttcaat tgtggcaagg agggtcacat tgccaggaac   1200
tgccgcgccc ccaggaagaa aggctgctgg aagtgtggca agagggccca ccagatgaag   1260
gattgcaccg agcgccaagc aaacttcctg ggaaagattt ggcccagtca aagggccgc    1320
cctggc                                                               1326
```

<210> SEQ ID NO 32
<211> LENGTH: 442
<212> TYPE: PRT
<213> ORGANISM: Human immunodeficiency virus type 1

<400> SEQUENCE: 32

```
Met Ala Ala Arg Ala Ser Ile Leu Arg Gly Glu Lys Leu Asp Lys Trp
  1               5                  10                  15

Glu Lys Ile Arg Leu Arg Pro Gly Gly Lys Lys His Tyr Met Leu Lys
             20                  25                  30

His Ile Val Trp Ala Ser Arg Glu Leu Glu Arg Phe Ala Leu Asn Pro
         35                  40                  45

Gly Leu Leu Glu Thr Ser Glu Gly Cys Lys Gln Ile Met Lys Gln Leu
     50                  55                  60

Gln Pro Ala Leu Gln Thr Gly Thr Glu Glu Leu Lys Ser Leu Tyr Asn
 65                  70                  75                  80

Thr Val Ala Thr Leu Tyr Cys Val His Glu Lys Ile Glu Val Arg Asp
                 85                  90                  95

Thr Lys Glu Ala Leu Asp Lys Ile Glu Glu Glu Gln Asn Lys Cys Gln
            100                 105                 110
```

Gln Lys Thr Gln Gln Ala Lys Ala Ala Asp Gly Lys Val Ser Gln Asn
            115                 120                 125

Tyr Pro Ile Val Gln Asn Leu Gln Gly Gln Met Val His Gln Ala Ile
        130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Ile Ala Pro Gly Gln
210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Val Ser Ile Leu Asp Ile Arg Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Glu Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Gly His Lys Ala Arg Val Leu Ala Glu Ala Met Ser Gln Thr Asn
        355                 360                 365

Ser Gly Asn Ile Met Met Gln Arg Ser Asn Phe Lys Gly Pro Arg Arg
    370                 375                 380

Ile Val Lys Cys Phe Asn Cys Gly Lys Glu Gly His Ile Ala Arg Asn
385                 390                 395                 400

Cys Arg Ala Pro Arg Lys Lys Gly Cys Trp Lys Cys Gly Lys Glu Gly
                405                 410                 415

His Gln Met Lys Asp Cys Thr Glu Arg Gln Ala Asn Phe Leu Gly Lys
            420                 425                 430

Ile Trp Pro Ser His Lys Gly Arg Pro Gly
        435                 440

<210> SEQ ID NO 33
<211> LENGTH: 1397
<212> TYPE: DNA
<213> ORGANISM: Human immunodeficiency virus type 1

<400> SEQUENCE: 33
gggaaagatt tggcccagtc ataagggccg ccctggcgaa ttctgcggca agaaggccat    60
cggcaccgtg ctggtgggcc caccccccgt gaacatcatc ggccggaaca tgctgaccca   120
gctgggctgc accctgaact tccccatcag ccccatcgag accgtgcccg tgaagctgaa   180
gcccggcatg gacggcccca aggtgaagca gtggcccctg accgaggtga agatcaaggc   240

-continued

```
cctgaccgcc atctgcgagg agatggagaa ggagggcaag atcaccaaga tcggccccga    300
gaacccctac aacacccca tcttcgccat caagaaggag acagcacca agtggcggaa     360
gctggtggac ttccgggagc tgaacaagcg acccaggac ttctgggagg tgcagctggg    420
catcccccac cccgccggcc tgaagaagaa gaagagcgtg accgtgctgg acgtgggcga    480
cgcctacttc agcgtgcccc tggacgaggg cttccggaag tacaccgcct tcaccatccc    540
cagcatcaac aacgagaccc ccggcatccg gtaccagtac aacgtgctgc cccagggctg    600
gaagggcagc cccgccatct tccaggccag catgaccaag atcctggagc ccttccgggc    660
caagaacccc gagatcgtga tctaccagta catggccgcc ctgtacgtgg gcagcgacct    720
ggagatcggc cagcaccggg ccaagatcga ggagctgcgg gagcacctgc tgaagtgggg    780
cttcaccacc cccgacaaga agcaccagaa ggagcccccc ttcctgtgga tgggctacga    840
gctgcacccc gacaagtgga ccgtgcagcc catccagctg cccgagaagg acagctggac    900
cgtgaacgac atccagaagc tggtgggcaa gctgaactgg accagccaga tctaccccgg   960
catcaaggtg cggcagctgt gcaagctgct gcggggcacc aaggccctga ccgacatcgt   1020
gcccctgacc gaggaggccg agctggagct ggccgagaac cgggagatcc tgaaggagcc   1080
cgtgcacggc gtgtactacg accccagcaa ggacctgatc gccgagatcc agaagcaggg   1140
cgacgaccag tggacctacc agatctacca ggagcccttc aagaacctga aaaccggcaa   1200
gtacgccaag cggcggacca cccacaccaa cgacgtgaag cagctgaccg aggccgtgca   1260
gaagatcagc ctggagagca tcgtgacctg gggcaagacc cccaagttcc ggctgcccat   1320
ccagaaggag acctgggaga tctggtggac cgactactgg caggccacct ggatccccga   1380
gtgggagttc gtgaaca                                                    1397
```

<210> SEQ ID NO 34
<211> LENGTH: 451
<212> TYPE: PRT
<213> ORGANISM: Human immunodeficiency virus type 1

<400> SEQUENCE: 34

```
Cys Gly Lys Lys Ala Ile Gly Thr Val Leu Val Gly Pro Thr Pro Val
1               5                   10                  15

Asn Ile Ile Gly Arg Asn Met Leu Thr Gln Leu Gly Cys Thr Leu Asn
            20                  25                  30

Phe Pro Ile Ser Pro Ile Glu Thr Val Pro Val Lys Leu Lys Pro Gly
        35                  40                  45

Met Asp Gly Pro Lys Val Lys Gln Trp Pro Leu Thr Glu Val Lys Ile
    50                  55                  60

Lys Ala Leu Thr Ala Ile Cys Glu Glu Met Glu Lys Glu Gly Lys Ile
65                  70                  75                  80

Thr Lys Ile Gly Pro Glu Asn Pro Tyr Asn Thr Pro Ile Phe Ala Ile
                85                  90                  95

Lys Lys Glu Asp Ser Thr Lys Trp Arg Lys Leu Val Asp Phe Arg Glu
            100                 105                 110

Leu Asn Lys Arg Thr Gln Asp Phe Trp Glu Val Gln Leu Gly Ile Pro
        115                 120                 125

His Pro Ala Gly Leu Lys Lys Lys Ser Val Thr Val Leu Asp Val
    130                 135                 140

Gly Asp Ala Tyr Phe Ser Val Pro Leu Asp Glu Gly Phe Arg Lys Tyr
145                 150                 155                 160
```

```
Thr Ala Phe Thr Ile Pro Ser Ile Asn Asn Glu Thr Pro Gly Ile Arg
            165                 170                 175

Tyr Gln Tyr Asn Val Leu Pro Gln Gly Trp Lys Gly Ser Pro Ala Ile
            180                 185                 190

Phe Gln Ala Ser Met Thr Lys Ile Leu Glu Pro Phe Arg Ala Lys Asn
            195                 200                 205

Pro Glu Ile Val Ile Tyr Gln Tyr Met Ala Ala Leu Tyr Val Gly Ser
            210                 215                 220

Asp Leu Glu Ile Gly Gln His Arg Ala Lys Ile Glu Glu Leu Arg Glu
225                 230                 235                 240

His Leu Leu Lys Trp Gly Phe Thr Thr Pro Asp Lys Lys His Gln Lys
                245                 250                 255

Glu Pro Pro Phe Leu Trp Met Gly Tyr Glu Leu His Pro Asp Lys Trp
            260                 265                 270

Thr Val Gln Pro Ile Gln Leu Pro Glu Lys Asp Ser Trp Thr Val Asn
            275                 280                 285

Asp Ile Gln Lys Leu Val Gly Lys Leu Asn Trp Thr Ser Gln Ile Tyr
            290                 295                 300

Pro Gly Ile Lys Val Arg Gln Leu Cys Lys Leu Leu Arg Gly Thr Lys
305                 310                 315                 320

Ala Leu Thr Asp Ile Val Pro Leu Thr Glu Glu Ala Glu Leu Glu Leu
                325                 330                 335

Ala Glu Asn Arg Glu Ile Leu Lys Glu Pro Val His Gly Val Tyr Tyr
            340                 345                 350

Asp Pro Ser Lys Asp Leu Ile Ala Glu Ile Gln Lys Gln Gly Asp Asp
            355                 360                 365

Gln Trp Thr Tyr Gln Ile Tyr Gln Glu Pro Phe Lys Asn Leu Lys Thr
            370                 375                 380

Gly Lys Tyr Ala Lys Arg Arg Thr Thr His Thr Asn Asp Val Lys Gln
385                 390                 395                 400

Leu Thr Glu Ala Val Gln Lys Ile Ser Leu Glu Ser Ile Val Thr Trp
                405                 410                 415

Gly Lys Thr Pro Lys Phe Arg Leu Pro Ile Gln Lys Glu Thr Trp Glu
            420                 425                 430

Ile Trp Trp Thr Asp Tyr Trp Gln Ala Thr Trp Ile Pro Glu Trp Glu
            435                 440                 445

Phe Val Asn
    450

<210> SEQ ID NO 35
<211> LENGTH: 1479
<212> TYPE: DNA
<213> ORGANISM: Human immunodeficiency virus type 1

<400> SEQUENCE: 35
atgggtgcga gagcgtcaat attaagaggg gaaaaattag ataaatggga aaaaattagg      60
ttaaggccag ggggaaagaa acattatatg ttaaaacaca tagtatgggc aagcagggag     120
ctggaaagat ttgcacttaa ccctggcctt ttagaaacat cagaaggatg taaacaaata     180
atgaaacagc tacaaccagc tctccagaca ggaacagagg aacttaaatc attatacaac     240
acagtagcaa ctctctattg tgtacatgaa aagatagaag tacgagacac caaggaagcc     300
ttagataaga tagaggaaga acaaaacaaa tgtcagcaaa aaacgcagca ggcaaaagcg     360
gctgacggga aagtcagtca aaattatcct atagtgcaga atctccaagg gcaaatggta     420
```

```
catcaagcca tatcacctag aaccttgaat gcatgggtaa aagtaataga agaaaaggct    480
tttagcccag aggtaatacc catgtttaca gcattatcag aaggagccac cccacaagat    540
ttaaacacca tgttaaatac agtggggggga catcaagcag ccatgcaaat gttaaaagat    600
actattaatg aagaggctgc agaatgggat agagtacatc cagtccatgc ggggcctatt    660
gcaccaggcc agatgagaga accaggggga agtgacatag caggaactac tagtacccct    720
caggaacaaa tagcatggat gacaagtaac ccacctattc cagtgggaga catctataaa    780
agatggataa ttctggggtt aaataaaata gtgagaatgt atagccccggt cagcattttg    840 gacataagac aaggggccaaa ggaacccttt cgagactatg tagatcggtt ctttaaaact    900
ttaagagctg aacaagctac acaagaagta aaaaattgga tgacagacac cttgttagtc    960
caaaatgcga acccagattg taagaccatt ttgagagcat taggaccagg ggctacatta   1020
gaagaaatga tgacagcatg tcaaggggtg ggaggacctg gtcacaaagc aagagtattg   1080
gctgaggcaa tgagtcaagc aaacagtgga aacataatga tgcagagaag caattttaaa   1140
ggccctagaa gaattgttaa atgttttaac tgtggcaagg aagggcacat agccagaaat   1200
tgcagagccc ctaggaaaaa aggctgttgg aaatgtggaa aggaaggaca ccaaatgaaa   1260
gactgtactg aaaggcaggc taattttttta gggaaaattt ggccttccca caggggagg   1320 ccagggaatt tccttcagaa cagaccagag ccaacagccc caccagcaga gagcttcagg   1380
ttcgaagaga caacccccgc tccgaaacag gagccgatag aaagggaacc cttaacttcc   1440
ctcaaatcac tctttggcag cgaccccttg tctcaataa                          1479
```

<210> SEQ ID NO 36
<211> LENGTH: 492
<212> TYPE: PRT
<213> ORGANISM: Human immunodeficiency virus type 1

<400> SEQUENCE: 36

```
Met Gly Ala Arg Ala Ser Ile Leu Arg Gly Glu Lys Leu Asp Lys Trp
1               5                   10                  15

Glu Lys Ile Arg Leu Arg Pro Gly Gly Lys Lys His Tyr Met Leu Lys
            20                  25                  30

His Ile Val Trp Ala Ser Arg Glu Leu Glu Arg Phe Ala Leu Asn Pro
        35                  40                  45

Gly Leu Leu Glu Thr Ser Glu Gly Cys Lys Gln Ile Met Lys Gln Leu
    50                  55                  60

Gln Pro Ala Leu Gln Thr Gly Thr Glu Glu Leu Lys Ser Leu Tyr Asn
65                  70                  75                  80

Thr Val Ala Thr Leu Tyr Cys Val His Glu Lys Ile Glu Val Arg Asp
                85                  90                  95

Thr Lys Glu Ala Leu Asp Lys Ile Glu Glu Glu Gln Asn Lys Cys Gln
            100                 105                 110

Gln Lys Thr Gln Gln Ala Lys Ala Ala Asp Gly Lys Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190
```

Ala Ala Met Gln Met Leu Lys Asp Thr Ile Asn Glu Glu Ala Ala Glu
        195                 200                 205

Trp Asp Arg Val His Pro Val His Ala Gly Pro Ile Ala Pro Gly Gln
210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Val Ser Ile Leu Asp Ile Arg Gln Gly Pro Lys Glu
        275                 280                 285

Pro Phe Arg Asp Tyr Val Asp Arg Phe Phe Lys Thr Leu Arg Ala Glu
290                 295                 300

Gln Ala Thr Gln Glu Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Gly His Lys Ala Arg Val Leu Ala Glu Ala Met Ser Gln Ala Asn
        355                 360                 365

Ser Gly Asn Ile Met Met Gln Arg Ser Asn Phe Lys Gly Pro Arg Arg
370                 375                 380

Ile Val Lys Cys Phe Asn Cys Gly Lys Glu Gly His Ile Ala Arg Asn
385                 390                 395                 400

Cys Arg Ala Pro Arg Lys Lys Gly Cys Trp Lys Cys Gly Lys Glu Gly
                405                 410                 415

His Gln Met Lys Asp Cys Thr Glu Arg Gln Ala Asn Phe Leu Gly Lys
            420                 425                 430

Ile Trp Pro Ser His Lys Gly Arg Pro Gly Asn Phe Leu Gln Asn Arg
        435                 440                 445

Pro Glu Pro Thr Ala Pro Pro Ala Glu Ser Phe Arg Phe Glu Glu Thr
450                 455                 460

Thr Pro Ala Pro Lys Gln Glu Pro Ile Glu Arg Glu Pro Leu Thr Ser
465                 470                 475                 480

Leu Lys Ser Leu Phe Gly Ser Asp Pro Leu Ser Gln
                485                 490

<210> SEQ ID NO 37
<211> LENGTH: 2997
<212> TYPE: DNA
<213> ORGANISM: Human immunodeficiency virus type 1

<400> SEQUENCE: 37
tttagggaaa atttggcctt cccacaaggg gaggccaggg aatttccttc agaacagacc     60
agagccaaca gccccaccag cagagagctt caggttcgaa gaaacaaccc ccgctccgaa    120
acaggagccg agagaaaggg aacccttaac ttccctcaaa tcactctttg gcagcgaccc    180
cttgtctcaa taaaatagg gggcagaca agggaggctc tcttagacac aggagcagat    240
gatacagtat tagaagacat aaatttgcca ggaaaatgga accaaaaat gataggagga    300 attggaggtt ttatcaaagt aagacagtat gatcaaatac ttatagaaat ttgtggaaaa    360
aaggctatag gtacagtatt agtagggcct acacctgtca acataattgg cagaaacatg    420

```
ttgactcagc ttggatgcac actaaacttt ccaatcagtc ccattgaaac tgtaccagta    480
aaactgaagc caggaatgga tggcccaaag gttaaacaat ggccgttaac agaagagaaa    540
ataaaagcat taacagcaat ttgtgaagaa atggaaaagg aaggaaaaat tacaaaaatt    600
gggcctgaaa atccatataa cactccaata tttgccataa aaagaaaga cagcactaag     660 tggagaaaat tagtagattt cagggaactc aataaaagaa ctcaagactt ttgggaggtt    720
caattaggaa taccacaccc agcagggtta aaaagaaaa atcagtgac agtactggat      780 gtgggagatg catattttc agttccttta gatgaaggct tcaggaaata tactgcattc     840
accataccta gtataaacaa tgaaacacca gggattagat atcaatataa tgtgcttcca    900
caaggatgga aagggtcacc agcaatattc cagggtagca tgacaaaaat cttagagccc    960
tttagagctc aaaatccaga aatagtcatc tatcaatata tggatgactt gtatgtagga   1020
tctgacttag aaatagggca acatagagca aaaatagaag agttaagaga acatctatta   1080
aagtggggat ttaccacacc agacaaaaaa catcagaaag aaccccccatt tctttggatg   1140 gggtatgaac tccatcctga caaatggaca gtacagccta tacagctgcc agaaaaggat   1200
agctggactg tcaatgatat acagaagtta gtgggaaaat taaactgggc aagtcagatt   1260
tacccaggga ttaaagtaag gcaactttgt aagctcctta gggggaccaa agcactaaca   1320
gacatagtac cactaactga agaagcagaa ttagaattgg cagagaacag ggaaattcta   1380
aaagaaccag tgcatggagt atattatgac ccatcaaaag acttgatagc tgaaatacag   1440
aaacaggggg atgaccaatg gacatatcaa atttaccaag aaccattcaa aaacctgaag   1500
acaggaaagt atgcaaaaag gaggactacc cacactaatg atgtaaaaca gttaacagag   1560
gcagtgcaaa aaatatcctt ggaaagcata gtaatatggg aaagactcc taaatttaga   1620 ctacccatcc aaaagaaac atgggaaata tggtggacag actattggca agccacatgg   1680
attcctgagt gggagtttgt taatacccct cccctagtaa actatggta ccagctagaa    1740 aaagaaccca tagcaggagc agaaactttc tatgtagatg gagcagctaa tagggaaact   1800
aaaataggaa aagcggggta tgttactgac agaggaaggc agaaaattgt aactctaagt   1860
gaaacaacaa atcagaagac tgaattacaa gcaattcagc tagctttgca agattcagaa   1920
tcagaagtaa acataataac agactcacag tacgcattag gaatcattca agcacaacca   1980
gataggagtg aatcagagtt ggtcaatcaa ataatagaac aattaataaa aaaggaaagg   2040
gtctatctgt catgggtacc agcacacaac ggacttgcag gaaatgaaca tgtagataaa   2100
ttagtaagta ggggaatcag gaaagtgctg gttctagatg gaatagataa ggctcatgaa   2160
gagcatgaaa agtatcacag caattggaga gcaatggcta gtgagtttaa tctgccaccc   2220
gtagtagcaa agagaaatagt agccagctgt gataaatgtc agctaaaagg ggaagccata   2280
catggacaag tagattgtag tccggggata tggcaattag attgtacaca tttagaagga   2340
aaaatcatcc tggtagcagt ccatgtagcc agtggctaca tagaagcaga ggttatccca   2400
gcagaaacag gacaagaaac agcatactat atactaaaat tagcaggaag atggccagtc   2460
aaagtaatac atacagacaa tggcagtaat ttcaccagtg ctgcagttaa ggcagcctgt   2520
tggtgggcag gtatccaaca ggaatttggg attccctaca atccccaaag tcagggagta   2580
gtagaatcca tgaataaaga attaaagaaa atcatagggc aggtaagaga tcaagctgag   2640
caccttaaga cagcagtaca aatggcagta ttcattcaca attttaaaag aaaagggggg   2700 attgggggt acagtgcagg ggaaagaata atagacataa tagcaacaga catacaaact   2760
```

```
aaagaattac aaaaacaaat tataaaaatt caaaattttc gggtttatta cagagacagc  2820
agagatccta tttggaaagg accagccaag ctactctgga aaggtgaagg ggcagtagta  2880
atacaagaca acagtgacat aaaggtagta ccaaggagga agtaaaaat cattagggac   2940 tatggaaaac agatggcagg tgctgattgt gtggcaggta gacaggatga agattag     2997
```

<210> SEQ ID NO 38
<211> LENGTH: 998
<212> TYPE: PRT
<213> ORGANISM: Human immunodeficiency virus type 1

<400> SEQUENCE: 38

```
Phe Arg Glu Asn Leu Ala Phe Pro Gln Gly Glu Ala Arg Glu Phe Pro
1               5                   10                  15

Ser Glu Gln Thr Arg Ala Asn Ser Pro Thr Ser Arg Glu Leu Gln Val
            20                  25                  30

Arg Arg Asn Asn Pro Arg Ser Glu Thr Gly Ala Glu Arg Lys Gly Thr
        35                  40                  45

Leu Asn Phe Pro Gln Ile Thr Leu Trp Gln Arg Pro Leu Val Ser Ile
    50                  55                  60

Lys Ile Gly Gly Gln Thr Arg Glu Ala Leu Leu Asp Thr Gly Ala Asp
65                  70                  75                  80

Asp Thr Val Leu Glu Asp Ile Asn Leu Pro Gly Lys Trp Lys Pro Lys
                85                  90                  95

Met Ile Gly Gly Ile Gly Gly Phe Ile Lys Val Arg Gln Tyr Asp Gln
            100                 105                 110

Ile Leu Ile Glu Ile Cys Gly Lys Lys Ala Ile Gly Thr Val Leu Val
        115                 120                 125

Gly Pro Thr Pro Val Asn Ile Ile Gly Arg Asn Met Leu Thr Gln Leu
    130                 135                 140

Gly Cys Thr Leu Asn Phe Pro Ile Ser Pro Ile Glu Thr Val Pro Val
145                 150                 155                 160

Lys Leu Lys Pro Gly Met Asp Gly Pro Lys Val Lys Gln Trp Pro Leu
                165                 170                 175

Thr Glu Glu Lys Ile Lys Ala Leu Thr Ala Ile Cys Glu Glu Met Glu
            180                 185                 190

Lys Glu Gly Lys Ile Thr Lys Ile Gly Pro Glu Asn Pro Tyr Asn Thr
        195                 200                 205

Pro Ile Phe Ala Ile Lys Lys Lys Asp Ser Thr Lys Trp Arg Lys Leu
    210                 215                 220

Val Asp Phe Arg Glu Leu Asn Lys Arg Thr Gln Asp Phe Trp Glu Val
225                 230                 235                 240

Gln Leu Gly Ile Pro His Pro Ala Gly Leu Lys Lys Lys Ser Val
                245                 250                 255

Thr Val Leu Asp Val Gly Asp Ala Tyr Phe Ser Val Pro Leu Asp Glu
            260                 265                 270

Gly Phe Arg Lys Tyr Thr Ala Phe Thr Ile Pro Ser Ile Asn Asn Glu
        275                 280                 285

Thr Pro Gly Ile Arg Tyr Gln Tyr Asn Val Leu Pro Gln Gly Trp Lys
    290                 295                 300

Gly Ser Pro Ala Ile Phe Gln Gly Ser Met Thr Lys Ile Leu Glu Pro
305                 310                 315                 320

Phe Arg Ala Gln Asn Pro Glu Ile Val Ile Tyr Gln Tyr Met Asp Asp
                325                 330                 335
```

-continued

```
Leu Tyr Val Gly Ser Asp Leu Glu Ile Gly Gln His Arg Ala Lys Ile
            340                 345                 350
Glu Glu Leu Arg Glu His Leu Leu Lys Trp Gly Phe Thr Thr Pro Asp
        355                 360                 365
Lys Lys His Gln Lys Glu Pro Pro Phe Leu Trp Met Gly Tyr Glu Leu
    370                 375                 380
His Pro Asp Lys Trp Thr Val Gln Pro Ile Gln Leu Pro Glu Lys Asp
385                 390                 395                 400
Ser Trp Thr Val Asn Asp Ile Gln Lys Leu Val Gly Lys Leu Asn Trp
                405                 410                 415
Ala Ser Gln Ile Tyr Pro Gly Ile Lys Val Arg Gln Leu Cys Lys Leu
            420                 425                 430
Leu Arg Gly Thr Lys Ala Leu Thr Asp Ile Val Pro Leu Thr Glu Glu
        435                 440                 445
Ala Glu Leu Glu Leu Ala Glu Asn Arg Glu Ile Leu Lys Glu Pro Val
    450                 455                 460
His Gly Val Tyr Tyr Asp Pro Ser Lys Asp Leu Ile Ala Glu Ile Gln
465                 470                 475                 480
Lys Gln Gly Asp Gln Trp Thr Tyr Gln Ile Tyr Gln Glu Pro Phe
                485                 490                 495
Lys Asn Leu Lys Thr Gly Lys Tyr Ala Lys Arg Arg Thr Thr His Thr
            500                 505                 510
Asn Asp Val Lys Gln Leu Thr Glu Ala Val Gln Lys Ile Ser Leu Glu
        515                 520                 525
Ser Ile Val Ile Trp Gly Lys Thr Pro Lys Phe Arg Leu Pro Ile Gln
    530                 535                 540
Lys Glu Thr Trp Glu Ile Trp Trp Thr Asp Tyr Trp Gln Ala Thr Trp
545                 550                 555                 560
Ile Pro Glu Trp Glu Phe Val Asn Thr Pro Pro Leu Val Lys Leu Trp
                565                 570                 575
Tyr Gln Leu Glu Lys Glu Pro Ile Ala Gly Ala Glu Thr Phe Tyr Val
            580                 585                 590
Asp Gly Ala Ala Asn Arg Glu Thr Lys Ile Gly Lys Ala Gly Tyr Val
        595                 600                 605
Thr Asp Arg Gly Arg Gln Lys Ile Val Thr Leu Ser Glu Thr Thr Asn
    610                 615                 620
Gln Lys Thr Glu Leu Gln Ala Ile Gln Leu Ala Leu Gln Asp Ser Glu
625                 630                 635                 640
Ser Glu Val Asn Ile Ile Thr Asp Ser Gln Tyr Ala Leu Gly Ile Ile
                645                 650                 655
Gln Ala Gln Pro Asp Arg Ser Glu Ser Glu Leu Val Asn Gln Ile Ile
            660                 665                 670
Glu Gln Leu Ile Lys Lys Glu Arg Val Tyr Leu Ser Trp Val Pro Ala
        675                 680                 685
His Asn Gly Leu Ala Gly Asn Glu His Val Asp Lys Leu Val Ser Arg
    690                 695                 700
Gly Ile Arg Lys Val Leu Val Leu Asp Gly Ile Asp Lys Ala His Glu
705                 710                 715                 720
Glu His Glu Lys Tyr His Ser Asn Trp Arg Ala Met Ala Ser Glu Phe
                725                 730                 735
Asn Leu Pro Pro Val Val Ala Arg Glu Ile Val Ala Ser Cys Asp Lys
            740                 745                 750
Cys Gln Leu Lys Gly Glu Ala Ile His Gly Gln Val Asp Cys Ser Pro
```

```
                755                 760                 765
Gly Ile Trp Gln Leu Asp Cys Thr His Leu Glu Gly Lys Ile Ile Leu
            770                 775                 780

Val Ala Val His Val Ala Ser Gly Tyr Ile Glu Ala Glu Val Ile Pro
785                 790                 795                 800

Ala Glu Thr Gly Gln Glu Thr Ala Tyr Tyr Ile Leu Lys Leu Ala Gly
                805                 810                 815

Arg Trp Pro Val Lys Val Ile His Thr Asp Asn Gly Ser Asn Phe Thr
            820                 825                 830

Ser Ala Ala Val Lys Ala Ala Cys Trp Trp Ala Gly Ile Gln Gln Glu
                835                 840                 845

Phe Gly Ile Pro Tyr Asn Pro Gln Ser Gln Gly Val Val Glu Ser Met
850                 855                 860

Asn Lys Glu Leu Lys Lys Ile Ile Gly Gln Val Arg Asp Gln Ala Glu
865                 870                 875                 880

His Leu Lys Thr Ala Val Gln Met Ala Val Phe Ile His Asn Phe Lys
                885                 890                 895

Arg Lys Gly Gly Ile Gly Gly Tyr Ser Ala Gly Glu Arg Ile Ile Asp
            900                 905                 910

Ile Ile Ala Thr Asp Ile Gln Thr Lys Glu Leu Gln Lys Gln Ile Ile
            915                 920                 925

Lys Ile Gln Asn Phe Arg Val Tyr Tyr Arg Asp Ser Arg Asp Pro Ile
930                 935                 940

Trp Lys Gly Pro Ala Lys Leu Leu Trp Lys Gly Glu Gly Ala Val Val
945                 950                 955                 960

Ile Gln Asp Asn Ser Asp Ile Lys Val Val Pro Arg Arg Lys Val Lys
                965                 970                 975

Ile Ile Arg Asp Tyr Gly Lys Gln Met Ala Gly Ala Asp Cys Val Ala
            980                 985                 990

Gly Arg Gln Asp Glu Asp
        995

<210> SEQ ID NO 39
<211> LENGTH: 101
<212> TYPE: PRT
<213> ORGANISM: Human immunodeficiency virus type 1

<400> SEQUENCE: 39

Met Glu Pro Val Asp Pro Asn Leu Glu Pro Trp Asn His Pro Gly Ser
1               5                   10                  15

Gln Pro Lys Thr Ala Cys Asn Lys Cys Tyr Cys Lys His Cys Ser Tyr
            20                  25                  30

His Cys Leu Val Cys Phe Gln Thr Lys Gly Leu Gly Ile Ser Tyr Gly
        35                  40                  45

Arg Lys Lys Arg Arg Gln Arg Arg Ser Ala Pro Pro Ser Ser Glu Asp
    50                  55                  60

His Gln Asn Leu Ile Ser Lys Gln Pro Leu Pro Gln Thr Arg Gly Asp
65                  70                  75                  80

Pro Thr Gly Ser Glu Glu Ser Lys Lys Val Glu Ser Lys Thr Glu
                85                  90                  95

Thr Asp Pro Phe Asp
            100

<210> SEQ ID NO 40
<211> LENGTH: 101
```

```
<212> TYPE: PRT
<213> ORGANISM: Human immunodeficiency virus type 1

<400> SEQUENCE: 40

Met Glu Pro Val Asp Pro Lys Leu Glu Pro Trp Asn His Pro Gly Ser
1               5                   10                  15

Gln Pro Lys Thr Ala Cys Thr Gln Cys Tyr Cys Lys Lys Cys Ser Tyr
                20                  25                  30

His Cys Leu Val Cys Phe Gln Thr Lys Gly Leu Gly Ile Ser Tyr Gly
            35                  40                  45

Arg Lys Lys Arg Arg Gln Arg Arg Ala Pro Ser Ser Glu Asp
        50                  55                  60

His Gln Asn Pro Ile Ser Lys Gln Pro Leu Pro Arg Thr Arg Gly Asp
65                  70                  75                  80

Ser Thr Gly Ser Glu Glu Ser Lys Lys Val Ser Lys Thr Glu
                85                  90                  95

Thr Asp Gln Phe Asp
            100

<210> SEQ ID NO 41
<211> LENGTH: 101
<212> TYPE: PRT
<213> ORGANISM: Human immunodeficiency virus type 1

<400> SEQUENCE: 41

Met Glu Pro Ile Asp Pro Asn Leu Glu Pro Trp Asn His Pro Gly Ser
1               5                   10                  15

Gln Pro Asn Thr Pro Cys Thr Lys Cys Tyr Cys Lys Tyr Cys Ser Tyr
                20                  25                  30

His Cys Leu Val Cys Phe Gln Thr Lys Gly Leu Gly Ile Ser Tyr Gly
            35                  40                  45

Arg Lys Lys Arg Arg Gln Arg Arg Ser Thr Pro Pro Ser Ser Glu Asp
        50                  55                  60

His Gln Asn Leu Ile Ser Glu Gln Pro Leu Pro Gln Ala Arg Gly Val
65                  70                  75                  80

Pro Thr Gly Ser Glu Glu Ser Lys Lys Val Glu Ser Lys Thr Lys
                85                  90                  95

Thr Asp Pro Phe Asp
            100

<210> SEQ ID NO 42
<211> LENGTH: 101
<212> TYPE: PRT
<213> ORGANISM: Human immunodeficiency virus type 1

<400> SEQUENCE: 42

Met Glu Pro Val Asp Pro Asn Leu Glu Pro Trp Asn His Pro Gly Ser
1               5                   10                  15

Gln Pro Lys Thr Pro Cys Thr Asn Cys Tyr Cys Lys His Ser Ser Tyr
                20                  25                  30

His Cys Leu Val Cys Phe Gln Thr Lys Gly Leu Gly Ile Ser Tyr Gly
            35                  40                  45

Arg Lys Lys Arg Arg Gln Arg Arg Ser Thr Pro Pro Ser Ser Glu Asp
        50                  55                  60

His Gln Asn Leu Ile Ser Lys Gln Pro Leu Ser Gln Pro Glu Gly Asn
65                  70                  75                  80

Ser Thr Gly Ser Glu Lys Ser Lys Lys Lys Val Glu Ser Lys Thr Arg
```

Thr Asp Pro Phe Asp
         100

<210> SEQ ID NO 43
<211> LENGTH: 101
<212> TYPE: PRT
<213> ORGANISM: Human immunodeficiency virus type 1

<400> SEQUENCE: 43

Met Glu Pro Val Asp Pro Asn Leu Asp Pro Trp Asn His Pro Gly Ser
1               5                   10                  15

Gln Pro Lys Thr Pro Cys Thr Lys Cys Tyr Cys Lys His Cys Ser Tyr
            20                  25                  30

His Cys Leu Val Cys Phe Gln Thr Lys Gly Leu Gly Ile Ser Tyr Gly
        35                  40                  45

Arg Lys Lys Arg Arg Gln Arg Arg Ser Thr Pro Pro Ser Ser Glu Asp
    50                  55                  60

His Gln Asn Leu Ile Ser Lys Gln Pro Leu Pro Gln Pro Arg Gly Asp
65                  70                  75                  80

Ser Thr Gly Ser Glu Glu Ser Lys Lys Lys Val Glu Ser Lys Thr Lys
                85                  90                  95

Thr Asp Gln Phe Asp
         100

<210> SEQ ID NO 44
<211> LENGTH: 102
<212> TYPE: PRT
<213> ORGANISM: Human immunodeficiency virus type 1

<400> SEQUENCE: 44

Met Glu Pro Val Asp Leu Asp Leu Glu Pro Trp Asn Asn Pro Gly Ser
1               5                   10                  15

Gln Pro Lys Thr Ala Cys Asn Lys Cys Tyr Cys Lys His Cys Ser Tyr
            20                  25                  30

His Cys Leu Val Cys Phe Gln Thr Lys Gly Leu Gly Ile Ser Tyr Gly
        35                  40                  45

Arg Lys Lys Arg Arg Gln Gln Arg Arg Ser Thr Pro Ser Ser Ser Lys
    50                  55                  60

Asp His Gln Asn Pro Ile Ser Lys Gln Pro Leu Pro Gln Pro Arg Gly
65                  70                  75                  80

Asp Ser Thr Gly Ser Glu Glu Ser Lys Lys Lys Val Glu Ser Lys Thr
                85                  90                  95

Gln Thr Asp Pro Phe Ala
         100

<210> SEQ ID NO 45
<211> LENGTH: 101
<212> TYPE: PRT
<213> ORGANISM: Human immunodeficiency virus type 1

<400> SEQUENCE: 45

Met Glu Pro Val Asp Pro Asn Leu Glu Pro Trp Asn His Pro Gly Ser
1               5                   10                  15

Gln Pro Lys Thr Ala Cys Asn Pro Cys Tyr Cys Lys Lys Cys Ser Tyr
            20                  25                  30

His Cys Leu Val Cys Phe Gln Lys Lys Gly Leu Gly Ile Ser Tyr Gly
        35                  40                  45

Arg Lys Lys Arg Arg Gln Arg Thr Ala Pro Pro Ser Ser Glu Asp
    50                  55                  60

His Gln Asn Pro Ile Ser Lys Gln Pro Phe Pro Arg Thr Gln Gly Asp
65                  70                  75                  80

Pro Thr Gly Ser Glu Glu Ser Lys Lys Lys Val Glu Ser Lys Thr Lys
                85                  90                  95

Thr Asp Gln Phe Asp
            100

<210> SEQ ID NO 46
<211> LENGTH: 101
<212> TYPE: PRT
<213> ORGANISM: Human immunodeficiency virus type 1

<400> SEQUENCE: 46

Met Glu Pro Val Asp Pro Asn Leu Glu Pro Trp Asn His Pro Gly Ser
1               5                   10                  15

Gln Pro Lys Thr Ala Cys Asn Lys Cys Tyr Cys Lys Val Cys Ser Tyr
                20                  25                  30

His Cys Leu Val Cys Phe Gln Thr Lys Gly Leu Gly Ile Ser Tyr Gly
            35                  40                  45

Arg Lys Lys Arg Arg Gln Arg Arg Ser Ala Pro Pro Ser Ser Glu Asp
    50                  55                  60

His Gln Asn Pro Ile Ser Lys Gln Pro Leu Pro Gln Thr Arg Arg Asp
65                  70                  75                  80

Pro Thr Gly Ser Glu Glu Ser Lys Lys Val Glu Ser Lys Ala Glu
                85                  90                  95

Ala Asp Pro Phe Asp
            100

<210> SEQ ID NO 47
<211> LENGTH: 95
<212> TYPE: PRT
<213> ORGANISM: Human immunodeficiency virus type 1

<400> SEQUENCE: 47

Asn Leu Glu Pro Trp Asn His Pro Gly Ser Gln Pro Lys Thr Ala Cys
1               5                   10                  15

Asn Pro Cys Tyr Cys Lys His Cys Ser Tyr His Cys Leu Val Cys Phe
                20                  25                  30

Gln Thr Lys Gly Leu Gly Ile Ser Tyr Gly Arg Lys Lys Arg Arg Gln
            35                  40                  45

Arg Gln Thr Ala Pro Pro Ser Ser Glu Asp His Gln Asn Pro Ile Ser
    50                  55                  60

Lys Gln Pro Leu Pro Gln Thr Arg Gly Asp Pro Thr Gly Ser Glu Glu
65                  70                  75                  80

Ser Lys Lys Lys Val Glu Ser Lys Thr Lys Thr Asp Pro Phe Asp
                85                  90                  95

<210> SEQ ID NO 48
<211> LENGTH: 96
<212> TYPE: PRT
<213> ORGANISM: Human immunodeficiency virus type 1

<400> SEQUENCE: 48

Asn Leu Glu Pro Trp Asn His Pro Gly Ser Gln Pro Lys Thr Pro Cys
1               5                   10                  15

-continued

```
Asn Lys Cys Tyr Cys Lys His Cys Ser Tyr His Cys Leu Val Cys Phe
        20                  25                  30

Gln Thr Lys Gly Leu Gly Ile Ser Tyr Gly Arg Lys Lys Arg Arg Gln
        35                  40                  45

Arg Gln Thr Thr Pro Pro Ser Ser Glu Asp His Gln Asn Leu Val Ser
    50                  55                  60

Lys Gln Pro Leu Ser Gln Thr Arg Gly Asp Pro Thr Gly Ser Glu Glu
65                  70                  75                  80

Ser Lys Lys Lys Val Glu Ser Lys Thr Glu Thr Asp Pro Phe Asp Trp
                85                  90                  95

<210> SEQ ID NO 49
<211> LENGTH: 101
<212> TYPE: PRT
<213> ORGANISM: Human immunodeficiency virus type 1

<400> SEQUENCE: 49

Met Glu Pro Ile Asp Pro Asn Leu Glu Pro Trp Asn His Pro Gly Ser
1               5                   10                  15

Gln Pro Asn Thr Pro Cys Asn Asn Cys Tyr Cys Lys His Cys Ser Tyr
            20                  25                  30

His Cys Leu Val Cys Phe Gln Thr Lys Gly Leu Gly Ile Ser Tyr Gly
        35                  40                  45

Arg Lys Lys Arg Arg Gln Arg Arg Ser Thr Pro Pro Ser Ser Glu Asp
    50                  55                  60

His Gln Asn Pro Ile Ser Lys Gln Pro Leu Ser Gln Thr Arg Gly Asp
65                  70                  75                  80

Pro Thr Gly Ser Glu Glu Ser Lys Lys Lys Val Glu Ser Lys Thr Lys
                85                  90                  95

Thr Asp Pro Phe Asp
            100

<210> SEQ ID NO 50
<211> LENGTH: 101
<212> TYPE: PRT
<213> ORGANISM: Human immunodeficiency virus type 1

<400> SEQUENCE: 50

Met Glu Pro Val Asp Pro Asn Leu Glu Pro Trp Asn His Pro Gly Ser
1               5                   10                  15

Gln Pro Leu Thr Pro Cys Asn Lys Cys Tyr Cys Lys His Cys Ser Tyr
            20                  25                  30

His Cys Leu Val Cys Phe Gln Thr Lys Gly Leu Gly Ile Ser Tyr Gly
        35                  40                  45

Arg Lys Lys Arg Arg Gln Arg Arg Ser Thr Pro Pro Ser Ser Glu Asp
    50                  55                  60

His Gln Asn Leu Val Ser Lys Gln Pro Leu Pro Gln Thr Arg Gly Asp
65                  70                  75                  80

Pro Thr Gly Ser Glu Glu Ser Lys Lys Lys Val Glu Ser Lys Thr Lys
                85                  90                  95

Thr Asp Pro Phe Asp
            100

<210> SEQ ID NO 51
<211> LENGTH: 101
<212> TYPE: PRT
<213> ORGANISM: Human immunodeficiency virus type 1
```

```
<400> SEQUENCE: 51

Met Glu Pro Ile Asp Pro Asn Leu Glu Pro Trp Asn His Pro Gly Ser
1               5                  10                  15

Gln Pro Lys Thr Ala Cys Asn Lys Cys Phe Cys Lys Arg Cys Ser Tyr
            20                  25                  30

His Cys Gln Phe Cys Phe Leu Thr Lys Gly Leu Gly Ile Ser Tyr Gly
        35                  40                  45

Arg Lys Lys Arg Arg Gln Arg Ser Ala Pro Pro Ser Ser Glu Asp
    50                  55                  60

His Gln Asn Pro Ile Ser Lys Gln Pro Leu Pro Gln Thr Arg Gly Asp
65                  70                  75                  80

Pro Thr Gly Ser Glu Lys Ser Lys Lys Val Glu Ser Lys Thr Glu
                85                  90                  95

Thr Asp Pro Phe Asp
            100

<210> SEQ ID NO 52
<211> LENGTH: 101
<212> TYPE: PRT
<213> ORGANISM: Human immunodeficiency virus type 1

<400> SEQUENCE: 52

Met Glu Pro Ile Asp Pro Asn Leu Glu Pro Trp Asn His Pro Gly Ser
1               5                  10                  15

Gln Pro Lys Thr Pro Cys Asn Lys Cys Tyr Cys Lys Arg Cys Ser Tyr
            20                  25                  30

His Cys Leu Ala Cys Phe Gln Thr Lys Gly Leu Gly Ile Ser Tyr Gly
        35                  40                  45

Arg Lys Lys Arg Arg Gln Arg Arg Ser Thr Pro Pro Ser Ser Lys Asn
    50                  55                  60

His Gln Asn Pro Val Ser Lys Gln Pro Leu Pro Gln Thr Arg Gly Asp
65                  70                  75                  80

Pro Thr Gly Ser Glu Glu Ser Lys Lys Val Glu Ser Lys Thr Glu
                85                  90                  95

Thr Asp Pro Phe Asp
            100

<210> SEQ ID NO 53
<211> LENGTH: 101
<212> TYPE: PRT
<213> ORGANISM: Human immunodeficiency virus type 1

<400> SEQUENCE: 53

Met Glu Pro Thr Asp Pro Asn Leu Glu Pro Trp Asn His Pro Gly Ser
1               5                  10                  15

Gln Pro Lys Thr Pro Cys Asn Lys Cys Tyr Cys Lys Arg Cys Ser Tyr
            20                  25                  30

His Cys Leu Val Cys Phe Gln Lys Lys Gly Leu Gly Ile Ser Tyr Gly
        35                  40                  45

Arg Lys Lys Arg Arg Gln Arg Arg Asn Ala Pro Pro Ser Ser Glu Asp
    50                  55                  60

His Gln Asn Leu Ile Ser Lys Gln Pro Leu Pro Gln Thr Arg Gly Asp
65                  70                  75                  80

Pro Thr Gly Ser Glu Glu Ser Lys Lys Val Glu Ser Lys Thr Glu
                85                  90                  95

Thr Asp Pro Phe Asp
```

-continued

```
                100

<210> SEQ ID NO 54
<211> LENGTH: 101
<212> TYPE: PRT
<213> ORGANISM: Human immunodeficiency virus type 1

<400> SEQUENCE: 54

Met Glu Pro Val Asp Pro Asn Leu Glu Pro Trp Asn His Pro Gly Ser
1               5                   10                  15

Gln Pro Lys Thr Pro Cys Asn Thr Cys Tyr Cys Lys His Cys Ser Tyr
            20                  25                  30

His Cys Leu Val Cys Phe Gln Thr Lys Gly Leu Gly Ile Ser Tyr Gly
        35                  40                  45

Arg Lys Lys Arg Arg Gln Arg Ser Thr Pro Ser Asn Lys Asp
    50                  55                  60

His Gln Asn Pro Val Pro Lys Gln Pro Leu Pro Gln Pro Arg Gly Asp
65                  70                  75                  80

Ser Thr Gly Ser Glu Glu Ser Lys Lys Lys Val Glu Ser Lys Thr Lys
                85                  90                  95

Thr Asp Pro Phe Asp
            100

<210> SEQ ID NO 55
<211> LENGTH: 72
<212> TYPE: PRT
<213> ORGANISM: Human immunodeficiency virus type 1

<400> SEQUENCE: 55

Met Glu Pro Val Asp Pro Lys Leu Glu Pro Trp Asn His Pro Gly Ser
1               5                   10                  15

Gln Pro Lys Thr Pro Cys Asn Ser Cys Tyr Cys Lys Lys Cys Ser Tyr
            20                  25                  30

His Cys Leu Val Cys Phe Gln Lys Lys Gly Leu Gly Ile Tyr Tyr Gly
        35                  40                  45

Arg Lys Lys Gln Arg Gln Arg Arg Arg Ala Pro Pro Ser Asn Lys Asp
    50                  55                  60

His Gln Asn Pro Val Pro Lys Gln
65                  70

<210> SEQ ID NO 56
<211> LENGTH: 72
<212> TYPE: PRT
<213> ORGANISM: Human immunodeficiency virus type 1

<400> SEQUENCE: 56

Met Asp Pro Ile Asp Pro Asn Leu Glu Pro Trp Asn His Pro Gly Ser
1               5                   10                  15

Gln Pro Lys Thr Ala Cys Asn Lys Cys Tyr Cys Lys Arg Cys Cys Tyr
            20                  25                  30

His Cys Leu Val Cys Phe Gln Lys Lys Gly Leu Gly Ile Ser Tyr Gly
        35                  40                  45

Arg Lys Lys Arg Arg Gln Arg Arg Ser Ala Pro Pro Ser Asn Lys Asp
    50                  55                  60

His Gln Asn Pro Val Ser Lys Gln
65                  70

<210> SEQ ID NO 57
```

<211> LENGTH: 207
<212> TYPE: PRT
<213> ORGANISM: Human immunodeficiency virus type 1

<400> SEQUENCE: 57

```
Met Gly Gly Lys Trp Ser Lys Ser Ser Ile Val Gly Trp Pro Ala Val
1               5                   10                  15

Arg Glu Arg Ile Arg Arg Thr Glu Pro Ala Ala Glu Gly Val Gly Ala
            20                  25                  30

Ala Ser Gln Asp Leu Asp Lys His Gly Ala Leu Thr Ser Ser Asn Thr
        35                  40                  45

Ala His Asn Asn Ala Asp Cys Ala Trp Leu Gln Ala Gln Glu Glu Glu
    50                  55                  60

Glu Glu Val Gly Phe Pro Val Arg Pro Gln Val Pro Leu Arg Pro Met
65                  70                  75                  80

Thr Tyr Lys Gly Ala Phe Asp Leu Ser Phe Phe Leu Lys Glu Lys Gly
                85                  90                  95

Gly Leu Glu Gly Leu Ile Tyr Ser Lys Lys Arg Gln Glu Ile Leu Asp
            100                 105                 110

Leu Trp Val Tyr His Thr Gln Gly Phe Phe Pro Asp Trp Gln Asn Tyr
        115                 120                 125

Thr Pro Gly Pro Gly Val Arg Tyr Pro Leu Thr Phe Gly Trp Cys Phe
    130                 135                 140

Lys Leu Val Pro Val Asp Pro Arg Glu Val Glu Glu Ala Asn Glu Gly
145                 150                 155                 160

Glu Asn Asn Cys Leu Leu His Pro Met Ser Gln His Gly Met Glu Asp
                165                 170                 175

Glu Asp Arg Glu Val Leu Lys Trp Lys Phe Asp Ser Ser Leu Ala Arg
            180                 185                 190

Arg His Met Ala Arg Glu Leu His Pro Glu Tyr Tyr Lys Asp Cys
        195                 200                 205
```

<210> SEQ ID NO 58
<211> LENGTH: 207
<212> TYPE: PRT
<213> ORGANISM: Human immunodeficiency virus type 1

<400> SEQUENCE: 58

```
Met Gly Gly Lys Trp Ser Lys Ser Ser Ile Gly Gly Trp Pro Ala Ile
1               5                   10                  15

Arg Glu Arg Ile Arg Arg Ala Lys Pro Ala Ala Glu Gly Val Gly Ala
            20                  25                  30

Ala Ser Gln Asp Leu Glu Lys His Gly Ala Leu Thr Thr Ser Asn Thr
        35                  40                  45

Ala Arg Asn Asn Pro Asp Cys Ala Trp Leu Gln Ala Gln Glu Glu Glu
    50                  55                  60

Glu Glu Val Gly Phe Pro Val Arg Pro Gln Val Pro Leu Arg Pro Met
65                  70                  75                  80

Thr Tyr Lys Gly Ala Phe Asp Leu Ser Phe Phe Leu Lys Glu Lys Gly
                85                  90                  95

Gly Leu Glu Gly Leu Ile His Ser Lys Lys Arg Gln Asp Ile Leu Asp
            100                 105                 110

Leu Trp Val Tyr His Thr Gln Gly Tyr Phe Pro Asp Trp Gln Asn Tyr
        115                 120                 125

Thr Pro Gly Pro Gly Val Arg Tyr Pro Leu Thr Phe Gly Trp Cys Phe
    130                 135                 140
```

```
Lys Leu Val Pro Val Asp Pro Arg Glu Val Glu Glu Ala Asn Glu Gly
145                 150                 155                 160

Glu Asp Asn Cys Leu Leu His Pro Met Ser Gln His Gly Met Glu Asp
                165                 170                 175

Ala Glu Arg Glu Val Leu Met Trp Lys Phe Asp Ser Ser Leu Ala Arg
            180                 185                 190

Arg His Met Ala Arg Glu Leu His Pro Glu Tyr Tyr Lys Asp Cys
        195                 200                 205
```

<210> SEQ ID NO 59
<211> LENGTH: 207
<212> TYPE: PRT
<213> ORGANISM: Human immunodeficiency virus type 1

<400> SEQUENCE: 59

```
Met Gly Gly Lys Trp Ser Lys Ser Ser Ile Val Gly Trp Pro Ala Val
1               5                   10                  15

Arg Glu Arg Met Arg Lys Thr Glu Pro Ala Ala Glu Gly Val Gly Ala
            20                  25                  30

Ala Ser Gln Asp Leu Asp Lys His Gly Ala Leu Thr Ser Ser Asn Thr
        35                  40                  45

Ala Thr Thr Asn Ala Ala Cys Ala Trp Leu Glu Ala Gln Glu Glu Glu
    50                  55                  60

Gly Glu Val Gly Phe Pro Val Arg Pro Gln Val Pro Leu Arg Pro Met
65                  70                  75                  80

Thr Tyr Lys Gly Ala Phe Asp Leu Gly Phe Phe Leu Lys Glu Lys Gly
                85                  90                  95

Gly Leu Glu Gly Leu Ile Tyr Ser Lys Lys Arg Gln Glu Ile Leu Asp
            100                 105                 110

Leu Trp Val Tyr His Thr Gln Gly Phe Phe Pro Asp Trp Gln Asn Tyr
        115                 120                 125

Thr Leu Gly Pro Gly Val Arg Tyr Pro Leu Thr Phe Gly Trp Pro Phe
    130                 135                 140

Lys Leu Val Pro Val Asp Pro Gly Glu Val Glu Glu Ala Asn Lys Gly
145                 150                 155                 160

Glu Asn Asn Cys Leu Leu His Pro Ile Ser Leu His Gly Met Glu Asp
                165                 170                 175

Asp His Arg Glu Val Leu Lys Trp Lys Phe Asp Ser Gln Leu Ala Arg
            180                 185                 190

Arg His Ile Ala Arg Glu Leu His Pro Glu Tyr Tyr Lys Asp Cys
        195                 200                 205
```

<210> SEQ ID NO 60
<211> LENGTH: 207
<212> TYPE: PRT
<213> ORGANISM: Human immunodeficiency virus type 1

<400> SEQUENCE: 60

```
Met Gly Gly Lys Trp Ser Lys Ser Ser Ile Val Gly Trp Pro Ala Val
1               5                   10                  15

Arg Glu Arg Ile Arg Arg Thr Glu Pro Ala Ala Glu Gly Val Gly Ala
            20                  25                  30

Ala Ser Gln Asp Leu Asp Lys His Gly Ala Leu Thr Ser Ser Asn Thr
        35                  40                  45

Ala His Asn Asn Pro Asp Cys Ala Trp Leu Gln Ala Gln Glu Glu Glu
    50                  55                  60
```

```
Pro Glu Val Gly Phe Pro Val Arg Pro Gln Val Pro Leu Arg Pro Met
 65                  70                  75                  80

Thr Tyr Lys Ala Ala Phe Asp Leu Ser Phe Leu Lys Glu Lys Gly
                 85                  90                  95

Gly Leu Glu Gly Leu Ile Tyr Ser Lys Lys Arg Gln Asp Ile Leu Asp
                100                 105                 110

Leu Trp Val Tyr His Thr Gln Gly Tyr Phe Pro Asp Trp Gln Asn Tyr
                115                 120                 125

Thr Pro Gly Pro Gly Val Arg Leu Pro Leu Thr Phe Gly Trp Cys Phe
            130                 135                 140

Lys Leu Val Pro Val Asp Pro Glu Val Glu Ala Asn Lys Gly
145                 150                 155                 160

Glu Asn Asn Cys Leu Leu His Pro Leu Ser Gln His Gly Met Glu Asp
                165                 170                 175

Ala Asp Arg Glu Val Leu Lys Trp Val Phe Asp Ser Ser Leu Ala Arg
            180                 185                 190

Arg His Leu Ala Arg Glu Lys His Pro Glu Tyr Tyr Lys Asp Cys
            195                 200                 205

<210> SEQ ID NO 61
<211> LENGTH: 209
<212> TYPE: PRT
<213> ORGANISM: Human immunodeficiency virus type 1

<400> SEQUENCE: 61

Met Gly Gly Lys Trp Ser Lys Ser Ser Ile Val Gly Trp Pro Ala Val
  1               5                  10                  15

Arg Glu Arg Ile Arg Gln Thr Arg Ile Glu Pro Ala Ala Glu Gly Val
             20                  25                  30

Gly Ala Ala Ser Gln Asp Leu Asp Lys Tyr Gly Ala Leu Thr Ser Ser
             35                  40                  45

Asn Thr Ala His Asn Asn Ala Asp Cys Ala Trp Leu Gln Ala Gln Glu
 50                  55                  60

Glu Glu Gly Glu Val Gly Phe Pro Val Arg Pro Gln Val Pro Leu Arg
 65                  70                  75                  80

Pro Met Thr Tyr Lys Gly Ala Phe Asp Leu Ser Phe Phe Leu Lys Glu
                 85                  90                  95

Lys Gly Gly Leu Glu Gly Leu Ile Trp Ser Lys Lys Arg Gln Glu Ile
                100                 105                 110

Leu Asp Leu Trp Val Tyr His Thr Gln Gly Tyr Phe Pro Asp Trp Gln
            115                 120                 125

Asn Tyr Thr Pro Gly Pro Gly Val Arg Phe Pro Leu Thr Phe Gly Trp
        130                 135                 140

Cys Phe Lys Leu Val Pro Val Asp Pro Ser Glu Val Glu Glu Ala Asn
145                 150                 155                 160

Lys Gly Glu Asn Asn Cys Leu Leu His Pro Met Ser Gln His Gly Met
                165                 170                 175

Glu Asp Glu Asp Arg Glu Val Leu Lys Trp Val Phe Asp Ser Ser Leu
            180                 185                 190

Ala Arg Arg His Thr Ala Arg Glu Lys His Pro Glu Phe Tyr Lys Asp
            195                 200                 205

Cys

<210> SEQ ID NO 62
```

<211> LENGTH: 207
<212> TYPE: PRT
<213> ORGANISM: Human immunodeficiency virus type 1

<400> SEQUENCE: 62

```
Met Gly Gly Lys Trp Ser Lys Ser Ser Leu Ala Gly Trp Pro Ala Val
1               5                   10                  15

Arg Glu Arg Ile Arg Arg Thr Glu Pro Ala Ala Glu Gly Val Gly Ala
            20                  25                  30

Ala Ser Arg Asp Leu Glu Lys His Gly Ala Leu Thr Ser Ser Asn Thr
        35                  40                  45

Ala His Asn Asn Pro Asp Cys Ala Trp Leu Gln Ala Gln Glu Glu Glu
    50                  55                  60

Glu Glu Val Gly Phe Pro Val Arg Pro Gln Val Pro Leu Arg Pro Met
65                  70                  75                  80

Thr Tyr Lys Ala Ala Val Asp Leu Ser Phe Phe Leu Lys Glu Lys Gly
                85                  90                  95

Gly Leu Glu Gly Leu Ile His Ser Lys Arg Arg Gln Asp Ile Leu Asp
            100                 105                 110

Leu Trp Val Tyr His Thr Gln Gly Tyr Phe Pro Asp Trp Gln Asn Tyr
        115                 120                 125

Thr Pro Gly Pro Gly Val Arg Phe Pro Leu Thr Phe Gly Trp Cys Phe
    130                 135                 140

Lys Leu Val Pro Val Asp Pro Arg Glu Val Glu Glu Ala Asn Lys Gly
145                 150                 155                 160

Glu Asn Asn Cys Leu Leu His Pro Met Ser Gln His Gly Ile Glu Asp
                165                 170                 175

Glu Glu Arg Glu Val Leu Gln Trp Met Phe Asp Ser Ser Leu Ala Arg
            180                 185                 190

Arg His Met Ala Arg Glu Lys His Pro Glu Phe Tyr Lys Asp Cys
        195                 200                 205
```

<210> SEQ ID NO 63
<211> LENGTH: 207
<212> TYPE: PRT
<213> ORGANISM: Human immunodeficiency virus type 1

<400> SEQUENCE: 63

```
Met Gly Gly Lys Trp Ser Lys Ser Ser Ile Ile Gly Trp Pro Glu Val
1               5                   10                  15

Arg Glu Arg Ile Arg Arg Thr Glu Pro Ala Ala Glu Gly Val Gly Ala
            20                  25                  30

Ala Ser Arg Asp Leu Glu Lys Tyr Gly Ala Leu Thr Ser Ser Asn Thr
        35                  40                  45

Ala His Thr Asn Ala Asp Cys Ala Trp Leu Gln Ala Gln Glu Glu Glu
    50                  55                  60

Asp Glu Val Gly Phe Pro Val Arg Pro Gln Val Pro Leu Arg Pro Met
65                  70                  75                  80

Thr Tyr Lys Ala Ala Phe Asp Leu Ser Phe Phe Leu Lys Glu Lys Gly
                85                  90                  95

Gly Leu Glu Gly Leu Ile Trp Ser Lys Arg Arg Gln Glu Ile Leu Asp
            100                 105                 110

Leu Trp Val Tyr Asn Thr Gln Gly Tyr Phe Pro Asp Trp Gln Asn Tyr
        115                 120                 125

Thr Pro Gly Pro Gly Val Arg Phe Pro Leu Thr Phe Gly Trp Cys Phe
    130                 135                 140
```

```
Lys Leu Val Pro Val Asp Pro Arg Glu Val Glu Glu Ala Asn Lys Gly
145                 150                 155                 160

Glu Asn Cys Leu Leu His Pro Met Ser Gln His Gly Ile Glu Asp
        165                 170                 175

Glu Asp Arg Glu Val Leu Lys Trp Glu Phe Asp Ser Ser Leu Ala Arg
        180                 185                 190

Arg His Leu Ala Arg Glu Ile His Pro Glu Tyr Tyr Lys Asp Cys
        195                 200                 205

<210> SEQ ID NO 64
<211> LENGTH: 214
<212> TYPE: PRT
<213> ORGANISM: Human immunodeficiency virus type 1

<400> SEQUENCE: 64

Met Gly Gly Lys Trp Ser Lys Ser Ser Ile Ile Gly Trp Pro Thr Glu
1               5                   10                  15

Gly Glu Arg Arg Arg Ala Lys Pro Thr Ile Arg Arg Thr Glu Pro
            20                  25                  30

Ala Ala Glu Gly Val Gly Ala Ala Ser Gln Asp Leu Glu Lys Tyr Gly
            35                  40                  45

Ala Leu Thr Ser Ser Asn Thr Ala His Thr Asn Ala Asp Cys Ala Trp
50                  55                  60

Leu Gln Ala Gln Glu Glu Asp Glu Val Gly Phe Pro Val Arg Pro
65                  70                  75                  80

Gln Val Pro Leu Arg Pro Met Thr Tyr Lys Ala Ala Phe Asp Leu Ser
                85                  90                  95

Phe Phe Leu Lys Glu Lys Gly Gly Leu Glu Gly Leu Ile Tyr Ser Lys
            100                 105                 110

Lys Arg Gln Asp Ile Leu Asp Leu Trp Val Tyr His Thr Gln Gly Phe
        115                 120                 125

Phe Pro Asp Trp Gln Asn Tyr Thr Pro Gly Pro Gly Val Arg Tyr Pro
    130                 135                 140

Leu Thr Phe Gly Trp Cys Phe Lys Leu Val Pro Val Asp Pro Arg Glu
145                 150                 155                 160

Val Glu Glu Ala Thr Lys Gly Glu Glu Asn Cys Leu Leu His Pro Leu
                165                 170                 175

Asn Gln His Gly Met Glu Asp Glu Lys Glu Val Leu Gln Trp Lys
            180                 185                 190

Phe Asp Ser Ser Leu Ala Arg Arg His Leu Ala Arg Glu Leu His Pro
    195                 200                 205

Glu Tyr Tyr Lys Asp Cys
        210

<210> SEQ ID NO 65
<211> LENGTH: 214
<212> TYPE: PRT
<213> ORGANISM: Human immunodeficiency virus type 1

<400> SEQUENCE: 65

Met Gly Gly Lys Trp Ser Lys Ser Ser Ile Val Gly Trp Pro Thr Glu
1               5                   10                  15

Arg Glu Arg Arg Arg Ala Lys Pro Thr Lys Arg Arg Pro Glu Pro
            20                  25                  30

Ala Ala Glu Gly Val Gly Ala Ala Ser Gln Asp Leu Asp Lys Tyr Gly
            35                  40                  45
```

Ala Leu Thr Thr Ser Asn Thr Ala His Asn Asn Pro Asp Cys Ala Trp
    50                  55                  60

Leu Gln Ala Gln Glu Glu Glu Glu Val Gly Phe Pro Val Thr Pro
65                  70                  75                  80

Gln Val Pro Val Arg Pro Met Thr Tyr Lys Ala Ala Phe Asp Leu Ser
                85                  90                  95

Phe Phe Leu Lys Glu Lys Gly Gly Leu Asp Gly Leu Ile His Ser Lys
            100                 105                 110

Lys Arg Gln Asp Ile Leu Asp Leu Trp Val Tyr His Thr Gln Gly Phe
        115                 120                 125

Phe Pro Asp Trp Gln Asn Tyr Thr Pro Gly Pro Gly Val Arg Tyr Pro
    130                 135                 140

Leu Thr Phe Gly Trp Cys Phe Lys Leu Val Pro Val Asp Pro Arg Glu
145                 150                 155                 160

Val Glu Glu Ala Asn Gln Gly Glu Asn Asn Cys Val Leu His Pro Leu
                165                 170                 175

Ser Gln His Gly Met Glu Asp Glu Glu Lys Glu Val Leu Lys Trp Met
            180                 185                 190

Phe Asp Ser Ser Leu Ala Arg Arg His Leu Ala Arg Glu Lys His Pro
        195                 200                 205

Glu Tyr Tyr Lys Asp Cys
    210

<210> SEQ ID NO 66
<211> LENGTH: 207
<212> TYPE: PRT
<213> ORGANISM: Human immunodeficiency virus type 1

<400> SEQUENCE: 66

Met Gly Gly Lys Trp Ser Lys Ser Ser Ile Ile Gly Trp Pro Glu Glu
1               5                   10                  15

Arg Glu Arg Ile Arg Arg Thr Glu Pro Ala Ala Glu Gly Val Gly Ala
                20                  25                  30

Ala Ser Arg Asp Leu Asp Lys Tyr Gly Ala Leu Thr Thr Ser Asn Thr
            35                  40                  45

Ala His Asn Asn Pro Asp Cys Ala Trp Leu Gln Ala Gln Glu Glu Glu
        50                  55                  60

Glu Glu Val Gly Phe Pro Val Arg Pro Gln Val Pro Leu Arg Pro Met
65                  70                  75                  80

Thr Tyr Lys Ala Ala Phe Asp Leu Ser Phe Phe Leu Lys Glu Lys Gly
                85                  90                  95

Gly Leu Glu Gly Leu Ile Tyr Ser Lys Lys Arg Gln Asp Ile Leu Asp
            100                 105                 110

Leu Trp Val Tyr Asn Thr Gln Gly Phe Phe Pro Asp Trp Gln Asn Tyr
        115                 120                 125

Thr Pro Gly Pro Gly Val Arg Tyr Pro Leu Thr Phe Gly Trp Cys Phe
    130                 135                 140

Lys Leu Val Pro Val Asp Pro Arg Glu Val Glu Ala Asn Lys Gly
145                 150                 155                 160

Glu Asn Asn Cys Leu Leu His Pro Met Ser Gln His Gly Met Glu Asp
                165                 170                 175

Pro Glu Gly Glu Val Leu Lys Trp Lys Phe Asp Ser Ser Leu Ala Arg
            180                 185                 190

Arg His Leu Ala Arg Glu Lys His Pro Glu Phe Tyr Lys Asp Cys

```
              195                 200                 205

<210> SEQ ID NO 67
<211> LENGTH: 207
<212> TYPE: PRT
<213> ORGANISM: Human immunodeficiency virus type 1

<400> SEQUENCE: 67

Met Gly Gly Lys Trp Ser Lys Ser Ser Ile Ile Gly Trp Pro Glu Val
1               5                   10                  15

Arg Glu Gly Ile Arg Arg Thr Glu Pro Ala Ala Glu Gly Val Gly Ala
            20                  25                  30

Ala Ser Arg Asp Leu Asp Lys Tyr Gly Ala Leu Thr Thr Ser Asn Thr
        35                  40                  45

Ala His Thr Asn Ala Asp Cys Ala Trp Leu Gln Ala Gln Glu Glu Glu
    50                  55                  60

Glu Glu Val Gly Phe Pro Val Arg Pro Gln Val Pro Leu Arg Pro Met
65                  70                  75                  80

Thr Tyr Lys Ala Ala Phe Asp Leu Ser Phe Phe Leu Lys Glu Lys Gly
                85                  90                  95

Gly Leu Asp Gly Leu Ile Tyr Ser Lys Lys Arg Gln Asp Ile Leu Asp
            100                 105                 110

Leu Trp Val Tyr His Thr Gln Gly Phe Phe Pro Asp Trp Gln Asn Tyr
        115                 120                 125

Thr Pro Gly Pro Gly Thr Arg Phe Pro Leu Thr Phe Gly Trp Cys Phe
    130                 135                 140

Lys Leu Val Pro Val Asp Pro Gln Glu Val Glu Glu Ala Asn Glu Gly
145                 150                 155                 160

Glu Asn Asn Cys Leu Leu His Pro Ile Ser Gln His Gly Met Glu Asp
                165                 170                 175

Ala Asp Arg Glu Val Leu Arg Trp Glu Phe Asp Ser Gln Leu Ala Arg
            180                 185                 190

Arg His Met Ala Arg Glu Leu His Pro Glu Phe Tyr Lys Asp Cys
        195                 200                 205

<210> SEQ ID NO 68
<211> LENGTH: 207
<212> TYPE: PRT
<213> ORGANISM: Human immunodeficiency virus type 1

<400> SEQUENCE: 68

Met Gly Gly Lys Trp Ser Lys Ser Ser Ile Val Gly Trp Pro Thr Val
1               5                   10                  15

Arg Glu Arg Met Arg Arg Thr Asp Pro Ala Ala Glu Gly Val Gly Ala
            20                  25                  30

Ala Ser Gln Asp Leu Asp Lys His Gly Ala Leu Thr Ser Ser Asn Thr
        35                  40                  45

Ala His Asn Asn Pro Ala Cys Ala Trp Leu Gln Ala Gln Glu Glu Asp
    50                  55                  60

Glu Glu Val Gly Phe Pro Val Arg Pro Gln Val Pro Leu Arg Pro Met
65                  70                  75                  80

Thr Phe Lys Gly Ala Phe Asp Leu Ser Phe Phe Leu Lys Glu Lys Gly
                85                  90                  95

Gly Leu Asp Gly Leu Ile Tyr Ser Lys Lys Arg His Asp Ile Leu Asp
            100                 105                 110

Leu Trp Val Tyr Asn Thr Gln Gly Tyr Phe Pro Asp Trp Gln Asn Tyr
```

```
              115                 120                 125
Thr Pro Gly Pro Gly Ile Arg Tyr Pro Leu Thr Phe Gly Trp Cys Phe
            130                 135                 140

Lys Leu Val Pro Val Asp Pro Arg Glu Val Glu Glu Ala Asn Glu Gly
145                 150                 155                 160

Asp Asn Asn Cys Leu Leu His Pro Met Ser Gln His Gly Ile Glu Asp
                165                 170                 175

Gly Glu Arg Glu Val Leu Lys Trp Glu Phe Asp Ser Ser Leu Ala Arg
            180                 185                 190

Arg His Met Ala Arg Glu Lys His Pro Glu Phe Tyr Lys Asp Cys
            195                 200                 205

<210> SEQ ID NO 69
<211> LENGTH: 221
<212> TYPE: PRT
<213> ORGANISM: Human immunodeficiency virus type 1

<400> SEQUENCE: 69

Met Gly Gly Lys Cys Ser Lys Ser Ser Ile Val Gly Trp Pro Glu Ile
1               5                   10                  15

Arg Glu Arg Ile Arg Gln Thr Arg Thr Gly Pro Ala Ala Glu Gly Val
            20                  25                  30

Gly Ala Ala Ser Gln Asp Leu Asp Lys Tyr Gly Ala Leu Thr Thr Ser
        35                  40                  45

Asn Thr Pro His Asn Asn Ala Ala Cys Ala Trp Leu Gln Ala Gln Glu
    50                  55                  60

Glu Glu Glu Glu Val Gly Phe Pro Val Arg Pro Gln Val Pro Leu Arg
65                  70                  75                  80

Pro Met Thr Tyr Lys Gly Ala Phe Asp Leu Gly Phe Phe Leu Lys Glu
                85                  90                  95

Lys Gly Gly Leu Asp Gly Leu Ile Trp Ser Lys Glu Lys Gly Gly Leu
            100                 105                 110

Asp Gly Leu Ile Trp Ser Lys Lys Arg Gln Glu Ile Leu Asp Leu Trp
        115                 120                 125

Val Tyr Asn Thr Gln Gly Tyr Phe Pro Asp Trp Gln Asn Tyr Thr Pro
    130                 135                 140

Gly Pro Gly Val Arg Tyr Pro Leu Thr Phe Gly Trp Cys Phe Lys Leu
145                 150                 155                 160

Val Pro Val Asp Pro Ser Glu Val Glu Glu Ala Asn Lys Gly Glu Asn
                165                 170                 175

Asn Cys Leu Leu His Pro Met Ser Gln His Gly Met Glu Asp Glu Glu
            180                 185                 190

Arg Glu Val Leu Lys Trp Gln Phe Asp Ser Ser Leu Ala Arg Arg His
        195                 200                 205

Met Ala Arg Glu Ile His Ser Glu Tyr Tyr Lys Asp Cys
    210                 215                 220

<210> SEQ ID NO 70
<211> LENGTH: 207
<212> TYPE: PRT
<213> ORGANISM: Human immunodeficiency virus type 1

<400> SEQUENCE: 70

Met Gly Gly Lys Trp Ser Lys Ser Ser Ile Val Gly Trp Pro Ala Val
1               5                   10                  15

Arg Glu Arg Ile Arg Arg Ala Glu Pro Ala Ala Glu Gly Val Gly Ala
```

-continued

```
                    20                  25                  30

Ala Ser Arg Asp Leu Asp Lys His Gly Ala Leu Thr Thr Ser Asn Thr
        35                  40                  45

Ala Gln Asn Asn Ala Asp Cys Ala Trp Leu Gln Ala Gln Glu Glu Ala
    50                  55                  60

Asp Glu Val Gly Phe Pro Val Arg Pro Gln Val Pro Leu Arg Pro Met
65                  70                  75                  80

Thr Tyr Lys Ala Ala Phe Asp Leu Gly Phe Leu Lys Glu Lys Gly
                85                  90                  95

Gly Leu Asp Gly Leu Ile Trp Ser Lys Lys Arg Gln Glu Ile Leu Asp
            100                 105                 110

Leu Trp Val Tyr His Thr Gln Gly Phe Phe Pro Asp Trp Gln Asn Tyr
        115                 120                 125

Thr Pro Gly Pro Gly Val Arg Tyr Pro Leu Thr Phe Gly Trp Cys Phe
    130                 135                 140

Lys Leu Val Pro Val Asp Pro Arg Glu Val Glu Glu Tyr Asn Lys Gly
145                 150                 155                 160

Glu Asn Asn Cys Leu Leu His Pro Met Ser Leu His Gly Met Glu Asp
                165                 170                 175

Glu Glu Gly Glu Val Leu Lys Trp Glu Phe Asp Ser Ser Leu Ala Arg
            180                 185                 190

Arg His Leu Ala Arg Glu Lys His Pro Glu Phe Tyr Lys Asp Cys
        195                 200                 205

<210> SEQ ID NO 71
<211> LENGTH: 206
<212> TYPE: PRT
<213> ORGANISM: Human immunodeficiency virus type 1

<400> SEQUENCE: 71

Met Gly Asn Lys Trp Ser Lys Ser Ser Ile Val Gly Trp Pro Ala Val
1               5                   10                  15

Arg Glu Arg Ile Arg Arg Thr Glu Pro Ala Ala Glu Gly Val Gly Ala
            20                  25                  30

Ala Ser Gln Asp Leu Asp Lys His Gly Ala Leu Thr Thr Ser Asn Thr
        35                  40                  45

Pro Thr Asn Asn Ala Asp Cys Ala Trp Leu Gln Ala Gln Glu Asp Glu
    50                  55                  60

Asp Val Gly Phe Pro Val Arg Pro Gln Val Pro Leu Arg Pro Met Thr
65                  70                  75                  80

Tyr Lys Ala Ala Val Asp Leu Ser Phe Phe Leu Lys Glu Lys Gly Gly
                85                  90                  95

Leu Glu Gly Leu Ile Tyr Ser Lys Lys Arg Gln Glu Ile Leu Asp Leu
            100                 105                 110

Trp Val Tyr His Thr Gln Gly Phe Phe Pro Asp Trp Gln Asn Tyr Thr
        115                 120                 125

Pro Gly Pro Gly Val Arg Phe Pro Leu Thr Phe Gly Trp Cys Phe Lys
    130                 135                 140

Leu Val Pro Val Asp Pro Arg Glu Val Glu Glu Ala Asn Glu Gly Glu
145                 150                 155                 160

Asn Asn Cys Leu Leu His Pro Met Ser Leu His Gly Met Glu Asp Glu
                165                 170                 175

Glu Arg Glu Val Leu Lys Trp Val Phe Asp Ser Ser Leu Ala Arg Arg
            180                 185                 190
```

His Leu Ala Arg Glu Leu His Pro Glu Tyr Tyr Lys Asp Cys
        195                 200                 205

<210> SEQ ID NO 72
<211> LENGTH: 218
<212> TYPE: PRT
<213> ORGANISM: Human immunodeficiency virus type 1

<400> SEQUENCE: 72

Met Gly Gly Lys Trp Ser Lys Ser Ser Ile Val Gly Trp Pro Ala Val
1               5                   10                  15

Arg Glu Arg Ile Arg Arg Thr Arg Pro Asn Gly Arg Glu Arg Ile Arg
            20                  25                  30

Gln Thr Glu Pro Ala Ala Glu Gly Val Gly Ala Ala Ser Gln Asp Leu
        35                  40                  45

Asp Lys Tyr Gly Ala Leu Thr Ser Ser Asn Thr Pro Gly Asn Asn Ala
    50                  55                  60

Asp Cys Ala Trp Leu Gln Ala Gln Glu Glu Glu Asp Val Gly Phe
65                  70                  75                  80

Pro Val Arg Pro Gln Val Pro Leu Arg Pro Met Thr Tyr Lys Ala Ala
                85                  90                  95

Val Asp Leu Ser Phe Phe Leu Lys Glu Lys Gly Gly Leu Glu Gly Leu
            100                 105                 110

Ile His Ser Lys Gln Arg Gln Asp Ile Leu Asp Leu Trp Val Tyr Asn
        115                 120                 125

Thr Gln Gly Tyr Phe Pro Asp Trp Gln Asn Tyr Thr Pro Gly Pro Gly
    130                 135                 140

Ile Arg Tyr Pro Leu Thr Phe Gly Trp Cys Phe Lys Leu Val Pro Val
145                 150                 155                 160

Asp Pro Arg Glu Val Glu Glu Ala Asn Glu Gly Glu Asp Asn Cys Leu
                165                 170                 175

Leu His Pro Met Ser Gln His Gly Ala Asp Asp Ala Asp Lys Glu Val
            180                 185                 190

Leu Met Trp Lys Phe Gly Ser Asp Leu Ala Tyr Lys His Ile Ala Arg
        195                 200                 205

Glu Ile His Ser Glu Tyr Tyr Lys Asp Cys
    210                 215

<210> SEQ ID NO 73
<211> LENGTH: 207
<212> TYPE: PRT
<213> ORGANISM: Human immunodeficiency virus type 1

<400> SEQUENCE: 73

Met Gly Gly Lys Leu Ser Lys Ser Ser Ile Val Gly Trp Pro Glu Val
1               5                   10                  15

Arg Glu Arg Leu Arg Arg Ala Gly Ser Ala Ala Glu Gly Val Gly Ala
            20                  25                  30

Ala Ser Gln Asp Leu Asp Arg His Gly Ala Leu Thr Ser Ser Asn Thr
        35                  40                  45

Pro Ala Thr Asn Ala Ala Cys Ala Gln Leu Glu Ala Gln Glu Glu Glu
    50                  55                  60

Glu Glu Val Gly Phe Pro Val Arg Pro Gln Val Pro Leu Arg Pro Met
65                  70                  75                  80

Thr Phe Lys Gly Ala Phe Asp Leu Ser Phe Phe Leu Lys Glu Lys Gly
                85                  90                  95

```
Gly Leu Asp Gly Leu Ile Tyr Ser Lys Lys Arg His Glu Ile Leu Asp
                100                 105                 110

Leu Trp Val Tyr Asn Thr Gln Gly Tyr Phe Pro Asp Trp Gln Asn Tyr
            115                 120                 125

Thr Pro Gly Pro Gly Val Arg Tyr Pro Leu Thr Phe Gly Trp Cys Tyr
        130                 135                 140

Lys Leu Val Pro Val Asp Pro Arg Lys Val Glu Glu Ala Asn Glu Gly
145                 150                 155                 160

Glu Asn Asn Cys Leu Leu His Pro Met His Gln His Gly Met Asp Asp
                165                 170                 175

Glu Asp Arg Glu Val Leu Ile Trp Lys Phe Asp Ser Ser Leu Ala Arg
            180                 185                 190

Arg His Met Ala Arg Glu Met His Pro Glu Tyr Tyr Lys Asp Cys
        195                 200                 205

<210> SEQ ID NO 74
<211> LENGTH: 207
<212> TYPE: PRT
<213> ORGANISM: Human immunodeficiency virus type 1

<400> SEQUENCE: 74

Met Gly Gly Lys Trp Ser Lys Ser Ser Ile Val Gly Trp Pro Glu Val
1               5                   10                  15

Arg Glu Arg Leu Arg Arg Thr Glu Pro Ala Ala Glu Gly Val Gly Thr
            20                  25                  30

Ala Ser Gln Asp Leu Asp Lys Tyr Gly Ala Leu Thr Ile Asn Asn Ser
        35                  40                  45

Gly Pro Thr Asn Ala Ala Cys Ala Trp Leu Glu Ala Gln Glu Glu Asp
    50                  55                  60

Gly Glu Val Gly Phe Pro Val Arg Pro Gln Val Pro Leu Arg Pro Met
65                  70                  75                  80

Thr Phe Lys Gly Ala Phe Asp Leu Ser Phe Phe Leu Lys Glu Lys Gly
                85                  90                  95

Gly Leu Asp Gly Leu Ile Tyr Ser Lys Lys Arg Gln Glu Ile Leu Asp
                100                 105                 110

Leu Trp Val Tyr His Thr Gln Gly Phe Phe Pro Asp Trp Gln Asn Tyr
            115                 120                 125

Thr Pro Gly Pro Gly Val Arg Tyr Pro Leu Thr Phe Gly Trp Cys Tyr
        130                 135                 140

Lys Leu Val Pro Val Asp Pro Gly Glu Val Glu Glu Ala Asn Lys Gly
145                 150                 155                 160

Glu Asn Asn Cys Leu Leu His Pro Leu Ser Gln His Gly Met Glu Asp
                165                 170                 175

Glu Asp Arg Glu Val Leu Lys Trp Gln Phe Asp Ser Ser Leu Ala Arg
            180                 185                 190

Arg His Leu Ala Arg Glu Leu His Pro Glu Tyr Tyr Lys Asp Cys
        195                 200                 205

<210> SEQ ID NO 75
<211> LENGTH: 214
<212> TYPE: PRT
<213> ORGANISM: Human immunodeficiency virus type 1

<400> SEQUENCE: 75

Met Gly Gly Lys Trp Ser Lys Gly Ser Ile Val Gly Trp Pro Ala Val
1               5                   10                  15
```

```
Arg Glu Arg Ile Arg Arg Thr Val Pro Thr Ala Lys Arg Thr Glu Pro
            20                  25                  30

Ala Ala Glu Gly Val Gly Pro Ala Ser Arg Asp Leu Asp Lys Tyr Gly
        35                  40                  45

Ala Leu Thr Ser Ser Asn Thr Thr Ser Asn Asn Ala Ala Cys Ala Trp
    50                  55                  60

Leu Glu Ala Gln Glu Glu Gly Glu Val Gly Phe Pro Val Lys Pro
65                  70                  75                  80

Gln Val Pro Val Arg Pro Met Thr Tyr Lys Ala Ala Leu Asp Leu Gly
                85                  90                  95

Phe Phe Leu Lys Glu Lys Gly Gly Leu Asp Gly Leu Ile Tyr Ser Lys
            100                 105                 110

Lys Arg Gln Asp Ile Leu Asp Leu Trp Val Tyr His Thr Gln Gly Phe
        115                 120                 125

Phe Pro Asp Trp Gln Asn Tyr Thr Pro Gly Pro Gly Val Arg Tyr Pro
    130                 135                 140

Leu Thr Phe Gly Trp Cys Phe Lys Leu Val Pro Val Asp Pro Glu Lys
145                 150                 155                 160

Val Glu Glu Ala Asn Glu Gly Glu Asn Asn Leu Leu His Pro Gly
                165                 170                 175

Ser Leu His Gly Met Asp Asp Pro Gln Arg Glu Val Leu Gln Trp Arg
            180                 185                 190

Phe Asp Ser Arg Leu Ala Phe His His Val Ala Arg Glu Leu His Pro
        195                 200                 205

Gly Ser Gly Asp Asp Cys
    210

<210> SEQ ID NO 76
<211> LENGTH: 214
<212> TYPE: PRT
<213> ORGANISM: Human immunodeficiency virus type 1

<400> SEQUENCE: 76

Met Gly Gly Lys Trp Ser Lys Gly Ser Ile Val Gly Trp Pro Ala Val
1               5                   10                  15

Arg Glu Arg Ile Arg Arg Thr Val Pro Thr Ala Lys Arg Thr Glu Pro
            20                  25                  30

Ala Ala Glu Gly Val Gly Pro Ala Ser Arg Asp Leu Asp Lys Tyr Gly
        35                  40                  45

Ala Leu Thr Ser Ser Asn Thr Thr Ser Asn Asn Ala Ala Cys Ala Trp
    50                  55                  60

Leu Glu Ala Gln Glu Glu Gly Glu Val Gly Phe Pro Val Lys Pro
65                  70                  75                  80

Gln Val Pro Val Arg Pro Met Thr Tyr Lys Ala Ala Leu Asp Leu Gly
                85                  90                  95

Phe Phe Leu Lys Glu Lys Gly Gly Leu Asp Gly Leu Ile Tyr Ser Thr
            100                 105                 110

Lys Arg Gln Glu Ile Leu Asp Leu Trp Val Tyr His Thr Gln Gly Phe
        115                 120                 125

Phe Pro Asp Trp Gln Asn Tyr Thr Ser Gly Pro Gly Val Arg Tyr Pro
    130                 135                 140

Leu Thr Phe Gly Trp Cys Tyr Lys Leu Val Pro Val Asp Pro Gln Glu
145                 150                 155                 160

Val Glu Glu Ala Asn Glu Gly Asp Asn Asn Cys Leu Leu His Pro Met
                165                 170                 175
```

```
Ser Leu His Gly Met Glu Asp Pro His Gly Glu Val Leu Lys Trp Gln
            180                 185                 190

Phe Asp Ser Ser Leu Ala Arg Arg His Leu Ala Arg Glu Leu His Pro
        195                 200                 205

Glu Tyr Tyr Lys Asp Cys
    210
```

```
<210> SEQ ID NO 77
<211> LENGTH: 212
<212> TYPE: PRT
<213> ORGANISM: Human immunodeficiency virus type 1

<400> SEQUENCE: 77

Met Gly Gly Lys Trp Ser Lys Ser Ser Ile Val Gly Trp Pro Ala Val
1               5                   10                  15

Arg Glu Arg Ile Arg Arg Ala Gly Pro Gly Arg Arg Ala Glu Pro Ala
            20                  25                  30

Ala Glu Gly Val Gly Ala Ala Ser Arg Asp Leu Asp Lys Tyr Gly Ala
        35                  40                  45

Leu Thr Thr Ser Asn Thr Ala Ser Asn Asn Ala Asp Cys Ala Trp Leu
    50                  55                  60

Glu Ala Gln Glu Asp Glu Glu Val Gly Phe Pro Val Lys Pro Gln Val
65                  70                  75                  80

Pro Leu Arg Pro Met Thr Tyr Lys Gly Ala Phe Asp Leu Gly Phe Phe
                85                  90                  95

Leu Lys Glu Lys Gly Gly Leu Asp Gly Leu Ile Tyr Ser Lys Lys Arg
            100                 105                 110

Gln Glu Ile Leu Asp Leu Trp Val Tyr Asn Thr Gln Gly Tyr Phe Pro
        115                 120                 125

Asp Trp Gln Asn Tyr Thr Ser Gly Pro Gly Ile Arg Tyr Pro Leu Thr
    130                 135                 140

Phe Gly Trp Cys Tyr Lys Leu Val Pro Val Asp Pro Ser Glu Val Glu
145                 150                 155                 160

Glu Ala Asn Lys Gly Glu Asp Asn Cys Leu Leu His Pro Met Ser Gln
                165                 170                 175

His Gly Met Glu Asp Glu Asp Arg Glu Val Leu Lys Trp Gln Phe Asp
            180                 185                 190

Ser Ser Leu Ala Arg Arg His Val Ala Arg Glu Leu His Pro Gly Val
        195                 200                 205

Leu Lys Asp Cys
    210
```

```
<210> SEQ ID NO 78
<211> LENGTH: 211
<212> TYPE: PRT
<213> ORGANISM: Human immunodeficiency virus type 1

<400> SEQUENCE: 78

Met Gly Gly Lys Trp Ser Lys Ser Ser Ile Val Gly Trp Pro Ala Val
1               5                   10                  15

Arg Glu Arg Ile Arg Arg Ala Gly Pro Gly Arg Arg Ala Glu Pro Ala
            20                  25                  30

Ala Glu Gly Val Gly Ala Ala Ser Arg Asp Leu Asp Lys Tyr Gly Ala
        35                  40                  45

Leu Thr Thr Ser Asn Thr Ala Ser Asn Asn Ala Asp Cys Ala Trp Leu
    50                  55                  60
```

```
Glu Ala Gln Glu Asp Glu Val Gly Phe Pro Val Lys Pro Gln Val
 65                  70                  75                  80

Pro Leu Arg Pro Met Thr Tyr Lys Gly Ala Phe Asp Leu Gly Phe Phe
                 85                  90                  95

Leu Lys Glu Lys Gly Thr Gly Trp Val Asn Leu Leu Lys Lys Arg Gln
            100                 105                 110

Asp Ile Leu Asp Leu Trp Val Tyr Asn Thr Gln Gly Phe Phe Pro Asp
            115                 120                 125

Trp Gln Asn Tyr Thr Pro Gly Pro Gly Val Arg Tyr Pro Leu Thr Phe
        130                 135                 140

Gly Trp Cys Tyr Lys Leu Val Pro Val Asp Pro Lys Glu Val Glu Glu
145                 150                 155                 160

Ala Asn Lys Gly Glu Asn Asn Cys Leu Leu His Pro Met Ser Gln His
                165                 170                 175

Gly Met Glu Asp Glu Glu Arg Glu Thr Leu Lys Trp Val Phe Asp Ser
            180                 185                 190

Ser Leu Ala Arg Arg His Ile Ala Arg Glu Lys His Pro Glu Tyr Tyr
        195                 200                 205

Lys Asp Cys
210

<210> SEQ ID NO 79
<211> LENGTH: 206
<212> TYPE: PRT
<213> ORGANISM: Human immunodeficiency virus type 1

<400> SEQUENCE: 79

Met Gly Ser Lys Trp Ser Lys Ser Ser Ile Val Gly Trp Pro Ala Val
  1               5                  10                  15

Arg Glu Arg Ile Arg Gln Thr Ser Ala Ala Glu Gly Val Gly Ala Ala
             20                  25                  30

Ser Gln Asp Leu Asp Lys His Gly Ala Leu Thr Thr Ser Asn Thr Ala
         35                  40                  45

Ser Asn Asn Ala Ala Cys Ala Trp Leu Glu Ala Gln Glu Glu Glu Gly
 50                  55                  60

Glu Val Gly Phe Pro Val Arg Pro Gln Val Pro Leu Arg Pro Met Thr
 65                  70                  75                  80

Tyr Lys Gly Ala Phe Asp Leu Ser Phe Phe Leu Lys Glu Lys Gly Gly
                 85                  90                  95

Leu Asp Gly Leu Ile Tyr Ser Lys Lys Arg Gln Glu Ile Leu Asp Leu
            100                 105                 110

Trp Val Tyr Asn Thr Gln Gly Tyr Phe Pro Asp Trp Gln Asn Tyr Thr
            115                 120                 125

Pro Gly Pro Gly Val Arg Tyr Pro Leu Thr Phe Gly Trp Cys Tyr Lys
        130                 135                 140

Leu Val Pro Val Asp Pro Lys Glu Val Glu Glu Ala Asn Glu Gly Glu
145                 150                 155                 160

Asn Asn Cys Leu Leu His Pro Met Ser Leu His Gly Met Glu Asp Glu
                165                 170                 175

Asp Arg Glu Val Leu Lys Trp Gln Phe Asp Ser Leu Leu Ala Arg Arg
            180                 185                 190

His Val Ala Arg Glu Leu His Pro Glu Phe Tyr Lys Asp Cys
        195                 200                 205
```

<210> SEQ ID NO 80
<211> LENGTH: 213
<212> TYPE: PRT
<213> ORGANISM: Human immunodeficiency virus type 1

<400> SEQUENCE: 80

Met Gly Gly Gln Trp Ser Lys Ser Ser Ile Ile Gly Trp Pro Ala Val
1               5                   10                  15

Arg Glu Arg Ile Arg Lys Thr Thr Pro Thr Ala Glu Arg Val Glu Ala
                20                  25                  30

Ala Ala Val Gly Val Gly Ala Ala Ser Gln Asp Leu Glu Lys His Gly
            35                  40                  45

Ala Leu Thr Ser Ser Asn Thr Ala Ala Ser Asn Ala Asp Cys Ala Trp
        50                  55                  60

Leu Glu Ala Gln Glu Glu Glu Glu Val Gly Phe Pro Val Arg Pro
65                  70                  75                  80

Gln Val Pro Leu Arg Pro Met Thr Tyr Lys Ala Ala Phe Asp Leu Gly
                85                  90                  95

Phe Phe Leu Lys Glu Lys Gly Gly Leu Asp Gly Ile Ile Tyr Ser Lys
                100                 105                 110

Lys Arg Gln Asp Ile Leu Asp Leu Trp Val Tyr His Thr Gln Gly Phe
            115                 120                 125

Phe Pro Asp Trp Gln Asn Tyr Thr Pro Gly Pro Gly Val Arg Tyr Pro
        130                 135                 140

Leu Thr Phe Gly Trp Pro Phe Lys Leu Val Pro Val Asp Pro Arg Glu
145                 150                 155                 160

Val Glu Glu Ala Asn Asn Gly Glu Asn Asn Cys Leu Leu His Pro Met
                165                 170                 175

Ser Gln His Gly Met Asp Asp Ala Asp Arg Glu Val Leu Met Trp Lys
                180                 185                 190

Phe Asp Ser Gly Leu Ala Arg Arg His Met Ala Arg Glu Tyr Ser Glu
            195                 200                 205

Phe Tyr Lys Asp Cys
        210

<210> SEQ ID NO 81
<211> LENGTH: 208
<212> TYPE: PRT
<213> ORGANISM: Human immunodeficiency virus type 1

<400> SEQUENCE: 81

Met Gly Gly Lys Trp Ser Lys Ser Ser Ile Val Gly Trp Pro Ala Val
1               5                   10                  15

Arg Glu Arg Met Arg Arg Ala Arg Thr Glu Pro Ala Ala Glu Gly Val
                20                  25                  30

Gly Ala Ala Ser Arg Asp Leu Glu Lys His Gly Ala Leu Thr Ser Ser
            35                  40                  45

Asn Thr Ala Ala Thr Asn Ala Ala Cys Ala Trp Leu Glu Ala Gln Glu
        50                  55                  60

Glu Glu Glu Val Gly Phe Pro Val Arg Pro Gln Val Pro Leu Arg
65                  70                  75                  80

Pro Met Thr Tyr Lys Gly Ala Val Asp Leu Gly Phe Phe Leu Lys Glu
                85                  90                  95

Lys Gly Gly Leu Asp Gly Leu Ile Tyr Ser Lys Gln Arg Gln Asp Ile
                100                 105                 110

Leu Asp Leu Trp Val Tyr Asn Thr Gln Gly Phe Phe Pro Asp Trp Gln

```
                115                 120                 125
Asn Tyr Thr Pro Gly Pro Gly Val Arg Tyr Pro Leu Thr Phe Gly Trp
    130                 135                 140

Cys Tyr Lys Leu Val Pro Val Asp Pro Arg Glu Val Glu Glu Ala Asn
145                 150                 155                 160

Lys Glu Asp Thr Arg Leu Leu His Pro Ile Ser Gln His Gly Met Glu
                165                 170                 175

Asp Ala Asp Arg Glu Val Leu Lys Trp Gln Phe Asp Ser Ser Leu Ala
                180                 185                 190

Arg Arg His Val Ala Arg Glu Leu Tyr Pro Glu Phe Tyr Lys Asp Cys
                195                 200                 205

<210> SEQ ID NO 82
<211> LENGTH: 150
<212> TYPE: PRT
<213> ORGANISM: Human immunodeficiency virus type 1

<400> SEQUENCE: 82

Met Gly Gly Lys Trp Ser Lys Arg Ser Val Val Gly Trp Thr Glu Ile
1               5                   10                  15

Arg Asp Arg Met Arg Arg Thr Arg Pro Thr Ala Pro Ala Ala Glu Gly
                20                  25                  30

Val Gly Ala Ala Ser Gln Asp Leu Asp Arg His Gly Ile Tyr Ser Lys
            35                  40                  45

Lys Arg Gln Glu Ile Leu Asp Leu Trp Val Tyr His Thr Gln Gly Phe
    50                  55                  60

Phe Pro Asp Trp Gln Asn Tyr Thr Pro Gly Pro Gly Val Arg Tyr Pro
65                  70                  75                  80

Leu Thr Phe Gly Trp Cys Phe Lys Leu Val Pro Val Asp Pro Lys Glu
                85                  90                  95

Val Glu Glu Ala Asn Glu Gly Glu Asp Asn Cys Leu Leu His Pro Met
                100                 105                 110

Ser Leu His Gly Met Glu Asp Ser Asp Gly Glu Val Leu Met Trp Lys
                115                 120                 125

Phe Asp Thr Gln Leu Ala Arg Arg His Ile Ala Arg Glu Leu His Pro
    130                 135                 140

Glu Phe Tyr Lys Asp Cys
145                 150

<210> SEQ ID NO 83
<211> LENGTH: 210
<212> TYPE: PRT
<213> ORGANISM: Human immunodeficiency virus type 1

<400> SEQUENCE: 83

Met Gly Asn Lys Trp Ser Lys Ser Trp Pro Ser Val Arg Glu Arg Ile
1               5                   10                  15

Arg Arg Ala Arg Pro Ala Ala Glu Glu Arg Thr Arg Pro Ala Ala Glu
                20                  25                  30

Gly Val Gly Thr Ala Ser Gln Asp Leu Asp Lys His Gly Ala Leu Thr
            35                  40                  45

Thr Ser Asn Thr Ala Thr Asn Asn Ala Ala Cys Ala Trp Val Glu Ala
    50                  55                  60

Gln Glu Glu Gly Glu Glu Val Gly Phe Pro Val Arg Pro Gln Val Pro
65                  70                  75                  80

Leu Arg Pro Met Thr Tyr Lys Ala Ala Phe Asp Leu Ser Phe Phe Leu
```

-continued

```
                85                  90                  95
Lys Glu Lys Gly Gly Leu Glu Gly Leu Ile Tyr Ser Lys Lys Arg Gln
            100                 105                 110
Asp Ile Leu Asp Leu Trp Val Tyr Asn Thr Gln Gly Phe Phe Pro Asp
            115                 120                 125
Trp Gln Asn Tyr Thr Pro Gly Pro Gly Ile Arg Tyr Pro Leu Thr Phe
            130                 135                 140
Gly Trp Cys Phe Lys Leu Val Pro Val Asp Pro Asp Glu Val Glu Glu
145                 150                 155                 160
Ala Asn Lys Gly Glu Asn Asn Cys Leu Leu His Pro Met Ser Gln His
            165                 170                 175
Gly Met Glu Asp Glu Asp Arg Glu Val Leu Gln Trp Lys Phe Asp Ser
            180                 185                 190
Ala Leu Ala Arg Arg His Met Ala Arg Glu Leu His Pro Glu Phe Phe
            195                 200                 205
Asn Asn
    210

<210> SEQ ID NO 84
<211> LENGTH: 211
<212> TYPE: PRT
<213> ORGANISM: Human immunodeficiency virus type 1

<400> SEQUENCE: 84

Met Gly Asn Lys Trp Ser Lys Ser Ser Ile Val Gly Trp Pro Ala Val
1               5                   10                  15
Arg Asp Arg Ile Arg Arg Thr Glu Pro Arg Thr Glu Pro Ala Ala Val
            20                  25                  30
Gly Val Gly Ala Ala Ser Gln Asp Leu Asp Lys His Gly Ala Leu Thr
            35                  40                  45
Ser Ser Asn Thr Asp Ala Asn Asn Ala Thr Cys Ala Trp Leu Arg Ala
        50                  55                  60
Gln Glu Glu Glu Glu Glu Val Gly Phe Pro Val Arg Pro Gln Val Pro
65                  70                  75                  80
Leu Arg Pro Met Thr Tyr Lys Ala Ala Phe Asp Leu Ser Phe Phe Leu
                85                  90                  95
Lys Glu Lys Gly Gly Leu Glu Gly Leu Ile Tyr Ser Lys Arg Arg Gln
            100                 105                 110
Asp Ile Leu Asp Leu Trp Val Tyr Asn Thr Gln Gly Phe Phe Pro Asp
            115                 120                 125
Trp His Asn Tyr Thr Pro Gly Pro Gly Thr Arg Tyr Pro Leu Thr Phe
            130                 135                 140
Gly Trp Cys Phe Lys Leu Val Pro Val Asp Pro Arg Glu Val Glu Glu
145                 150                 155                 160
Ala Thr Glu Gly Asp Asn Asn Cys Leu Leu His Pro Met Ser Gln His
            165                 170                 175
Gly Met Glu Asp Glu His Lys Glu Val Leu Gln Trp Lys Phe Asp Ser
            180                 185                 190
Leu Leu Ala Arg Arg His Met Ala Arg Glu Leu His Pro Glu Phe Tyr
            195                 200                 205
Lys Asp Cys
    210

<210> SEQ ID NO 85
<211> LENGTH: 203
```

```
<212> TYPE: PRT
<213> ORGANISM: Human immunodeficiency virus type 1

<400> SEQUENCE: 85

Met Gly Asn Lys Trp Ser Lys Ser Trp Pro Ala Val Arg Asp Arg Met
1               5                   10                  15

Arg Arg Thr Arg Pro Ala Ala Glu Gly Val Gly Ala Ala Ser Gln Asp
            20                  25                  30

Leu Asp Lys His Gly Ala Leu Thr Thr Ser Asn Thr Val Ser Asn Asn
            35                  40                  45

Ala Ala Gly Ala Trp Leu Gln Ala Gln Glu Glu Glu Glu Val Gly
50                  55                  60

Phe Pro Val Arg Pro Gln Val Pro Leu Arg Pro Met Thr Tyr Lys Ala
65                  70                  75                  80

Ala Phe Asp Leu Ser Phe Phe Leu Lys Glu Lys Gly Gly Leu Asp Gly
                85                  90                  95

Leu Ile Tyr Ser Lys Gln Arg Gln Asp Ile Leu Asp Leu Trp Val Tyr
            100                 105                 110

Asn Thr Gln Gly Tyr Phe Pro Asp Trp Gln Asn Tyr Thr Pro Gly Pro
            115                 120                 125

Gly Val Arg Tyr Pro Leu Thr Phe Gly Trp Cys Tyr Lys Leu Val Pro
130                 135                 140

Val Asp Pro Arg Glu Val Glu Glu Ala Asn Glu Gly Glu Asp Asn Cys
145                 150                 155                 160

Leu Leu His Pro Ile Ser Gln His Gly Met Glu Asp Pro Gln Arg Glu
                165                 170                 175

Thr Leu Lys Trp Val Phe Asp Ser His Leu Ala Arg Arg His Met Ala
            180                 185                 190

Arg Glu Leu His Pro Glu Tyr Tyr Lys Asp Cys
            195                 200

<210> SEQ ID NO 86
<211> LENGTH: 217
<212> TYPE: PRT
<213> ORGANISM: Human immunodeficiency virus type 1

<400> SEQUENCE: 86

Met Gly Gly Lys Trp Ser Lys Arg Ser Leu Gly Gly Trp Pro Ala Val
1               5                   10                  15

Arg Glu Arg Met Arg Arg Thr Glu Pro Ala Ala Glu Arg Ile Arg Gln
            20                  25                  30

Thr Glu Pro Ala Ala Glu Gly Val Gly Ala Ala Ser Gln Asp Leu Asp
            35                  40                  45

Arg His Gly Ala Leu Thr Ser Ser Asn Thr Glu Thr Thr Asn Ala Thr
50                  55                  60

Cys Ala Trp Leu Arg Ala Gln Glu Glu Asp Glu Glu Val Gly Phe Pro
65                  70                  75                  80

Val Lys Pro Gln Val Pro Leu Arg Pro Met Thr Tyr Lys Ala Ala Phe
                85                  90                  95

Asp Leu Gly Phe Phe Leu Lys Glu Lys Gly Gly Leu Glu Gly Leu Ile
            100                 105                 110

Tyr Ser Lys Lys Arg Gln Glu Ile Leu Asp Leu Trp Val Tyr Asn Thr
            115                 120                 125

Gln Gly Phe Phe Pro Asp Trp His Asn Tyr Thr Pro Gly Pro Gly Val
            130                 135                 140
```

-continued

```
Arg Tyr Pro Leu Thr Phe Gly Trp Cys Phe Lys Leu Val Pro Val Asp
145                 150                 155                 160

Pro Glu Glu Val Glu Glu Ala Thr Glu Gly Glu Asn Asn Cys Leu Leu
                165                 170                 175

His Pro Ile Asn Gln His Gly Met Asp Asp Asp Arg Glu Val Leu
            180                 185                 190

Lys Trp Lys Phe Asp Ser Met Leu Ala Arg Arg His Met Ala Arg Glu
        195                 200                 205

Leu His Pro Glu Tyr Tyr Lys Asp Cys
    210                 215
```

<210> SEQ ID NO 87
<211> LENGTH: 217
<212> TYPE: PRT
<213> ORGANISM: Human immunodeficiency virus type 1

<400> SEQUENCE: 87

```
Met Gly Gly Lys Trp Ser Lys Arg Ser Leu Gly Gly Trp Pro Ala Val
1               5                   10                  15

Arg Glu Arg Met Arg Arg Thr Glu Pro Ala Ala Glu Arg Ile Arg Gln
                20                  25                  30

Thr Glu Pro Ala Ala Glu Gly Val Gly Ala Ala Ser Gln Asp Leu Asp
            35                  40                  45

Arg His Gly Ala Leu Thr Ser Ser Asn Thr Glu Thr Thr Asn Ala Thr
        50                  55                  60

Cys Ala Trp Leu Arg Ala Gln Glu Glu Asp Glu Glu Val Gly Phe Pro
65                  70                  75                  80

Val Lys Pro Gln Val Pro Leu Arg Pro Met Thr Tyr Lys Ala Ala Phe
                85                  90                  95

Asp Leu Gly Phe Phe Leu Lys Glu Lys Gly Gly Leu Asp Gly Leu Ile
            100                 105                 110

Tyr Ser Lys Lys Arg Gln Glu Ile Leu Asp Leu Trp Val Tyr His Thr
        115                 120                 125

Gln Gly Phe Phe Pro Asp Trp Gln Asn Tyr Thr Pro Gly Pro Gly Val
    130                 135                 140

Arg Tyr Pro Leu Thr Phe Gly Trp Cys Phe Lys Leu Val Pro Val Asp
145                 150                 155                 160

Pro Ala Glu Val Glu Glu Asn Asn Lys Gly Glu Asp Ser Cys Leu Leu
                165                 170                 175

His Pro Ile Ser Gln His Gly Met Asp Asp Asp Lys Glu Val Leu
            180                 185                 190

Gln Trp Gln Phe Asp Ser Ser Leu Ala Arg Ile His Leu Ala Arg Glu
        195                 200                 205

Leu His Pro Glu Tyr Tyr Lys Asp Cys
    210                 215
```

<210> SEQ ID NO 88
<211> LENGTH: 209
<212> TYPE: PRT
<213> ORGANISM: Human immunodeficiency virus type 1

<400> SEQUENCE: 88

```
Met Gly Gly Lys Trp Ser Lys Arg Ser Leu Gly Gly Trp Pro Ala Val
1               5                   10                  15

Arg Glu Arg Met Arg Arg Thr Glu Pro Glu Pro Ala Ala Glu Gly Val
                20                  25                  30
```

```
Gly Ala Ala Ser Gln Asp Leu Asp Arg His Gly Ala Leu Thr Ser Ser
            35                  40                  45

Asn Thr Ala Thr Asn Asn Ala Thr Cys Ala Trp Leu Arg Ala Gln Glu
 50                  55                  60

Glu Glu Glu Glu Val Gly Phe Gln Val Lys Pro Gln Val Pro Leu Arg
 65                  70                  75                  80

Pro Met Thr Tyr Lys Ala Ala Phe Asp Leu Gly Phe Phe Leu Lys Glu
                 85                  90                  95

Lys Gly Gly Leu Asp Gly Leu Ile Ser Ser Lys Lys Arg Gln Glu Ile
            100                 105                 110

Leu Asp Leu Trp Val Tyr Asn Thr Gln Gly Tyr Phe Pro Asp Trp Gln
            115                 120                 125

Asn Tyr Thr Pro Gly Pro Gly Val Arg Tyr Pro Leu Thr Phe Gly Trp
130                 135                 140

Cys Ile Gln Leu Val Ala Val Phe Gln Ala Tyr Val Glu Glu Val Asn
145                 150                 155                 160

Glu Gly Glu Asn Asn Cys Leu Leu His Pro Ile Ser Gln His Gly Met
                165                 170                 175

Glu Asp Glu Glu Arg Glu Val Leu Lys Trp Gln Phe Asp Ser Ser Leu
            180                 185                 190

Ala Arg Arg His Val Ala Arg Glu Leu His Pro Glu Tyr Tyr Lys Asp
            195                 200                 205

Cys

<210> SEQ ID NO 89
<211> LENGTH: 207
<212> TYPE: PRT
<213> ORGANISM: Human immunodeficiency virus type 1

<400> SEQUENCE: 89

Met Gly Gly Lys Trp Ser Lys Cys Ser Met Gly Gly Trp Pro Ser Val
 1               5                  10                  15

Arg Glu Arg Met Arg Arg Thr Glu Pro Ala Ala Glu Gly Val Gly Ala
             20                  25                  30

Ala Ser Gln Asp Leu Asp Arg His Gly Ala Leu Thr Thr Ser Asn Thr
            35                  40                  45

Pro Thr Asn Asn Ala Asp Cys Ala Trp Leu Gln Ala Gln Glu Glu Gly
 50                  55                  60

Glu Glu Val Gly Phe Pro Val Arg Pro Gln Val Pro Leu Arg Pro Met
 65                  70                  75                  80

Thr Tyr Lys Ala Ala Phe Asp Leu Ser Phe Phe Leu Lys Glu Lys Gly
                 85                  90                  95

Gly Leu Glu Gly Leu Ile His Ser Lys Lys Arg Gln Asp Ile Leu Asp
            100                 105                 110

Leu Trp Val Tyr Gln Thr Gln Gly Phe Phe Pro Asp Trp Gln Asn Tyr
            115                 120                 125

Thr Pro Gly Pro Gly Val Arg Tyr Pro Leu Thr Phe Gly Trp Cys Phe
130                 135                 140

Lys Leu Val Pro Val Asp Pro Gly Glu Val Glu Glu Ala Asn Lys Gly
145                 150                 155                 160

Glu Asp Asn Cys Leu Leu His Pro Met Ser Gln His Gly Met Glu Asp
                165                 170                 175

Gly Asp Arg Glu Val Leu Lys Trp Val Phe Asp Ser Ser Leu Ala Arg
            180                 185                 190
```

-continued

Arg His Leu Gly Pro Glu Leu His Pro Glu Tyr Tyr Lys Asp Cys
        195                 200                 205

<210> SEQ ID NO 90
<211> LENGTH: 107
<212> TYPE: PRT
<213> ORGANISM: Human immunodeficiency virus type 1

<400> SEQUENCE: 90

Met Ala Gly Arg Ser Gly Asp Ser Asp Glu Ala Leu Leu Gln Ala Val
1               5                   10                  15

Arg Ile Ile Lys Ile Leu Tyr Gln Ser Asn Pro Tyr Pro Lys Pro Glu
            20                  25                  30

Gly Thr Arg Gln Ala Arg Lys Asn Arg Arg Arg Trp Arg Ala Arg
        35                  40                  45

Gln Arg Gln Ile His Ser Ile Ser Glu Arg Ile Leu Ser Thr Cys Leu
    50                  55                  60

Gly Arg Pro Ala Glu Pro Val Pro Leu Gln Leu Pro Pro Ile Glu Arg
65                  70                  75                  80

Leu His Ile Asp Cys Ser Glu Ser Ser Gly Thr Ser Gly Thr Gln Gln
                85                  90                  95

Ser Gln Gln Thr Thr Glu Gly Val Gly Ser Pro
            100                 105

<210> SEQ ID NO 91
<211> LENGTH: 100
<212> TYPE: PRT
<213> ORGANISM: Human immunodeficiency virus type 1

<400> SEQUENCE: 91

Met Ala Gly Arg Ser Gly Asp Ser Asp Lys Pro Leu Leu Gln Ala Val
1               5                   10                  15

Arg Ile Ile Lys Ile Leu Tyr Gln Ser Asn Pro Tyr Pro Lys Pro Glu
            20                  25                  30

Gly Thr Arg Gln Ala Arg Arg Asn Arg Arg Arg Trp Arg Ala Arg
        35                  40                  45

Gln Arg Gln Ile Asn Ser Ile Ser Glu Arg Ile Leu Ser Thr Cys Leu
    50                  55                  60

Gly Arg Pro Thr Glu Pro Val Pro Phe Gln Leu Pro Pro Ile Glu Arg
65                  70                  75                  80

Leu Cys Ile Asp Cys Ser Glu Ser Gly Gly Thr Ser Thr Ala Glu Gly
                85                  90                  95

Val Gly Ser Thr
            100

<210> SEQ ID NO 92
<211> LENGTH: 107
<212> TYPE: PRT
<213> ORGANISM: Human immunodeficiency virus type 1

<400> SEQUENCE: 92

Met Ala Gly Arg Ser Gly Asp Ser Asp Glu Ala Leu Leu Gln Ala Val
1               5                   10                  15

Arg Ile Ile Lys Ile Leu Tyr Gln Ser Asn Pro Tyr Pro Lys Pro Glu
            20                  25                  30

Gly Thr Arg Gln Ala Arg Arg Asn Arg Arg Arg Trp Arg Ala Arg
        35                  40                  45

Gln Arg Gln Ile His Ser Ile Ser Glu Arg Ile Leu Ser Thr Cys Leu

```
                50                  55                  60
Gly Arg Pro Ala Glu Pro Val Pro Leu Gln Leu Pro Pro Ile Glu Arg
 65                  70                  75                  80

Leu Asn Leu Gly Cys Asp Glu Ser Ser Gly Thr Ser Gly Thr Gln Gln
                 85                  90                  95

Pro Gln Gly Thr Thr Glu Gly Val Gly Ser Pro
            100                 105

<210> SEQ ID NO 93
<211> LENGTH: 107
<212> TYPE: PRT
<213> ORGANISM: Human immunodeficiency virus type 1

<400> SEQUENCE: 93

Met Ala Gly Arg Ser Gly Asp Ser Asp Lys Pro Leu Leu Gln Ala Val
 1               5                  10                  15

Arg Thr Ile Lys Ile Leu Tyr Gln Ser Asn Pro Tyr Pro Lys Pro Glu
                20                  25                  30

Gly Thr Arg Gln Ala Arg Arg Asn Arg Arg Arg Trp Arg Ala Arg
            35                  40                  45

Gln Arg Gln Ile His Ser Ile Gly Glu Arg Ile Leu Ser His Cys Leu
 50                  55                  60

Gly Arg Pro Ala Glu Pro Val Pro Leu Gln Leu Pro Pro Ile Glu Arg
 65                  70                  75                  80

Leu His Ile Asp Cys Ser Glu Ser Ser Gly Thr Ser Gly Thr Gln Gln
                 85                  90                  95

Ser Gln Gly Thr Thr Glu Gly Val Gly Ser Pro
            100                 105

<210> SEQ ID NO 94
<211> LENGTH: 107
<212> TYPE: PRT
<213> ORGANISM: Human immunodeficiency virus type 1

<400> SEQUENCE: 94

Met Ala Gly Arg Ser Gly Asp Ser Asp Glu Ala Leu Leu Gln Ala Val
 1               5                  10                  15

Arg Ile Ile Lys Ile Leu Tyr Gln Ser Asn Pro Tyr Pro Lys Pro Glu
                20                  25                  30

Gly Thr Arg Gln Ala Arg Arg Asn Arg Arg Arg Trp Arg Ala Arg
            35                  40                  45

Gln Arg Gln Ile Arg Ser Ile Ser Glu Arg Ile Leu Thr Thr Cys Leu
 50                  55                  60

Gly Arg Ser Ala Glu Pro Val Pro Leu Gln Leu Pro Pro Ile Glu Arg
 65                  70                  75                  80

Leu His Ile Asp Cys Ser Glu Asp Ser Gly Thr Ser Gly Thr Gln Gln
                 85                  90                  95

Ser Gln Gly Thr Pro Glu Gly Val Gly Ser Pro
            100                 105

<210> SEQ ID NO 95
<211> LENGTH: 107
<212> TYPE: PRT
<213> ORGANISM: Human immunodeficiency virus type 1

<400> SEQUENCE: 95

Met Ala Gly Arg Ser Gly Asp Ser Asp Glu Ala Leu Leu Gln Val Ile
 1               5                  10                  15
```

```
Arg Ile Ile Lys Ile Leu Tyr Gln Ser Ser Pro Tyr Pro Asn Pro Glu
            20                  25                  30

Gly Thr Arg Gln Ala Arg Lys Asn Gln Arg Arg Trp Arg Ala Arg
        35                  40                  45

Gln Arg Gln Ile His Ser Ile Ser Glu Arg Ile Leu Ser Thr Cys Leu
    50                  55                  60

Gly Arg Ser Ala Glu Pro Val Pro Leu Gln Leu Pro Pro Ile Glu Arg
65                  70                  75                  80

Leu His Ile Asp Cys Ser Glu Ser Ser Gly Thr Ser Gly Thr Gln Gln
                85                  90                  95

Ser Gln Gly Thr Thr Glu Gly Val Gly Ser Ser
            100                 105
```

<210> SEQ ID NO 96
<211> LENGTH: 107
<212> TYPE: PRT
<213> ORGANISM: Human immunodeficiency virus type 1

<400> SEQUENCE: 96

```
Met Ala Gly Arg Ser Gly Asp Ser Asp Glu Ala Leu Leu Gln Ala Val
1               5                   10                  15

Arg Ile Ile Lys Ile Leu Tyr Gln Ser Asn Pro Tyr Pro Lys Pro Glu
            20                  25                  30

Gly Ser Arg Gln Ala Arg Lys Asn Arg Arg Arg Trp Arg Ala Arg
        35                  40                  45

Gln Lys Gln Ile His Ser Ile Ser Glu Arg Ile Leu Ser Thr Cys Leu
    50                  55                  60

Gly Arg Ser Ala Glu Pro Val Pro Leu Arg Leu Pro Pro Ile Glu Arg
65                  70                  75                  80

Leu His Ile Asp Cys Ser Glu Ser Ser Gly Thr Ser Gly Thr Gln Gln
                85                  90                  95

Ser Gln Gly Thr Ala Glu Arg Val Gly Ser Pro
            100                 105
```

<210> SEQ ID NO 97
<211> LENGTH: 107
<212> TYPE: PRT
<213> ORGANISM: Human immunodeficiency virus type 1

<400> SEQUENCE: 97

```
Met Ala Gly Arg Ser Gly Asp Ser Asp Glu Ala Leu Leu Gln Ala Val
1               5                   10                  15

Lys Ile Ile Lys Ile Leu Tyr Gln Ser Asn Pro Tyr Pro Lys Pro Glu
            20                  25                  30

Gly Thr Arg Gln Ala Arg Lys Asn Arg Arg Arg Trp Arg Ala Arg
        35                  40                  45

Gln Arg Gln Ile His Ser Ile Ser Glu Arg Ile Leu Ser Thr Cys Leu
    50                  55                  60

Gly Arg Ser Ala Glu Pro Val Pro Leu Gln Leu Pro Pro Ile Glu Arg
65                  70                  75                  80

Leu His Ile Asp Cys Ser Glu Ser Ser Gly Thr Ser Gly Thr Gln Gln
                85                  90                  95

Ser Gln Gly Thr Ala Glu Arg Val Gly Ser Pro
            100                 105
```

<210> SEQ ID NO 98

```
<211> LENGTH: 107
<212> TYPE: PRT
<213> ORGANISM: Human immunodeficiency virus type 1

<400> SEQUENCE: 98

Met Ala Gly Arg Ser Gly Asp Ser Asp Glu Ala Leu Leu Gln Ala Val
1               5                   10                  15

Arg Thr Ile Lys Ile Leu Tyr Gln Ser Ser Pro Tyr Pro Lys Pro Glu
            20                  25                  30

Gly Thr Arg Gln Ala Arg Lys Asn Arg Arg Arg Trp Arg Ala Arg
        35                  40                  45

Gln Arg Gln Ile His Ser Ile Ser Glu Arg Ile Leu Asn Ala Cys Leu
    50                  55                  60

Gly Arg Pro Ala Glu Pro Val Pro Leu Gln Leu Pro Pro Leu Glu Arg
65                  70                  75                  80

Leu His Ile Asp Cys Ser Glu Asn Ser Gly Thr Ser Gly Thr Gln Gln
                85                  90                  95

Pro Gln Gly Thr Thr Glu Arg Val Gly Ser Pro
            100                 105

<210> SEQ ID NO 99
<211> LENGTH: 107
<212> TYPE: PRT
<213> ORGANISM: Human immunodeficiency virus type 1

<400> SEQUENCE: 99

Met Ala Gly Arg Ser Gly Asp Ser Asp Glu Ala Leu Leu Gln Ala Val
1               5                   10                  15

Arg Ile Ile Lys Ile Leu Tyr Gln Ser Asn Pro Tyr Pro Lys Pro Gly
            20                  25                  30

Gly Thr Arg Gln Ala Arg Lys Asn Arg Arg Arg Trp Arg Ala Arg
        35                  40                  45

Gln Arg Gln Ile His Ser Ile Ser Gln Arg Ile Leu Ser Asp Cys Leu
    50                  55                  60

Gly Arg Pro Ala Glu Pro Val Pro Leu Gln Leu Pro Pro Ile Glu Lys
65                  70                  75                  80

Leu His Ile Asp Cys Ser Glu Asp Ser Gly Thr Ser Gly Thr Gln Gln
                85                  90                  95

Ser Gln Gly Thr Thr Glu Arg Val Gly Ser Pro
            100                 105

<210> SEQ ID NO 100
<211> LENGTH: 107
<212> TYPE: PRT
<213> ORGANISM: Human immunodeficiency virus type 1

<400> SEQUENCE: 100

Met Ala Gly Arg Ser Gly Asp Asn Asp Glu Gln Leu Leu Gln Ala Val
1               5                   10                  15

Arg Ile Ile Lys Ile Leu Tyr Gln Ser Asn Pro Phe Pro Glu Pro Lys
            20                  25                  30

Gly Thr Arg Gln Ala Arg Lys Asn Arg Arg Arg Trp Arg Ala Arg
        35                  40                  45

Gln Arg Gln Ile Asn Ser Ile Ser Glu Arg Ile Leu Ser Asp Cys Leu
    50                  55                  60

Gly Arg Ser Ala Glu Pro Val Pro Leu Gln Leu Pro Pro Ile Glu Arg
65                  70                  75                  80
```

```
Leu His Ile Gly Cys Ser Glu Ser Gly Gly Thr Ser Gly Ala Gln Gln
                85                  90                  95

Ser His Gly Thr Thr Glu Gly Val Gly Arg Pro
            100                 105

<210> SEQ ID NO 101
<211> LENGTH: 107
<212> TYPE: PRT
<213> ORGANISM: Human immunodeficiency virus type 1

<400> SEQUENCE: 101

Met Ala Gly Arg Ser Gly Asp Ser Asp Ala Glu Leu Leu Gln Ala Val
1               5                   10                  15

Arg Ile Ile Lys Ile Leu Tyr Gln Ser Asn Pro Tyr Pro Glu Pro Glu
            20                  25                  30

Gly Thr Arg Gln Ala Arg Lys Asn Arg Arg Arg Trp Arg Ala Arg
        35                  40                  45

Gln Arg Gln Ile Asn Ser Ile Ser Glu Arg Ile Leu Ser Thr Cys Leu
    50                  55                  60

Gly Arg Ser Ala Glu Pro Val Pro Leu Gln Leu Pro Pro Ile Glu Arg
65                  70                  75                  80

Leu His Ile Gly Asp Ser Glu Ser Gly Gly Thr Ser Gly Thr Gln Gln
                85                  90                  95

Pro Gln Gly Thr Thr Glu Arg Val Gly Asn His
            100                 105

<210> SEQ ID NO 102
<211> LENGTH: 106
<212> TYPE: PRT
<213> ORGANISM: Human immunodeficiency virus type 1

<400> SEQUENCE: 102

Met Ala Gly Arg Ser Gly Asp Ser Asp Ala Ala Leu Leu Gln Ala
1               5                   10                  15

Val Arg Ile Ile Lys Ile Leu Tyr Gln Ser Ser Pro Glu Pro Arg Gly
            20                  25                  30

Thr Arg Gln Ala Arg Lys Asn Arg Arg Arg Trp Arg Ala Arg Gln
        35                  40                  45

Lys Gln Ile His Ser Leu Arg Glu Arg Ile Leu Ser Asn Cys Leu Gly
    50                  55                  60

Arg Pro Ala Glu Pro Val Pro Leu Gln Leu Pro Pro Ile Glu Arg Leu
65                  70                  75                  80

His Ile Asp Cys Ser Glu Asn Gly Gly Thr Ser Gly Thr Gln Gln Pro
                85                  90                  95

Gln Gly Thr Thr Glu Gly Val Gly Ser Pro
            100                 105

<210> SEQ ID NO 103
<211> LENGTH: 107
<212> TYPE: PRT
<213> ORGANISM: Human immunodeficiency virus type 1

<400> SEQUENCE: 103

Met Ala Gly Arg Ser Gly Asp Ser Asp Glu Ala Leu Leu Gln Ala Val
1               5                   10                  15

Arg Thr Ile Lys Ile Leu Tyr Gln Ser Ser Pro Tyr Pro Lys Pro Glu
            20                  25                  30

Gly Thr Arg Gln Ala Arg Lys Asn Arg Arg Arg Arg Trp Arg Ala Arg
```

-continued

```
                35                  40                  45
Gln Arg Gln Ile His Ser Ile Ser Glu Arg Ile Leu Ser Thr Cys Leu
         50                  55                  60
Gly Arg Pro Ala Glu Pro Val Pro Leu Gln Leu Pro Pro Ile Glu Arg
 65                  70                  75                  80
Leu His Ile Gly Asp Ser Glu Ser Ser Gly Thr Ser Gly Thr Gln Gln
                 85                  90                  95
Pro Gln Gly Thr Ala Glu Gly Leu Gly Ser Pro
            100                 105
```

<210> SEQ ID NO 104
<211> LENGTH: 107
<212> TYPE: PRT
<213> ORGANISM: Human immunodeficiency virus type 1

<400> SEQUENCE: 104

```
Met Ala Gly Arg Ser Gly Asp Ser Asp Glu Ala Leu Leu Gln Ala Val
 1               5                  10                  15
Arg Ile Ile Lys Ile Leu Tyr Gln Ser Ser Pro Tyr Pro Lys Pro Glu
                20                  25                  30
Gly Thr Arg Gln Ala Arg Lys Asn Arg Arg Arg Arg Trp Arg Ala Arg
             35                  40                  45
Gln Arg Gln Ile Asn Ser Ile Ser Glu Arg Ile Leu Ser Thr Cys Leu
         50                  55                  60
Gly Arg Pro Thr Glu Pro Val Pro Leu Gln Leu Pro Pro Ile Glu Arg
 65                  70                  75                  80
Leu His Ile Gly Cys Ser Glu Ser Ser Gly Thr Ser Gly Thr Gln Gln
                 85                  90                  95
Ser Gln Gly Thr Thr Glu Arg Val Gly Ser Pro
            100                 105
```

<210> SEQ ID NO 105
<211> LENGTH: 107
<212> TYPE: PRT
<213> ORGANISM: Human immunodeficiency virus type 1

<400> SEQUENCE: 105

```
Met Ala Gly Arg Ser Gly Asp Ser Asp Glu Ala Leu Leu Gln Ala Val
 1               5                  10                  15
Arg Ile Val Lys Ile Leu Tyr Gln Ser Asn Pro Tyr Pro Lys Pro Glu
                20                  25                  30
Gly Thr Arg Gln Ala Arg Lys Asn Arg Arg Arg Arg Trp Arg Ala Arg
             35                  40                  45
Gln Arg Gln Ile His Ser Ile Ser Glu Arg Ile Leu Val Thr Cys Leu
         50                  55                  60
Gly Arg Pro Thr Glu Pro Val Pro Leu Gln Leu Pro Pro Ile Glu Arg
 65                  70                  75                  80
Leu His Ile Asn Cys Ser Glu Ser Ser Gly Thr Ser Gly Thr Gln Gln
                 85                  90                  95
Ser Gln Gly Thr Thr Glu Gly Val Gly Asn Pro
            100                 105
```

<210> SEQ ID NO 106
<211> LENGTH: 107
<212> TYPE: PRT
<213> ORGANISM: Human immunodeficiency virus type 1

<400> SEQUENCE: 106

```
Met Ala Gly Arg Ser Gly Asp Ser Asp Glu Ala Leu Leu Gln Ala Val
1               5                   10                  15

Arg Ile Ile Lys Ile Leu Tyr Gln Ser Asn Pro Tyr Pro Lys Pro Glu
            20                  25                  30

Gly Thr Arg Gln Ala Arg Lys Asn Arg Arg Arg Arg Trp Arg Ala Arg
        35                  40                  45

Gln Arg Gln Ile His Ser Ile Ser Glu Arg Ile Leu Ser Thr Val Leu
    50                  55                  60

Gly Arg Pro Thr Glu Pro Val Pro Leu Gln Leu Pro Pro Ile Glu Arg
65                  70                  75                  80

Leu His Ile Asn Cys Ser Glu Ser Ser Gly Thr Ser Gly Thr Gln Gln
                85                  90                  95

Ser Gln Gly Thr Thr Glu Gly Val Gly Asn Pro
            100                 105
```

<210> SEQ ID NO 107
<211> LENGTH: 107
<212> TYPE: PRT
<213> ORGANISM: Human immunodeficiency virus type 1

<400> SEQUENCE: 107

```
Met Ala Gly Arg Ser Gly Asp Ser Asp Glu Ala Leu Leu Gln Ala Val
1               5                   10                  15

Arg Ile Ile Lys Ile Leu Tyr Gln Ser Asn Pro Tyr Pro Lys Pro Glu
            20                  25                  30

Gly Thr Arg Gln Ala Gln Lys Asn Arg Arg Arg Arg Trp Arg Ala Arg
        35                  40                  45

Gln Arg Gln Ile His Ser Ile Ser Glu Arg Ile Leu Ser Thr Cys Leu
    50                  55                  60

Gly Arg Pro Ala Glu Pro Val Pro Leu Gln Leu Pro Pro Ile Glu Arg
65                  70                  75                  80

Leu Cys Ile Asp Cys Ser Glu Ser Ser Gly Thr Ser Gly Thr Gln Gln
                85                  90                  95

Ser Gln Gly Thr Thr Glu Gly Val Gly Ser Cys
            100                 105
```

<210> SEQ ID NO 108
<211> LENGTH: 36
<212> TYPE: PRT
<213> ORGANISM: Human immunodeficiency virus type 1

<400> SEQUENCE: 108

```
Met Glu Pro Ile Asp Pro Asn Leu Glu Pro Trp Asn His Pro Gly Ser
1               5                   10                  15

Gln Pro Asn Thr Pro Cys Asn Lys Cys Tyr Cys Lys Tyr Cys Ser Tyr
            20                  25                  30

His Cys Leu Val
        35
```

<210> SEQ ID NO 109
<211> LENGTH: 26
<212> TYPE: PRT
<213> ORGANISM: Human immunodeficiency virus type 1

<400> SEQUENCE: 109

```
Cys Lys Tyr Cys Ser Tyr His Cys Leu Val Cys Phe Gln Thr Lys Gly
1               5                   10                  15
```

```
Leu Gly Ile Ser Tyr Gly Arg Lys Lys Arg
                20                  25

<210> SEQ ID NO 110
<211> LENGTH: 59
<212> TYPE: PRT
<213> ORGANISM: Human immunodeficiency virus type 1

<400> SEQUENCE: 110

Leu Gly Ile Ser Tyr Gly Arg Lys Lys Arg Arg Gln Arg Arg Ser Thr
1               5                   10                  15

Pro Pro Ser Ser Glu Asp His Gln Asn Pro Ile Ser Lys Gln Pro Leu
                20                  25                  30

Pro Gln Thr Arg Gly Asp Pro Thr Gly Ser Glu Glu Ser Lys Lys Lys
            35                  40                  45

Val Glu Ser Lys Thr Lys Thr Asp Pro Phe Asp
    50                  55

<210> SEQ ID NO 111
<211> LENGTH: 122
<212> TYPE: PRT
<213> ORGANISM: Human immunodeficiency virus type 1

<400> SEQUENCE: 111

Leu Gly Ile Ser Tyr Gly Arg Lys Lys Arg Arg Gln Arg Arg Ser Thr
1               5                   10                  15

Pro Pro Ser Ser Glu Asp His Gln Asn Pro Ile Ser Lys Gln Pro Leu
                20                  25                  30

Pro Gln Thr Arg Gly Asp Pro Thr Gly Ser Glu Glu Ser Lys Lys Lys
            35                  40                  45

Val Glu Ser Lys Thr Lys Thr Asp Pro Phe Asp Cys Lys Tyr Cys Ser
    50                  55                  60

Tyr His Cys Leu Val Cys Phe Gln Thr Lys Gly Leu Gly Ile Ser Tyr
65                  70                  75                  80

Gly Arg Lys Lys Arg Met Glu Pro Ile Asp Pro Asn Leu Glu Pro Trp
                85                  90                  95

Asn His Pro Gly Ser Gln Pro Asn Thr Pro Cys Asn Lys Cys Tyr Cys
                100                 105                 110

Lys Tyr Cys Ser Tyr His Cys Leu Val Ser
            115                 120
```

HIV-1 SUBTYPE ISOLATE REGULATORY/ACCESSORY GENES, AND MODIFICATION AND DERIVATIVES THEREOF

CROSS REFERENCE TO RELATED APPLICATIONS

This application is a divisional application of co-pending U.S. non-provisional patent application Ser. No. 10/494,131, filed Aug. 24, 2004, now U.S. Pat. No. 7,479,547, which is a U.S. National Phase of PCT/IB02/04550, filed on Oct. 31, 2002, which claims priority to South African Patent Application No. 2001/8978, filed on Oct. 31, 2001. The contents of each of these applications are hereby incorporated by reference in their entirety.

BACKGROUND TO THE INVENTION

THIS invention relates to a process for the selection of HIV-1 subtype (clade) C isolate regulatory/accessory genes, selected HIV-1 subtype C isolate regulatory/accessory genes and modifications and derivatives thereof for use in prophylactic and therapeutic vaccines to produce proteins and polypeptides for the purpose of eliciting protection against HIV infection or disease.

The disease acquired immunodeficiency syndrome (AIDS) is caused by human immunodeficiency virus (HIV). Over 34 million people worldwide are thought to be living with HIV/AIDS, with over 95% of infected people living in developing countries (UNAIDS, 1999). It is estimated that 24.5 million infected people reside in sub-Saharan Africa and that South Africa currently has one of the world's fastest growing HIV-1 epidemics. At the end of 2000, over 24% of pregnant women attending government antenatal clinics in South Africa were HIV positive (Department of Health, 2001). A preventative vaccine is considered to be the only feasible way to control this epidemic in the long term.

HIV shows remarkable genetic diversity that has confounded the development of a vaccine. The molecular basis of variation resides in the viral enzyme reverse transcriptase which not only introduces an error every round of replication, but also promotes recombination between viral RNAs. Based on phylogenetic analysis of sequences, HIV has been classified into a number of groups: the M (major group) which comprises subtypes A to H and K, the O (outlier group) and the N (non-M, non-O group). Recently recombinant viruses have been more frequently identified and there are a number which have spread significantly and established epidemics (circulating recombinant forms or CRF) such as subtype A/G recombinant in West Africa, and CRF A/E recombinant in Thailand (Robertson et al., 2000).

Subtype C predominates in the Southern African region which includes Botswana, Zimbabwe, Zambia, Malawi, Mozambique and South Africa. In addition, increasing numbers of subtype C infections are being detected in the Southern region of Tanzania. This subtype also predominates in Ethiopia and India and is becoming more important in China.

A possible further obstacle to vaccine development is that the biological properties of HIV change as disease progresses. HIV requires two receptors to infect cells, the CD4 and co-receptors of which CCR5 and CXCR4 are the major co-receptors used by HIV-1 strains. The most commonly transmitted phenotype is non-syncytium inducing (NSI), macrophage-tropic viruses that utilise the CCR5 co-receptor for entry (R5 viruses). Langerhans cells in the mucosa are thought to selectively pick up R5 variants at the portal of entry and transport them to the lymph nodes where they undergo replication and expansion. As the infection progresses, viruses evolve that have increased replicative capacity and the ability to grow in T cell lines. These syncytium-inducing (SI) T-tropic viruses use CXCR4 in conjunction with or in preference to CCR5, and in some cases also use other minor co-receptors (Connor et al., 1997, Richman & Bozzette, 1994). However HIV-1 subtype C viruses appear to be unusual in that they do not readily undergo this phenotypic switch, as R5 viruses are also predominant in patients with advanced AIDS (Bjorndal et al., 1999, Peeters et al., 1999, Tscherning et al., 1998, Scarlatti et al., 1997).

An HIV vaccine aims to elicit both a CD8+ cytotoxic T lymphocyte (CTL) immune response as well as a neutralizing antibody response. Many current vaccine approaches have primarily focused on inducing a CTL response. It is thought that the CTL response may be more important as it is associated with the initial control of viral replication after infection, as well as control of replication during disease, and is inversely correlated with disease progression (Koup et al., 1994, Ogg et al., 1999 Schmitz et al., 1999). The importance of CTL in protecting individuals from infection is demonstrated by their presence in highly exposed seronegative individuals, for example certain sex-workers in Kenya (Rowland-Jones et al., 1998).

Knowledge of genetic diversity is highly relevant to the design of vaccines aiming at eliciting a cytotoxic T-lymphocyte (CTL) response. There are many CTL epitopes in common between viruses (HIV Molecular Immunology Database, 1998). In addition, several studies have now shown that there is a cross-reactive CTL response: individuals vaccinated with a subtype B-based vaccine could lyse autologous targets infected with a diverse group of isolates (Ferrari et al., 1997); and CTLs from non-B infected individuals could lyse subtype B-primed targets (Betts et al. 1997; Durali et al, 1998). A comparison of CTL epitopes in the HIV-1 sequence database indicated that there is a greater conservation of cytotoxic T epitopes within a subtype compared to between subtypes and that there will be a greater chance of a CTL response if the challenge virus is the same subtype as the vaccine strain.

It is thought that the regulatory genes of HIV are extremely important in eliciting an immune response. Tat, Rev and Nef are all expressed early in the infectious cycle and would thus provide targets for cytotoxic T lymphocytes (CTLs) early in infection, possibly allowing virus infected cells to be destroyed before the virus can spread (Klotman et. al., 1991; Addo et. al., 2001). In addition, there is promising data showing that the Tat protein elicits an effective immune response in HIV-infected, asymptomatic people (Calarota et. al., 1999; Calarota et. al., 2001). It has recently been reported that the Tat protein is one of the first to undergo escape from CTL in infected macaques (Allen et. al., 2000). This indicates that there is immune pressure on tat and that there is an early response to the Tat protein.

Viral strains used in the design of a vaccine need to be shown by genotypic analysis to be representative of the circulating strains and not an unusual or outlier strain. In addition, it is important that a vaccine strain also has the phenotype of a recently transmitted virus, which is NSI and uses the CCR5 co-receptor.

DEFINITIONS

In the specification which follows, certain terms are intended to have the following meanings:

"wild-type" means the naturally occurring HIV codon bias of the virus isolate;
"codon optimised" means the resynthesis of the gene using a human codon bias instead of the HIV codon bias;
"truncated" means having the first ten amino acids removed from the Nef protein to inactivate function whilst maintaining immunogenicity;
"shuffled" means the rearrangement of the Tat protein in order to inactivate function whilst maintaining immunogenicity.

SUMMARY OF THE INVENTION

According to a first aspect of the invention a molecule is provided, the molecule having:
  (i) the nucleotide sequence as set out in FIG. 1 (SEQ I.D. No. 1);
  (ii) an RNA sequence corresponding to the nucleotide sequence set out in FIG. 1 (SEQ I.D. No. 1);
  (iii) a sequence which is at least 97% DNA similar to the nucleotide sequence set out in FIG. 1 (SEQ I.D. No. 1) or an RNA sequence corresponding to it, and which displays substantially similar immunogenicity;
  (iv) a sequence which is homologous to the nucleotide sequence set out in Sequence I.D. No. 1 or an RNA sequence corresponding to it; or
  (v) a sequence which is a modification or derivative of the sequence of any one of (i) to (iv).

The modified sequence is preferably that set out in either one of FIGS. 9 and 10, which are consensus sequences of Du422 and Du151 (SEQ I.D. Nos. 9 and 10).

According to another aspect of the invention a molecule is provided, the molecule having:
  (i) the nucleotide sequence set out in FIG. 3 (SEQ I.D. No. 3);
  (ii) an RNA sequence corresponding to the nucleotide sequence set out in FIG. 3 (SEQ I.D. No. 3);
  (iii) a sequence which is at least 97% DNA similar to the nucleotide sequence set out in FIG. 3 (SEQ I.D. No. 3) or an RNA sequence corresponding to it, and which displays substantially similar immunogenicity;
  (iv) a sequence which is homologous to the nucleotide sequence set out in FIG. 3 (SEQ I.D. No. 3) or an RNA sequence corresponding to it; or
  (v) a sequence which is a modification or derivative of the sequence of any one of (i) to (iv).

The modified sequence is preferably that set out in either one of FIGS. 9 and 10, which are consensus sequences of Du422 and Du151 (SEQ I.D. No. 9 and No. 10).

According to another aspect of the invention a molecule is provided, the molecule having:
  (i) the nucleotide sequence set out in FIG. 5 (SEQ I.D. No. 5);
  (ii) an RNA sequence corresponding to the nucleotide sequence set out in FIG. 5 (SEQ I.D. No. 5);
  (iii) a sequence which is at least 98% DNA similar to the nucleotide sequence set out in FIG. 5 (SEQ I.D. No. 5) or an RNA sequence corresponding to it, and which displays substantially similar immunogenicity;
  (iv) a sequence which is homologous to the nucleotide sequence set out in FIG. 5 (SEQ I.D. No. 5) or an RNA sequence corresponding to it; or
  (v) a sequence which is a modification or derivative of the sequence of any one of (i) to (iv).

The modified sequence is preferably that set out in either one of FIGS. 12 and 13 (SEQ I.D. Nos. 12 and 13).

According to another aspect of the invention a molecule is provided, the molecule having:
  (i) the nucleotide sequence set out in FIG. 7 (SEQ I.D. No. 7);
  (ii) an RNA sequence corresponding to the nucleotide sequence set out in FIG. 7 (SEQ I.D. No. 7);
  (iii) a sequence which is at least 96% DNA similar to the nucleotide sequence set out in FIG. 7 (SEQ I.D. No. 7) or an RNA sequence corresponding to it, and which displays substantially similar immunogenicity;
  (iv) a sequence which is homologous to the nucleotide sequence set out in FIG. 7 (SEQ I.D. No. 7) or an RNA sequence corresponding to it; or
  (v) a sequence which is a modification or derivative of the sequence of any one of (i) to (iv).

The modified sequence preferably has similar or the same modifications as those set out in either one of FIGS. 12 and 13 (SEQ I.D. Nos. 12 and 13) for the nef gene of the isolate Du151.

According to another aspect of the invention a molecule is provided, the molecule having:
  (i) the nucleotide sequence set out in FIG. 15 (SEQ I.D. No. 15);
  (ii) an RNA sequence corresponding to the nucleotide sequence set out in FIG. 15 (SEQ I.D. No. 15);
  (iii) a sequence which is at least 90% or greater DNA similar to the nucleotide sequence set out in FIG. 15 (SEQ I.D. No. 15) or an RNA sequence corresponding to it, and which displays substantially similar immunogenicity;
  (iv) a sequence which is homologous to the nucleotide sequence set out in FIG. 15 (SEQ I.D. No. 15) or an RNA sequence corresponding to it; or
  (v) a sequence which is a modification or derivative of the sequence of any one of (i) to (iv).

According to another aspect of the invention a molecule is provided, the molecule having:
  (i) the nucleotide sequence set out in FIG. 17 (SEQ I.D. No. 17);
  (ii) an RNA sequence corresponding to the nucleotide sequence set out in FIG. 17 (SEQ I.D. No. 17);
  (iii) a sequence which is at least 90% DNA similar to the nucleotide sequence set out in FIG. 17 (Sequence I.D. No. 17) or an RNA sequence corresponding to it, and which displays substantially similar immunogenicity;
  (iv) a sequence which is homologous to the nucleotide sequence set out in FIG. 17 (SEQ I.D. No. 17) or an RNA sequence corresponding to it; or
  (v) a sequence which is a modification or derivative of the sequence of any one of (i) to (iv).

According to another aspect of the invention a polypeptide is provided, the polypeptide having:
  (i) the amino acid sequence set out in FIG. 2 (SEQ I.D. No. 2);
  (ii) a sequence which is at least 95% similar to the sequence of FIG. 2 and which has substantially similar immunogenicity; or
  (iii) a sequence which is a modification or derivative of the amino acid sequence set out in FIG. 2 (SEQ I.D. No. 2).

The modified sequence is preferably that set out in FIG. 11, which is a consensus sequence of Du422 and Du151 (SEQ I.D. No. 11).

According to another aspect of the invention a polypeptide is provided, the polypeptide having:
  (i) the amino acid sequence set out in FIG. 4 (SEQ I.D. No. 4);
  (ii) a sequence which is at least 95% similar to the sequence of FIG. 4 and which has substantially similar immunogenicity; or (iii) a sequence which is a modification or derivative of the amino acid sequence set out in FIG. 4 (SEQ I.D. No. 4).

The modified sequence is preferably that set out in FIG. 11, which is a consensus sequence of Du422 and Du151 (SEQ I.D. No. 11).

According to another aspect of the invention a polypeptide is provided, the polypeptide having:
(i) the amino acid sequence set out in FIG. 6 (SEQ I.D. No. 6);
(ii) a sequence which is at least 92% similar to the sequence of FIG. 6 and which has substantially similar immunogenicity; or
(iii) a sequence which is a modification or derivative of the amino acid sequence set out in FIG. 6 (SEQ I.D. No. 6).

The modified sequence is preferably that set out in FIG. 14 (SEQ I.D. No. 14).

According to another aspect of the invention a polypeptide is provided, the polypeptide having:
(i) the amino acid sequence set out in FIG. 8 (SEQ I.D. No. 8);
(ii) a sequence which is at least 95% similar to the sequence of FIG. 8 and which has substantially similar immunogenicity; or
(iii) a sequence which is a modification or derivative of the amino acid sequence set out in FIG. 8 (SEQ I.D. No. 8).

The modified sequence preferably has similar or the same modifications as those set out in FIG. 14 (SEQ I.D. No. 14) for the amino acid sequence of the nef gene of the isolate Du151.

According to another aspect of the invention a polypeptide is provided, the polypeptide having:
(i) the amino acid sequence set out in FIG. 16 (SEQ I.D. No. 16);
(ii) a sequence which is at least 90% similar to the sequence of FIG. 16 and which has substantially similar immunogenicity; or
(iii) a sequence which is a modification or derivative of the amino acid sequence set out in FIG. 16 (SEQ I.D. No. 16).

According to another aspect of the invention a consensus amino acid sequence for the tat gene of HIV-1 subtype C is the following:

(SEQ ID NO: 18)

MEPVDPNLEPWNHPGSQPKTACNKCYCKHCSYHCLVCFQTKGLGISYGRKKRRQRRSAPP$^{60}$

SSEDHQNLISKQPLPQTRGDPTGSEESKKKVESKTETDPFD$^{101}$

According to another aspect of the invention a consensus amino acid sequence for the partial nef gene of HIV-1 subtype C is the following:

MGGKWSKSSIVGWPAVRERIRRTEPAAEGVGAASQDLDKHGALTSSNTAHNNADCAWLQA$^{60}$ (SEQ ID No: 19)

QEEEEEVGFPVRPQVPLRPMTYKGAFDLSFFLKEKGGLEGLIYSKKRQEILDLWVYHTQG$^{120}$

FFPDWQNYTPGPGVRYPLTFGWCFKLVPVDPREVEEANEGENNCLLHPMSQHGMEDEDRE$^{180}$

VLKWKFDSSLARRHMARELHPEYYKDC$^{207}$

According to another aspect of the invention a consensus amino acid sequence for the partial rev gene of HIV-1 subtype C is the following:

(SEQ ID NO: 20)

MAGRSGDSDEALLQAVRIIKILYQSNPYPKPEGTRQARKNRRRRWRARQRQIHSISERIL$^{60}$

STCLGRPAEPVPLQLPPIERLHIDCSESSGTSGTQQSQQTTEGVGSP$^{107}$

According to a further aspect of the invention, there is provided the use of at least one of the sequences described above in the manufacture of a vaccine for use in the treatment or prevention of HIV infection. Preferably, at least two of the sequences are used in the vaccine.

According to a further aspect of the invention, there is provided a vaccine comprising at least two of the sequences described above.

According to a further aspect of the invention, there is provided a vaccine comprising at least portions of a gag gene sequence, a reverse transcriptase (pol) gene sequence; a shuffled tat gene sequence and a truncated nef gene sequence which have been ligated to form an in frame polygene designated grttnC (SEQ I.D. No: 30).

The vaccine may be for the treatment or prevention of HIV.

DESCRIPTION OF THE DRAWINGS

FIG. 1 (SEQ ID NO:1) shows the nucleic acid sequence (cDNA) of the sequenced tat gene of the isolate Du422.

FIG. 2 (SEQ ID NO:2) shows the amino acid sequence of the sequenced tat gene of the isolate Du422, derived from the nucleic acid sequence.

FIG. 3 (SEQ ID NO:3) shows the nucleic acid sequence (cDNA) of the sequenced tat gene of the isolate Du151.

FIG. 4 (SEQ ID NO:4) shows the amino acid sequence of the sequenced tat gene of the isolate Du151, derived from the nucleic acid sequence.

FIG. 5 (SEQ ID NO:5) shows the nucleic acid sequence (cDNA) of the sequenced nef gene of the isolate Du151.

FIG. 6 (SEQ ID NO:6) shows the amino acid sequence of the sequenced nef gene of the isolate Du151, derived from the nucleic acid sequence.

FIG. 7 (SEQ ID NO:7) shows the nucleic acid sequence of the sequenced rev gene of the isolate Du422, derived from the nucleic acid sequence.

FIG. 8 (SEQ ID NO:8) shows the amino acid sequence of the sequenced rev gene of the isolate Du422, derived from the nucleic acid sequence.

FIG. 9 (SEQ ID NO:9) shows the nucleic acid sequence (DNA) of the wild-type, shuffled, sequenced tat gene of a consensus of the isolates Du422 and Du151.

FIG. 10 (SEQ ID NO:10) shows the nucleic acid sequence (DNA) of the codon optimised, shuffled, sequenced tat gene of a consensus of the isolates Du422 and Du151 for the purposes of increased expression.

FIG. 11 (SEQ ID NO: 11) shows the amino acid sequence of the shuffled, sequenced Tat protein of a consensus of the isolates Du422 and Du151.

FIG. 12 (SEQ ID NO:12) shows the nucleic acid sequence (DNA) of the wild-type, truncated, sequenced nef gene of the isolate Du151.

FIG. 13 (SEQ ID NO:13) shows the nucleic acid sequence (DNA) of codon optimised, truncated, sequenced nef gene of the isolate Du151 for the purposes of increased expression.

FIG. 14 (SEQ ID NO:14) shows the amino acid sequence of the truncated, sequenced Nef protein of the isolate Du151.

FIG. 15 (SEQ ID NO:15) shows the nucleic acid sequence (DNA) of the wild-type polygene consisting of shuffled (SEQ ID NO:9)-truncated nef (SEQ ID NO: 11) genes of the isolates Du422 and Du151.

FIG. 16 (SEQ ID NO:16) shows the amino acid sequence of the sequenced shuffled Tat (SEQ I.D. No 10)-truncated Nef (SEQ ID NO:12) polyprotein of the isolates Du422 and Du151.

FIG. 17 (SEQ ID NO:17) shows the nucleic acid sequence (DNA) of the sequenced polygene consisting of shuffled tat-truncated nef genes of the isolates Du422 and Du151 modified to reflect human codon usage for the purposes of increased expression.

FIG. 32b shows an amino acid sequence of GrttnC, made up of gag (Du422), RT (Du151), shuffled tat and truncated nef (SEQ ID NO:16) (SEQ ID NO:30).

FIG. 34 shows the Du422 gag nucleotide sequence which forms part of grttnC (SEQ ID NO:31).

FIG. 35 shows the Du422 Gag amino acid sequence which forms part of grttnC (SEQ ID NO:32).

FIG. 36 shows the Du151 reverse transcriptase (RT) nucleotide sequence which forms part of grttnC (SEQ ID NO:33).

FIG. 37 shows the Du151 reverse transcriptase (RT) amino acid sequence which forms part of grttnC (SEQ ID NO:34).

DETAILED DESCRIPTION OF THE INVENTION

Figure 18:
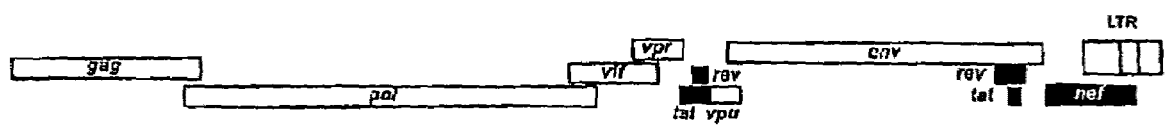
FIG. 18 shows a schematic representation of the HIV-1 genome.

This invention relates to the selection of HIV-1 subtype C isolate regulatory and accessory genes and the use of these genes and modifications and derivatives thereof in making prophylactic and therapeutic pharmaceutical compositions and formulations, and in particular vaccines against HIV-1 subtype C. The compositions could therefore be used either prophylactically to prevent infection or therapeutically to prevent or modify disease. A number of factors must be taken into consideration in the development of an HIV vaccine and one aspect of the present invention relates to a process for the selection of suitable HIV isolates accessory and regulatory genes that may be used in the development of a vaccine.

The applicant envisages that the vaccine developed according to the above method could be used against one or more HIV subtypes as well as HIV-1 subtype C.

A process was developed to identify appropriate strains for use in developing a vaccine for HIV-1 subtype C. Viral isolates from acutely infected individuals were collected. They were sequenced in the tat, rev and nef regions and the amino acid sequences for the tat, rev and nef genes from these isolates were compared. A consensus sequence, the South African consensus sequence, was then formed by selecting the most frequently appearing amino acid at each position. The consensus sequence for each of the tat, rev and nef genes of HIV-1 subtype C also forms an aspect of the invention. Appropriate strains for vaccine development were then selected from these isolates by comparing them with the consensus sequence and characterising them phenotypically. The isolates also form an aspect of the invention.

In order to select for NSI strains which use the CCR5 co-receptor, a well established sex worker cohort was used to identify the appropriate strains. Appropriate strains were identified from acutely infected individuals by comparing them with the consensus sequence which had been formed. Viral isolates from 12 acutely infected individuals were sequenced in the tat, rev and/or nef regions and phenotypically characterised. These sequences were compared with viral isolates from 15 asymptomatic individuals from another region having more than 500 CD4 cells, as well as 11 viral isolates from AIDS patients attending a TB infectious disease hospital in Gauteng (n=9) and two children with AIDS (n=2). Other published subtype C sequences located in the Los Alamos Database were also included (http://www.hiv-web.lanl.gov/).

Two potential vaccine strains, designated Du422 and Du151 were selected. Du422 and Du151 were selected based on amino acid homology to the consensus sequence in all three gene regions: tat, rev and nef, CCR5 tropism and ability to grow and replicate in tissue culture. The nucleotide and amino acid sequences of the three gene regions of the three isolates and modifications and derivatives thereof also form aspects of the invention.

The Isolation and Selection of Viral Strains for the Design of a Vaccine

The following criteria were used to select appropriate strains for inclusion into HIV-1 vaccines for Southern Africa:
that the strains be genotypically representative of circulating strains;
that the strain not be an outlier strain;
that the strain be as close as possible to the consensus amino acid sequence developed according to the invention for the tat, rev and nef genes of HIV-1 subtype C;
that the strain have an R5 phenotype, i.e. a phenotype associated with transmission for selection; and
that the vaccine be able to be grown in tissue culture.

The following procedure was followed in the selection of viral strains for the design of a vaccine. A well-established sex worker cohort in Kwazulu Natal, South Africa was used to identify the appropriate strains for use in an HIV vaccine. Viral isolates from 12 acutely infected individuals were sequenced in tat, rev and nef and were also isolated and phenotypically characterised. These sequences were compared with a similar collection from asymptomatic and AIDS infected (nef region) individuals from the Gauteng region in South Africa and Cape Town region of the Western Cape as well as other published subtype C sequences.

Patients

Individuals with HIV infection were recruited from 4 regions in South Africa. Blood samples were obtained from recently infected sex workers from Kwazulu-Natal (n=12). Recent infection was defined as individuals who were previously seronegative and had became seropositive within the previous year. Samples were also collected from individuals attending out-patients clinics in Cape Town (n=2), women attending ante-natal clinics in Johannesburg (n=6) and men attending a STD clinic on a gold mine outside Johannesburg (n=7). The latter 2 groups were clinically stable and were classified as asymptomatic infections. In addition, for comparison in the nef gene, 11 isolates from AIDS patients were included from Gauteng; 9 isolates from patients attending a TB infectious disease hospital and 2 isolates from children infected with AIDS. Blood samples were collected in EDTA and used to determine the CD4 T cell count and genetic analysis of the virus. In the case of recent infections a branched chain (bDNA) assay (Chiron) to measure plasma viral load was done, and the virus was isolated. HIV-1 serostatus was determined by ELISA. The results of the CD4 T cell counts and the viral loads on the sex workers were established and information on the clinical status as at date of seroconversion, CD4, and data on the co-receptor usage is set out in Table 1 below.

Virus Isolation

HIV was isolated from peripheral blood mononuclear cells (PBMC) using standard co-culture techniques with mitogen-activated donor PBMC. $2 \times 10^6$ patient PBMC were co-cultured with $2 \times 10^6$ donor PBMC in 12 well plates with 2 ml RPMI 1640 with 20% FCS, antibiotics and 5% IL-2 (Boehringer). Cultures were replenished twice weekly with fresh medium containing IL-2 and once with $5 \times 10^5$/ml donor PBMC. Virus growth was monitored weekly using a commercial p24 antigen assay (Coulter). Antigen positive cultures were expanded and cultured for a further 2 weeks to obtain 40 ml of virus containing supernatant which was stored at −70°

C. until use. The results of the isolation of the viruses from the commercial sex workers is also shown in Table 1 below.

Viral Phenotypes

Virus-containing supernatant was used to assess the biological phenotype of viral isolates on MT-2 and co-receptor transfected cell lines. For the MT-2 assay, 500 μl of supernatant was incubated with $5 \times 10^4$ MT-2 cells in PRMI plus 10% FCS and antibiotics. Cultures were monitored daily for syncitia formation over 6 days. U87.CD4 cell expressing either the CCR5 or CXCR4 co-receptor were grown in DMEM with 10% FCS, antibiotics, 500 μg/ml G418 and 1 μg/ml puromycin. GHOST cells expressing minor co-receptors were grown in DMEM with 10% FCS, 500 μg/ml G418, 1 μg/ml puromycin and 100 μg/ml hygromycin. Cell lines were passaged twice weekly by trypsination. Co-receptor assays were done in 12 well plates; $5 \times 10^4$ cells were plated in each well and allowed to adhere overnight. The following day 500 μl of virus containing supernatant was added and incubated overnight to allow viral attachment and infection and washed three times the following day. Cultures were monitored on days 4, 8 and 12 for syncitia formation and p24 antigen production. Cultures that showed evidence of syncitia and increasing concentrations of p24 antigen were considered positive for viral growth. The results of co-receptor usage of the viruses from the commercial sex workers are also shown in Table 1.

reverse primers (5'CCT TCA GCT ACT GCT ATT GC3' (SEQ ID No: 28) 8689-8698 bp).

The amplified DNA fragments were purified using the QIAQUICK PCR Purification Kit (Qiagen, Germany). The DNA fragments were then sequenced using the upstream PCR primers as sequencing primers. Sequencing was done using the Sanger dideoxyterminator strategy with fluorescent dyes attached to the dideoxynucleotides. The sequence determination was made by electrophoresis using an ABI 377 Sequencer. A mapped illustration of an HIV-1 proviral genome showing the tat, rev and nef genes sequenced as described above, is shown in FIG. 18.

Genotypic Characterisation

To select the vaccine isolate or isolates, a survey covering the three HIV genes tat (101 codons, 306 bases), rev (107 contiguous codons, 324 bases) and nef (207 codons, 618 bases) was done (FIG. 18). The map of FIG. 18 shows the 5' long terminal repeat, the structural and functional genes (gag, pol and env) as well as the regulatory and accessory proteins (vif, tat, rev, nef, vpr and vpu). The gag open reading frame illustrates the regions encoding p17 matrix protein and the p24 core protein and the p7 and p6 nuclearcapsid proteins. The pol open reading frame illustrates the protease (PR) p15, reverse transcriptase (RT) p66 and the Rnase H integrase p51. The env open reading frame indicates the region coding for gp120 and the region coding for gp41.

TABLE 1

COHORT OF ACUTE INFECTIONS FOR SELECTION OF VACCINE CANDIDATES

| Sample ID | Sero date | Sample date | Duration of infection | CD4 count | Viral load | Co-culture p24 pos | MT-2 assay | Biotype |
|---|---|---|---|---|---|---|---|---|
| Du123 | 17 Aug. 1998 | 17 Nov. 1998 | 3 mon | 841 | 19,331 | d6 (50 pg) | NSI | R5 |
| Du151 | 12 Oct. 1998 | 24 Nov. 1998 | 1.5 mon | 367 | >500,000 | d6 (>1 ng) | NSI | R5 |
| Du156 | 16 Nov. 1998 | 17 Nov. 1998 | <1 mon | 404 | 22,122 | d6 (>1 ng) | NSI | R5 |
| Du179 | 13 Aug. 1997 | 20 May 1999 | 21 mon | 394* | 1,359* | d7 (<50 pg) | SI | R5x4 |
| Du204 | 20 May 1998 | 20 May 1999 | 1 year | 633* | 8,734* | d7 (<50 pg) | NSI | R5 |
| Du258 | 3 Jun. 1998 | 22 Jun. 1999 | 1 year | 433* | 9,114* | — | No isolate | — |
| Du281 | 24 Jul. 1998 | 17 Nov. 1998 | 4 mon | 594 | 24,689 | d6 (1 ng) | NSI | R5 |
| Du285 | 2 Oct. 1998 | — | — | 560* | 161* | — | No isolate | — |
| Du368 | 8 Apr. 1998 | 24 Nov. 1998 | 7.5 mon | 670 | 13,993 | d6 (300 pg) | NSI | R5 |
| Du422 | 2 Oct. 1998 | 28 Jan. 1999 | 4 mon | 397 | 17,118* | d6 (600 pg) | NSI | R5 |
| Du457 | 17 Aug. 1998 | 17 Nov. 1998 | 3 mon | 665 | 6,658 | — | No isolate | — |
| Du467 | 26 Aug. 1998 | — | — | 671 | 19,268 | — | No isolate | — |

*date from November 1998

Sequencing

RNA was isolated from plasma and the gene fragments were amplified from RNA using reverse transcriptase to generate a cDNA followed by PCR to generate amplified DNA segments. The positions of the PCR primers are as follows, (numbering using the HIV-1 HXBr sequence): tat outer forward primer (5'GGC CGC AGA GGG AAC CAT AC3' (SEQ ID No: 21) 5584-5703 bp), or rev outer reverse primer (5'GCC CTG TCT TAT TCT TCT AGG3' (SEQ ID No: 22) 8753-8774 bp). The remaining primers used for nested PCR were as follows: the tat outer reverse primer (5'CCT CAA TAT CCC CAT CAC TCT C3' (SEQ ID No: 23) 6226-6248 bp), tat inner forward (5'TGC CAG CAT AGC AGA ATA GG3' (SEQ ID No: 24) 5785-5804 bp) and reverse (5'CTA TCA ATG CTC CTA CTC CTA ATC3' (SEQ ID No: 25) 6078-6101 bp) primers and for rev, with the rev outer forward primer (5'GAT AGT AGG AGG CTT GAT AGG3' (SEQ ID No: 26) 8285-8302 bp) and inner forward (5'GGT GTA CTC GCT ATA GTG3' (SEQ ID No: 27) 8321-8339 bp) and Of a total of 38 isolates, 12 were from the Durban cohort (DU), 24 were from Johannesburg (GG, RB, COT and SW) and 2 from Cape Town (CT). Of these 17 were sequenced in the tat gene, 17 in the rev gene and 32 in the nef gene. The isolates that were sequenced are shown in Table 2.

TABLE 2

LIST OF ISOLATES AND THE REGIONS GENES SEQUENCED

| Isolate | Tat sequence | Rev sequence | Nef sequence |
|---|---|---|---|
| CTSC1 | ✓ | — | — |
| CTSC2 | ✓ | ✓ | ✓ |
| Du123 | ✓ | ✓ | ✓ |
| Du151 | ✓ | ✓ | ✓ |
| Du156 | ✓ | ✓ | — |
| Du179 | ✓ | ✓ | ✓ |
| Du204 | ✓ | ✓ | — |
| Du258 | — | — | ✓ |
| Du281 | ✓ | ✓ | — |

TABLE 2-continued

LIST OF ISOLATES AND THE REGIONS GENES SEQUENCED

| Isolate | Tat sequence | Rev sequence | Nef sequence |
|---|---|---|---|
| Du368 | ✓ | ✓ | ✓ |
| Du422 | ✓ | ✓ | ✓ |
| Du457 | — | — | ✓ |
| Du467 | — | — | ✓ |
| GG10 | ✓ | ✓ | ✓ |
| GG2 | ✓ | — | ✓ |
| GG3 | — | — | ✓ |
| GG4 | ✓ | — | ✓ |
| GG5 | — | ✓ | ✓ |
| GG6 | — | — | ✓ |
| RB12 | ✓ | ✓ | ✓ |
| RB13 | ✓ | ✓ | ✓ |
| RB15 | — | — | ✓ |
| RB18 | — | ✓ | ✓ |
| RB21 | — | ✓ | ✓ |
| RB27 | — | ✓ | — |
| RB28 | ✓ | ✓ | ✓ |
| SW10 | — | — | ✓ |
| SW7 | — | — | ✓ |
| SW15 | — | — | ✓ |
| SW5 | — | — | ✓ |
| SW20 | — | — | ✓ |
| SW9 | — | — | ✓ |
| SW2 | — | — | ✓ |
| SW8 | — | — | ✓ |
| SW23 | — | — | ✓ |
| COT2 | — | — | ✓ |
| COT6 | — | — | ✓ |

Figure 19:
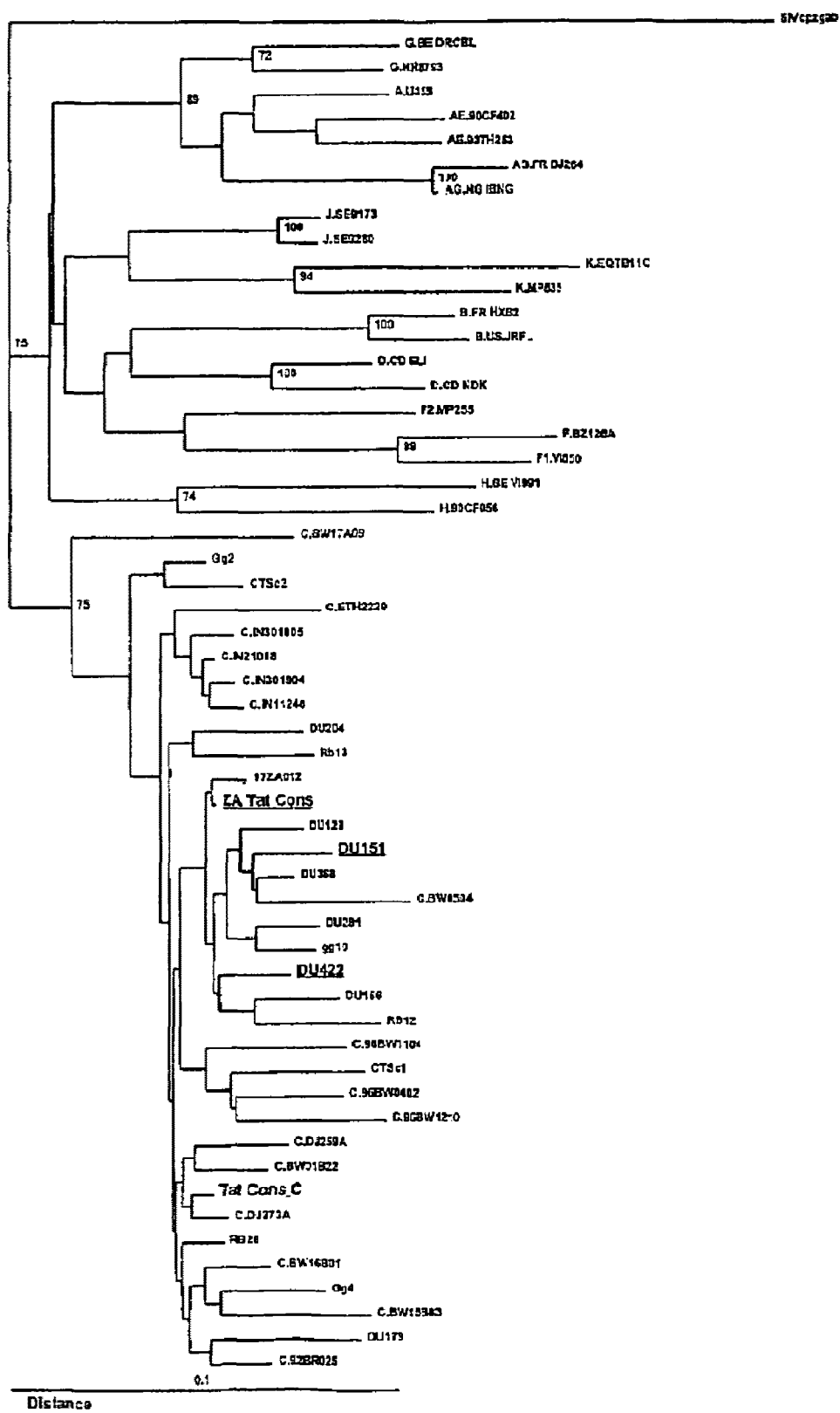
Figure 20:
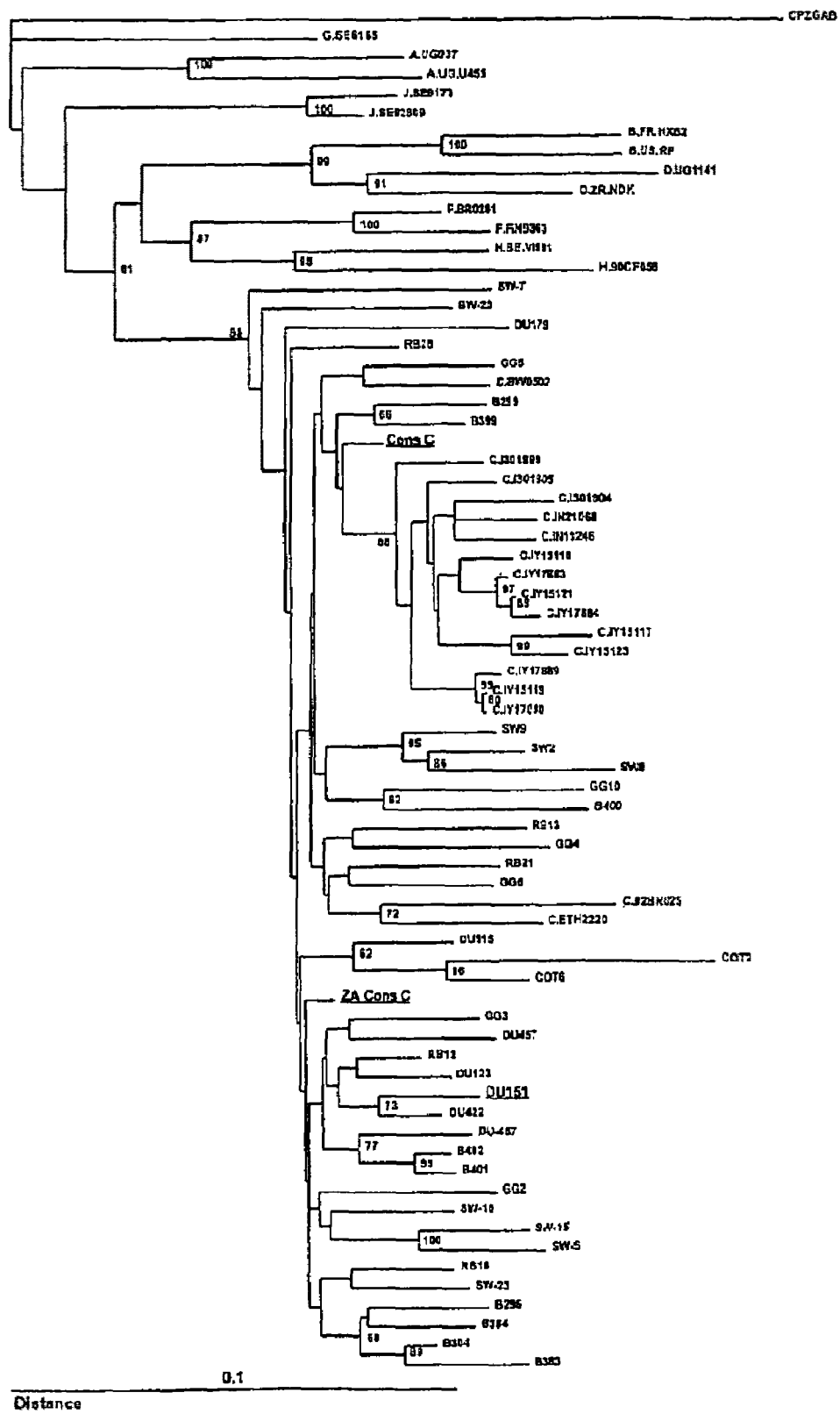
Figure 21:
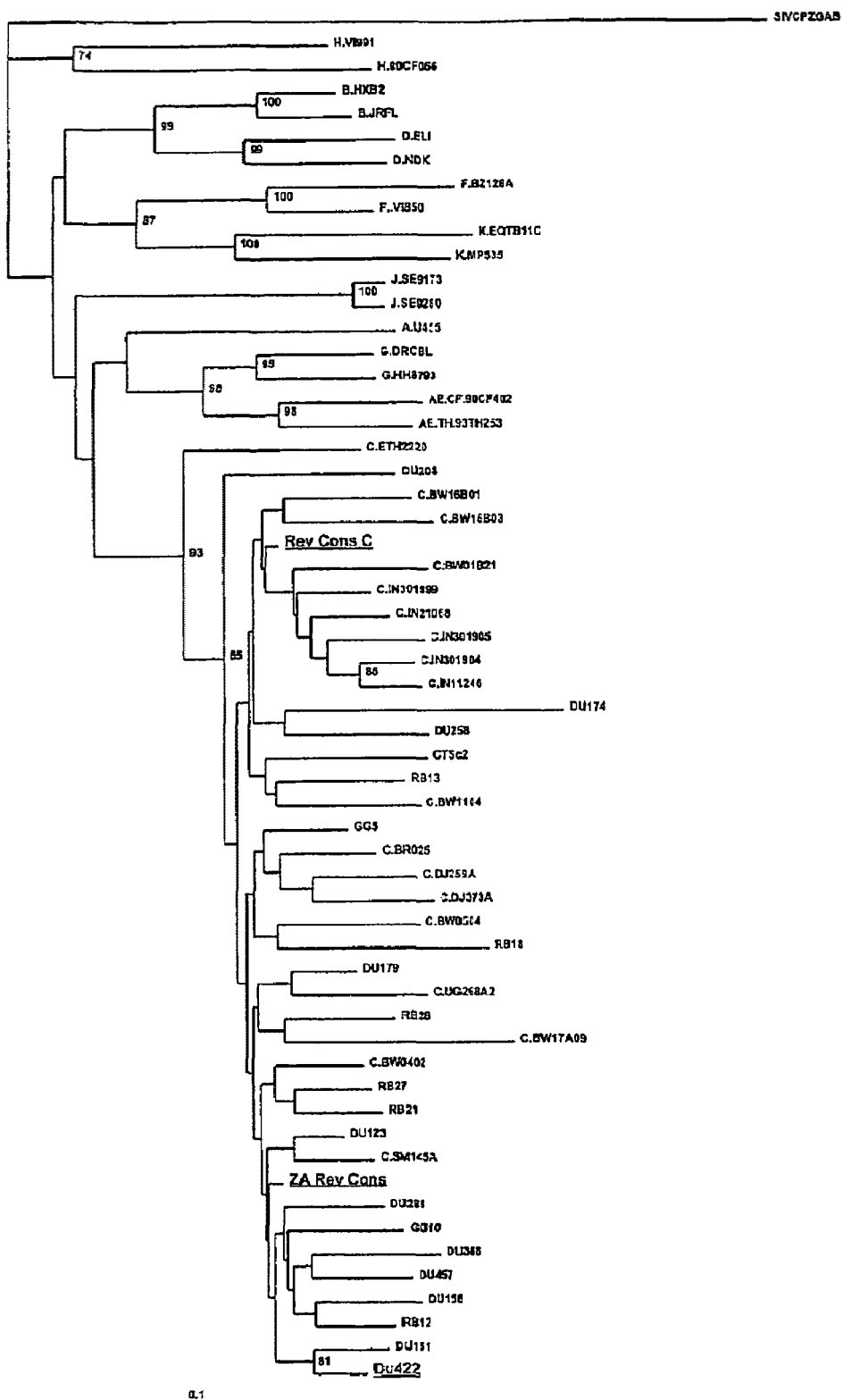
Figure 25:
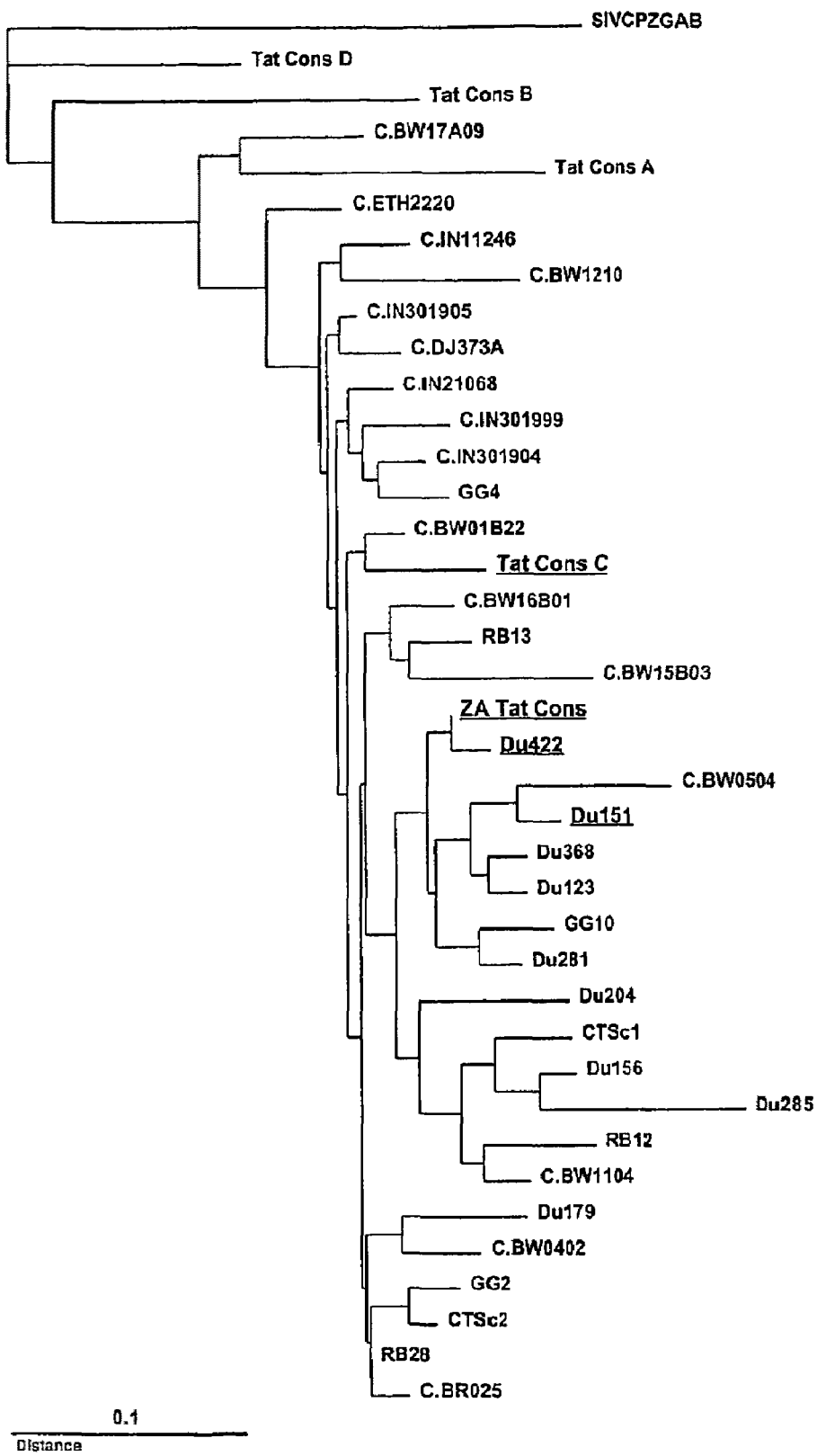
Figure 26:
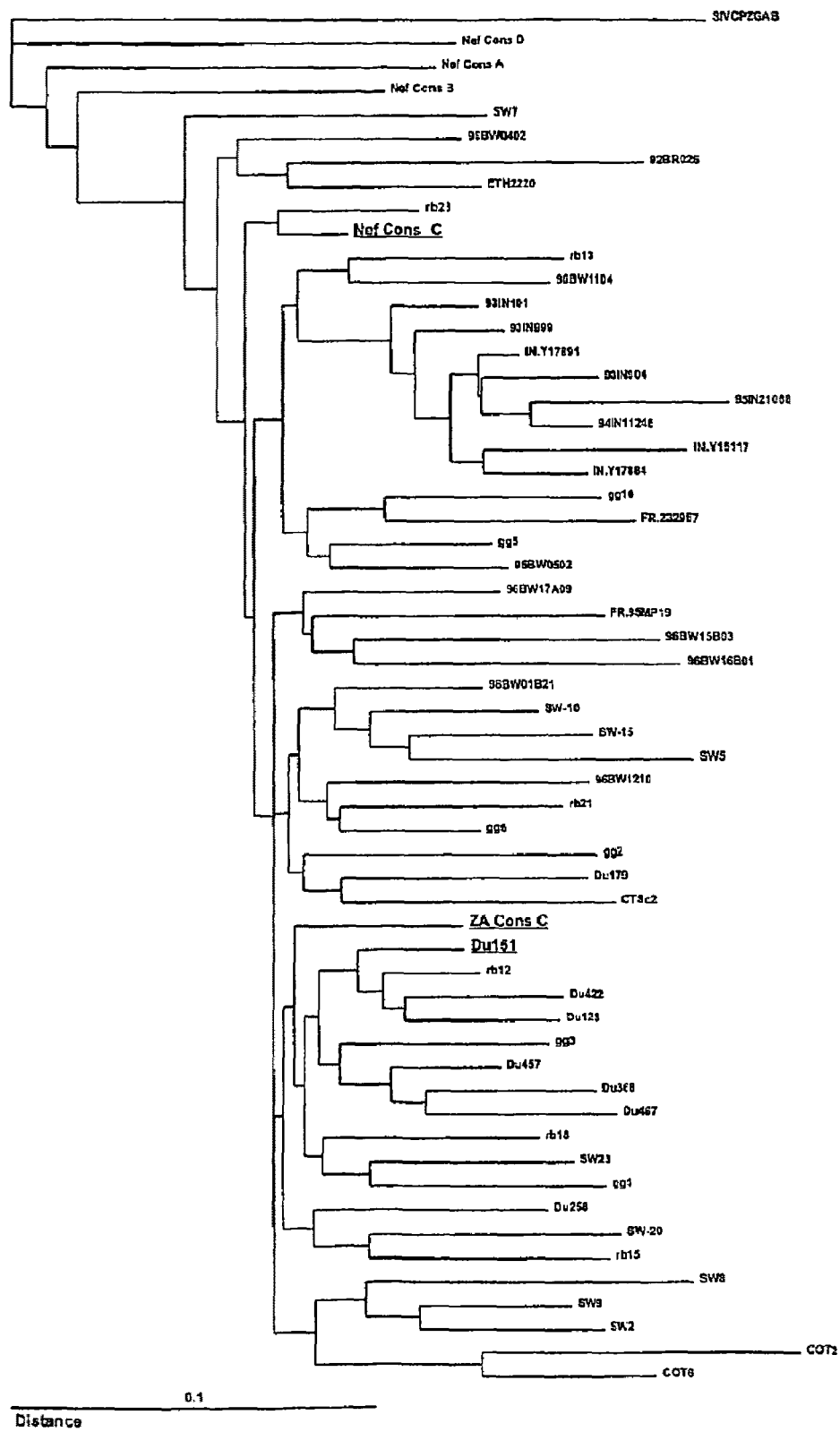
Figure 27:
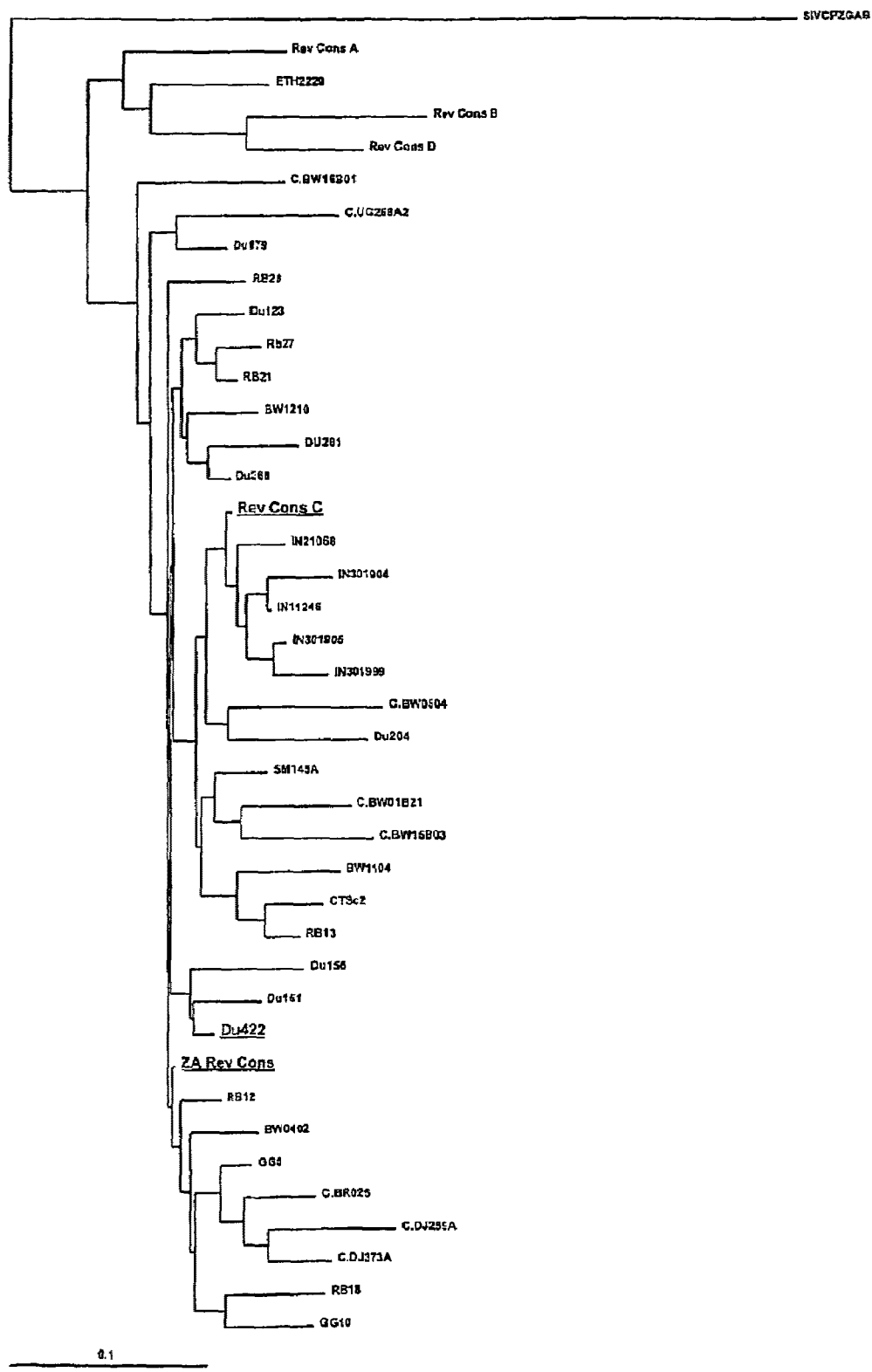
Figure 33:
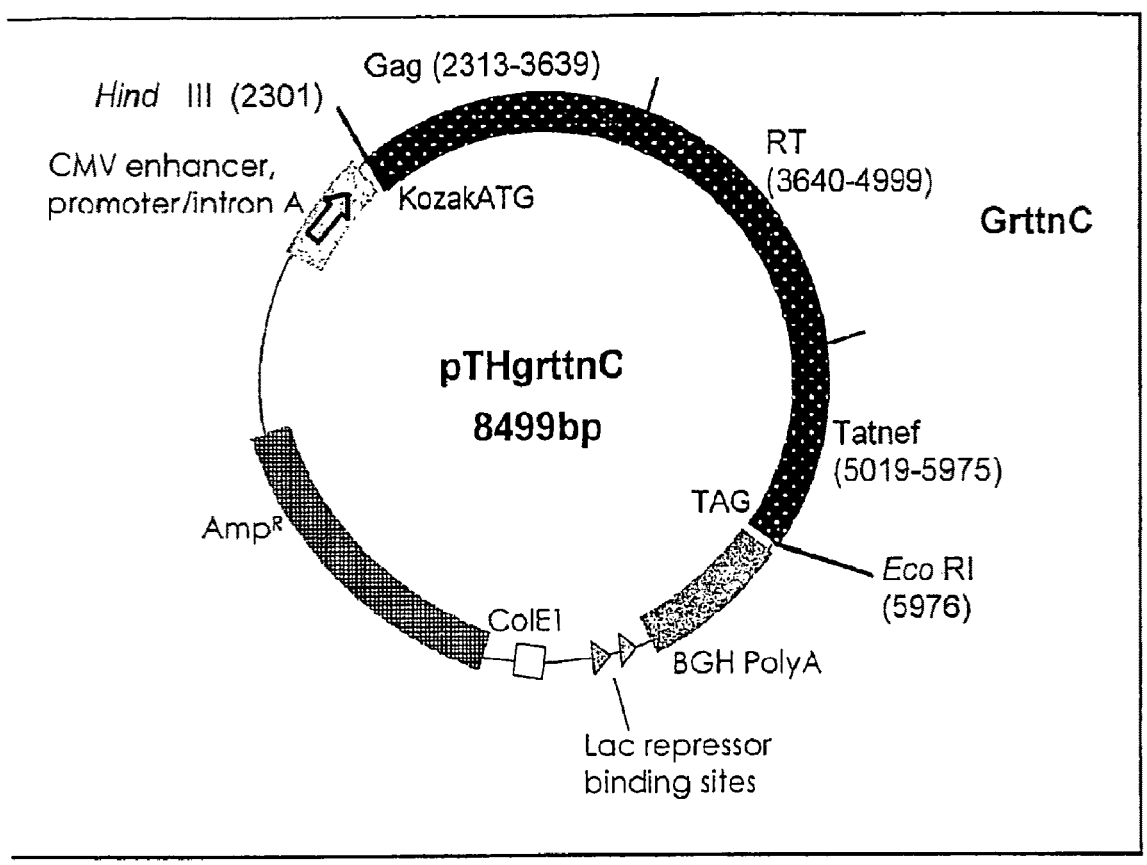
FIG. 33 shows a plasmid map of pTHgrttnC, the DNA vaccine vector expressing GrttnC for prophylactic or therapeutic use against HIV infection.

The nucleic acid sequences from the Durban (Du) Johannesburg (GG, RB, SW and COT) and Cape Town (CT) cohorts were phylogenetically compared to a number of available published subtype C sequences (obtained from the Los Alamos HIV Sequence Database) including sequences from the other southern African countries and the overall subtype C consensus from the Los Alamos HIV sequence database. This comparison was done to ensure that the selected vaccine isolates were not phylogenetic outliers when compared to the Southern African sequences and the results of the comparison are shown in FIG. 19, FIG. 20 and FIG. 21. FIGS. 19 to 21 illustrate that the sequences from Southern Africa are divergent and that the Indian sequences usually form a separate distinct cluster from these African sequences. The South African sequences are not unique and, in general, are as related to each other as they are to other sequences from Southern Africa. Overall this suggests Indian sequences are unique from Southern African subtype C sequences and that we do not have a clonal epidemic in South Africa, but rather South African viruses reflect the diversity of subtype C viruses in the Southern African region Determination of a Consensus Sequence Amino acid sequences were derived from the sequences shown in Table 2 and were used to determine a South African consensus sequence. The most frequently appearing amino acid at each position was selected as the consensus amino acid at that position. In this way, the consensus sequence was determined along the linear length of each of the sequenced genes (tat, rev and nef genes). The alignments were done using the DNAMAN program (DNAMAN2 output), which generates a consensus sequence in this manner. These resulted in the consensus sequence for each gene region. The alignments of the amino acid sequences and the resulting consensus sequences are shown in FIGS. 22, 23 and 24 (SEQ ID NOs: 39-56, 57-89 and 90-107, respectively). The amino acid similarities are shown in FIGS. 25 to 27.

The final choice of which isolate or isolates to use was based on the similarity of the sequence of the tat, rev and nef genes of a particular isolate to the South African consensus sequence that had been derived as set out above, as well as the availability of an R5 isolate which had good replication kinetics as shown in Table 1.

Selection of Vaccine Isolates

Based on the considerations and methodology set out above, two strains were selected from the acute infection cohort as the vaccine strains. The first strain is Du151 for the tat and nef genes and the second strain is Du422 for the tat and rev genes. These three strains were selected for the following reasons:

1. At the time the samples were obtained, Du151 had been infected for 6 weeks and had a CD4 count of 367 cells per ul of blood and a viral load above 500,000 copies per ml of plasma. Given the high viral load, and the recorded time from infection, it is probable that the individual was still in the initial stages of viraemia prior to control of HIV replication by the immune system.
2. At the time the samples were obtained, Du422 had been infected for 4 months with a CD4 count of 397 cells per ul of blood and a viral load of 17,118 copies per ml of plasma. In contrast to Du151, this individual had already brought viral replication under control to a certain extent.

Both isolates are able to grow in cell culture and have been sequence analyzed throughout their whole genome.

Based on the analysis of the amino acid pairwise comparison between Du151 and Du422 Tat protein sequences and other isolates shown in FIG. 28, the Du151 and Du422 tat sequences were shown to be very similar to the South African consensus sequence shown in FIGS. 19 and 22. They shared 89.4% (Du151) and 91.6% (Du422) amino acid sequence identity with the consensus sequence. Both Du151 and Du422 were thus used to generate the resynthesized, shuffled Tat in both a wild-type (non-codon optimized) and humanized (codon-optimized) form. They were chosen over slightly closer related isolates to the South African consensus sequence due to their ability to grow in tissue culture and due to both isolates entire genome having been sequenced and characterized.

Figure 29:
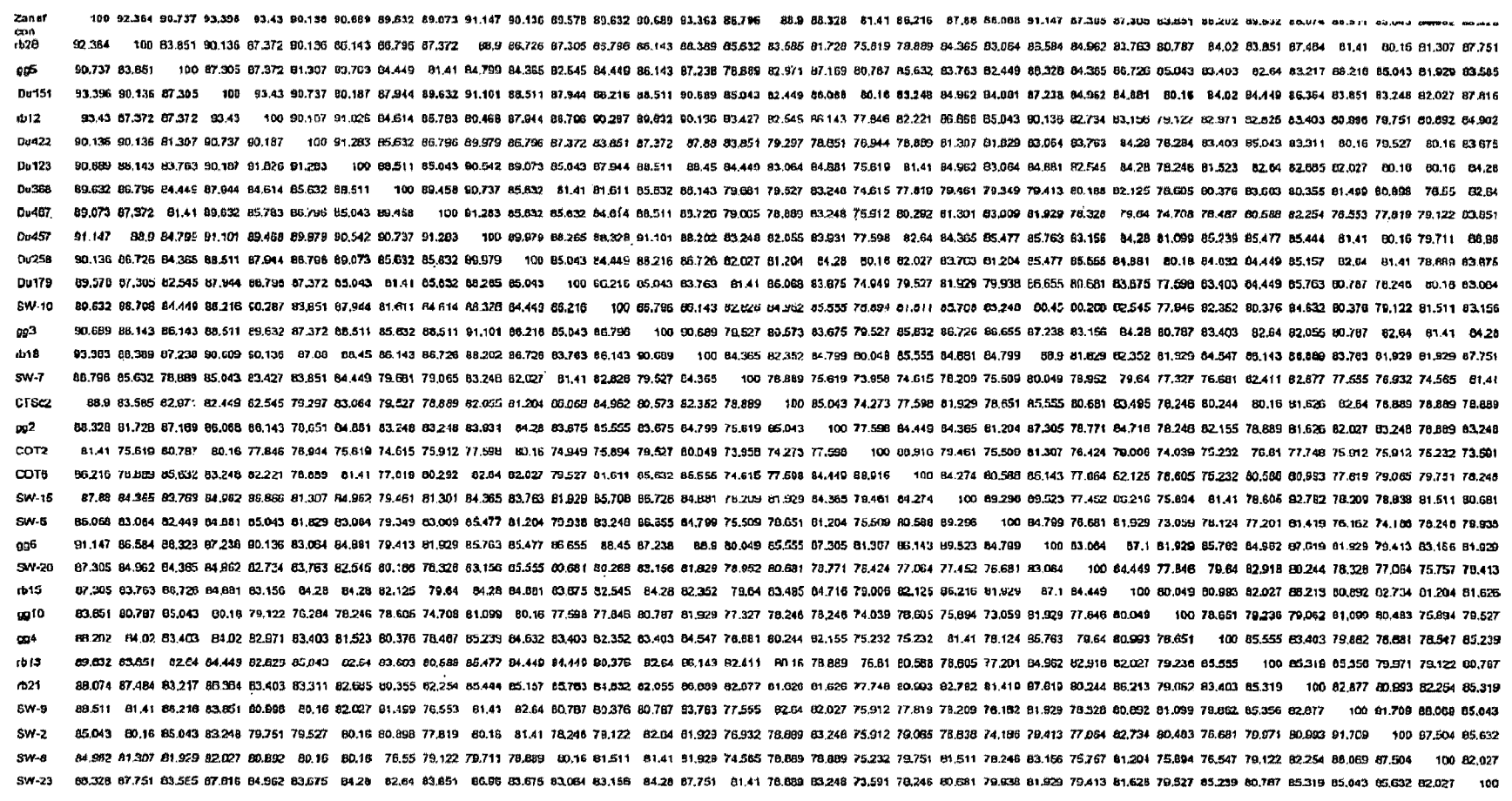

The nef gene showed the greatest sequence diversity. Based on the analysis of the Nef amino acid pairwise identity score with the SA consensus (93.4%) shown in FIG. 29, we chose the Du151 isolate as the source of the nef gene. All pairwise identity scores are above 80.2% with either the Du151 isolate sequence when compared to the other recent seroconverters, as shown in FIG. 29. Other contributing factors in this decision were that this is the same isolate that was chosen for the source of the env and pol genes and that this was an isolate with excellent growth properties in vitro.

The rev gene was the most conserved of the three. Based on the amino acid pairwise identity score with the SA consensus (95.2%), the Du422 rev gene was selected. In addition, all pairwise identity scores are above 83% with the Du422 isolate sequence when compared to the other recent seroconverters, as shown in FIG. 30. These pairwise scores make the Du422 sequence similar to the best scores in this sequence pool and combine these levels of similarity with an R5 virus with good cell culture replication kinetics.

Resynthesis of Genes

The Tat-nef polyprotein gene was produced by synthesis of oligonucleotide fragments that were ligated together to form the full gene by GeneArt (geneart GmbH, Regensburg). The codon optimised and non-codon optimised versions were synthesised and cloned into pPCR-Script (Stratagene) vector.

The identity of the insert was confirmed by sequencing the insert on both strands and comparing these sequences to the original sequences. The modifications to the tat and nef gene sequences of Du422/Du151 and Du151 separately and Tat-nef polyprotein gene sequence are shown in Sequence I.D. Nos. 9-17.

The Tat protein was split into three overlapping fragments and reshuffled (as shown in FIG. 31(SEQ ID NOs: 108-111)) to inactivate the protein, making it safer, but without losing potential CTL epitopes. The Nef protein was shortened by 10 amino acids, removing the N terminal myristylation site that allows the Nef protein to exit the cell (SEQ I.D. No. 12). Apart from making the protein safer, it is hoped that this will result in a more efficient CTL response, as the protein is trapped inside the cell.

Vaccine Development

The vaccines of the invention will be formulated in a number of different ways using a variety of different vectors. They involve encapsulating RNA or transcribed DNA sequences from the viruses in a variety of different vectors. The vaccines may contain at least part of the tat and rev genes from the Du422 isolate, and at least part of the tat and nef genes from the Du151 isolate of the present invention or derivatives or modifications thereof.

Genes for use in DNA vaccines have been resynthesized to reflect human codon usage. The tat Du422 gene was also divided into three fragments with overlapping ends so that no potential CTL epitopes are lost and reshuffled to improve safety of the Tat protein. The Du151 nef gene had the first 10 amino acids deleted to remove the myristylation site for safety reasons. The reshuffled tat and shortened nef were then synthesised together in the same reading frame to constitute a Tat-Nef polyprotein. Both humanised and non-humanised versions of the Tat-nef polyprotein have been synthesised for alternative vaccines. A similarly codon optimised rev gene may be expressed by DNA vaccines.

Other vaccines will contain DNA transcribed from the RNA for the tat gene from the Du422 and Du151 isolates, DNA transcribed from the RNA for the nef gene from the Du151 isolate and DNA transcribed from the RNA for the rev gene from the Du422 isolate. These genes could also be expressed as oligomeric envelope glycoprotein complexes (Progenics, USA) as published in *J Virol* 2000 January; 74(2): 627-43 (Binley, J. L. et al.), or in the adeno associated virus (AAV) (Target Genetics), the Venezuelan equine encephalitus virus (U.S. patent application USSN Ser. No. 60/216,995, which is incorporated herein by reference) as well as in Modified Vaccinia Ankara (MVA) (Amara et al., 2002), BCG and other vaccines being developed at the University of Cape Town.

A vaccine construct containing an in frame polygene, GrttnC (FIGS. 32*a* and 32*b*; SEQ I.D. Nos. 29 and 30) including codon optimised Du422 gag (FIGS. 34 and 35; SEQ I.D. Nos. 31 and 32), Du151 RT (reverse transcriptase) (FIGS. 36 and 37; SEQ I.D. Nos. 33 and 34) (WO 02/04494, the contents of which are incorporated herein by reference) and the shuffled tat-truncated nef (SEQ I.D. No. 17) has been developed and will be incorporated into a number of vaccine candidates, including a DNA vaccine, pTHgrttnC (FIG. 33) using the pTH DNA vaccine vector (Hanke et al., 2000) and an MVA vaccine (Amara et al., 2002). The nucleotide and amino acid sequences of the gag and pol genes isolated from Du422 and Du151 are shown in SEQ I.D. Nos. 35 to 38, respectively.

The invention is not intended to be limited to the precise embodiments described.

Deposits

The following material has been deposited with the European Collection of Cell Cultures, Centre for Applied Microbiology and Research, Salisbury, Wiltshire SP4 OJG, United Kingdom (ECACC).

| Material | ECACC Deposit No. | Deposit Date |
|---|---|---|
| HIV-1 Viral isolate Du151 | Accession Number 00072724 | 27 Jul. 2000 |
| HIV-1 Viral isolate Du422 | Provisional Accession Number 00072726 | 27 Jul. 2000 |
| | Provisional Accession Number 01032114 | 22 Mar. 2001 |

The deposit was made under the provisions of the Budapest Treaty on the International Recognition of the Deposit of Microorganisms for the Purpose of Patent Procedure and regulations thereunder (Budapest Treaty).

REFERENCES

UNAIDS. AIDS epidemic update. Dec. 1999. www.unaids.org/hivaidsinfo/documents.html Addo, M. M., Altfeld, M., Rosenburg, E. S., Eldridge, R. L., Philips, M. N., Habeeb, K,. Khatri, A., Brander, C., Robbins, G. K., Mazzara, G. P., Goulder, P. J. R., Walker, B. D., and the HIV Controller Study Collaboration. (2001). The HIV-1 regulatory proteins Tat and Rev are frequently targeted by cytotoxic T lymphocytes derived from HIV-1-infected individuals. *Proc Natl Acad Sci USA* 98(4): 1781-1786.

Allen, T. M., O'Connor, D. H., Jing, P., Dzuris, J. L., Mothe, B. R., Vogel, T. U., Dunphy, E., Liebl, M. E., Emerson, C., Wilson, N., Kunstman, K. J., Wang, X., Allison, D. B., Hughes, A. L., Desrosiers, R. C., Altman, J. D., Wolinsky, S. M., Sette, A. and Watkins, D. I. (2000). Tat-specific cytotoxic T lymphocytes select for SIV escape variants during resolution of primary viraemia. *Nature* 407(6802): 386-90.

Amara R R, Villinger F, Staprans S I, Altman J D, Montefiori D C, Kozyr N L, Xu Y, Wyatt L S, Earl P L, Herndon J G, McClure H M, Moss B, Robinson H L. (2002). Different patterns of immune responses but similar control of a simian-human immunodeficiency virus 89.6P mucosal challenge by modified vaccinia virus Ankara (MVA) and DNA/MVA vaccines. *J Virol* August; 76(15):7625-31.

Betts, M. R., Krowka, J., Santamaria, C., Balsamo, K., Gao, F., Mulundu, G., Luo, C., N'Gandu, N., Sheppard, H., Hahn, B. H., Allen, S, and Frelinger, J. A. (1997). Cross-clade human immunodeficiency virus (HIV)-specific cytotoxic T-lymphocyte responses in HIV-infected Zambians. *J Virol,* 71(11):8908-11.

Binley J M, Sanders R W, Clas B, Schuelke N, Master A, Guo Y, Kajumo F, Anselma D J, Maddon P J, Olson W C, Moore J P., (2000). *J Virol* January; 74(2):627-43

Bjorndal, A., Sonnerborg, A., Tscherning, C., Albert, J. & Fenyo, E. M. (1999). Phenotypic characteristics of human immunodeficiency virus type 1 subtype C isolates of Ethiopian AIDS patients. *AIDS Res Hum Retroviruses.* 15(7): 647-53.

Calarota, S. A., Kjerrstrom, A., Islam, K. B., and Wahren, B. (2001). Gene combination raises broad human immunodeficiency virus-specific cytotoxicity. *Hum Gene Ther* 12(13):1623-37.

Calarota, S. A., Leandersson, A. C., Bratt, G., Hinkula, J., Klinman, D. M., Weinhold, K. J., Sandstrom, E. and Wahren, B. (1999). Immune responses in asymptomatic HIV-1-infected patients after HIV-DNA immunization followed by highly active antiretroviral treatment. *J. Immunol.* 163(4):2330-8.

Connor, R., Sheridan, K., Ceraldini, D., Choe, S. & Landau, N. (1997). Changes in co-receptor use correlates with disease progression in HIV-1-infected individuals. *J Exp Med* 185, 621-628.

Durali D, Morvan J, Letourneur F, Schmitt D, Guegan N, Dalod M, Saragosti S, Sicard D, Levy J P & Gomard E (1998). Cross-reactions between the cytotoxic T-lymphocyte responses of human immunodeficiency virus-infected African and European patients. *J Virol* 72:3547-53.

Ferrari G, Humphrey W, McElrath M J, Excler J L, Duliege A M, Clements M L, Corey L C, Bolognesi D P & Weinhold K J (1997). Clade B-based HIV-1 vaccines elicit cross-clade cytotoxic T lymphocyte reactivities in uninfected volunteers. *Proc Natl Acad Sci USA* 94(4):1396-401.

Hanke T, McMichael A J. (2000). Design and construction of an experimental HIV-1 vaccine for a year-2000 clinical trial in Kenya. *Nat. Med September;* 6(9):951-5.

HIV Molecular Immunology Database 1998: Korber B, Brander C, Koup R, Walker B, Haynes B, & Moore J, Eds. Theoretical Biology and Biophysics Group, Los Alamos National Laboratory, Los Alamos, N. Mex.

Klotman, M. E., Kim, S., Buchbinder, A., DeRossi, A., Baltimore, D. and Wong-Staal, F. (1991). Kinetics of expression of multiply spliced RNA in early human immunodeficiency virus type 1 infection of lymphocytes and monocytes. *Proc Natl Acad Sci USA*. 88(11):5011-5.

Kostrikis, L. G., Cao, Y., Ngai, H., Moore, J. P. & Ho, D. D (1996). Quantitative analysis of serum neutralization of human immunodeficiency virus type 1 from subtypes A, B, C, D, E, F, and I: lack of direct correlation between neutralization serotypes and genetic subtypes and evidence for prevalent serum-dependent infectivity enhancement. *J. Virol.* 70, 445-458.

Koup R A, Safrit J T, Cao Y, Andrews C A, McLeod G, Borkowsky W, Farthing C, Ho D D (1994). Temporal association of cellular immune responses with the initial control of viremia in primary human immunodeficiency virus type 1 syndrome. *J. Virol.* 68(7):4650-5.

Moore J P, Cao Y, Leu J, Qin L, Korber B & Ho D D (1996). Inter- and intraclade neutralization of human immunodeficiency virus type 1: genetic clades do not correspond to neutralization serotypes but partially correspond to gp120 antigenic serotypes. *J. Virol.* 70, 427-444.

Ogg G S, Kostense S, Klein M R, Jurriaans S, Hamann D, McMichael A J & Miedema F (1999). Longitudinal phenotypic analysis of human immunodeficiency virus type 1-specific cytotoxic T lymphocytes: correlation with disease progression. *J Virol;* 73(11):9153-60.

Peeters, M., Vincent, R., Perret, J.-L., Lasky, M., Patrel, D., Liegeois, F., Courgnaud, V., Seng, R., Matton, T., Molinier, S. & Delaporte, E. (1999). Evidence for differences in MT2 cell tropism according to genetic subtypes of HIV-1: syncitium-inducing variants seem rare among subtype C HIV-1 viruses. *J Acquir Imm Def Synd* 20, 115-121.

Richman, D. & Bozzette, S. (1994). The impact of the syncytium-inducing phenotype of human immunodeficiency virus on disease progression. *J Inf Dis* 169, 968-974.

Robertson D L, Anderson J P, Bradac J A, Carr J K, Foley B, Funkhouser R K, Gao R, Hahn B H, Kalish M L, Kuiken C, Learn G H Leitner T, McCutchan F, Osmanov S, Peeters M, Pieniazek D, Salminen M, Sharp P M, Wolinsky S, Korber B (2000). HIV nomenclature proposal. *Science* 7; 288 (5463):55-6.

Rowland-Jones S L, Dong T, Fowke K R, Kimani J, Krausa P, Newell H, Blanchard T, Ariyoshi K, Oyugi J, Ngugi E, Bwayo J, MacDonald K S, McMichael A J & Plummer F A (1998). Cytotoxic T-cell responses to multiple conserved epitopes in HIV-resistant prostitutes in Nairobi. *J. Clin. Invest.* 102 (9): 1758-1765.

Scarlatti, G., Tresoldi, E., Bjorndal, A., Fredriksson, R., Colognesi, C., Deng, H., Malnati, M., Plebani, A., Siccardi, A., Littman, D., Fenyo, E. & Lusso, P. (1997). In vivo evolution of HIV-1 co-receptor usage and sensitivity to chemokine-mediated suppression. *Nat Med* 3, 1259-1265.

Schmitz J E, Kuroda M J, Santra S, Sasseville V G, Simon M A, Lifton M A, Racz P, Tenner-Racz K, Dalesandro M, Scallon B J, Ghrayeb J, Forman M A, Montefiori D C, Rieber E P, Letvin N L, Reimann K A (1999). Control of viremia in simian immunodeficiency virus infection by CD8+ lymphocytes. *Science* 5; 283(5403):857-60.

Summary Report National HIV sero-prevalence survey of women attending public antenatal clinics in South Africa, 2000 (2001). Department of Health, Directorate: Health Systems Research & Epidemiology, April 2001.

Tscherning, C., Alaeus, A., Fredriksson, R., Bjorndal, A., Deng, H., Littman, D., Fenyo, E. M. & Alberts, J. (1998). Differences in chemokine co-receptor usage between genetic subtypes of HIV-1. *Virology* 241, 181-188.

The invention claimed is:

1. A polypeptide comprising:
   (i) the amino acid sequence as set forth in amino acids 1-196 of SEQ ID NO: 14;
   (ii) the amino acid sequence as set forth in amino acids 1-207 of SEQ ID NO: 6; or
   (iii) an amino acid sequence that is at least 95% similar to the amino acid sequence as set forth in amino acids 1-196 of SEQ ID NO: 14 or amino acids 1-207 of SEQ ID NO: 6.

2. A polypeptide according to claim 1, comprising the amino acid sequence as set forth in SEQ ID NO: 6.

3. A polypeptide according to claim 1, comprising the amino acid sequence as set forth in SEQ ID NO: 14.

4. A polypeptide according to claim 1, further comprising:
   (i) a tat amino acid sequence as set forth in any one of SEQ ID NOs: 2, 4 or 11; or
   (ii) a sequence which is at least 95% similar to any one of SEQ ID NOs: 2, 4 or 11.

5. A polypeptide according to claim 4, comprising:
   (i) the amino acid sequence as set forth in amino acids 1-318 of SEQ ID NO: 16; or
   (ii) an amino acid sequence that is at least 90% similar to the amino acid sequence as set forth in amino acids 1-318 of SEQ ID NO: 16.

6. A polypeptide according to claim 4, comprising the amino acid sequence as set forth in SEQ ID NO: 16.

7. A polypeptide according to claim 6, comprising:
   (i) the amino acid sequence as set forth in amino acids 1-1228 of SEQ ID NO: 30; or
   (ii) an amino acid sequence that is at least 90% similar to the amino acid sequence as set forth in amino acids 1-1228 of SEQ ID NO: 30.

8. A polypeptide according to claim 7, comprising the amino acid sequence as set forth in SEQ ID NO: 30.

* * * * *